(12) United States Patent
Goldstein

(10) Patent No.: US 12,193,841 B2
(45) Date of Patent: *Jan. 14, 2025

(54) SENSOR CONTROL OF AN AUDIO DEVICE

(71) Applicant: The Diablo Canyon Collective LLC, Wilmington, DE (US)

(72) Inventor: Steven Wayne Goldstein, Delray Beach, FL (US)

(73) Assignee: The Diablo Canyon Collective LLC, Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/221,065

(22) Filed: Jul. 12, 2023

(65) Prior Publication Data

US 2023/0346311 A1    Nov. 2, 2023

Related U.S. Application Data

(63) Continuation of application No. 16/545,680, filed on Aug. 20, 2019, now Pat. No. 11,759,149, which is a continuation of application No. 14/964,041, filed on Dec. 9, 2015, now Pat. No. 10,413,240.

(60) Provisional application No. 62/090,136, filed on Dec. 10, 2014.

(51) Int. Cl.
*H04R 1/10* (2006.01)
*A61B 5/00* (2006.01)
*A61B 5/0205* (2006.01)
*H04R 25/00* (2006.01)
*A61B 5/021* (2006.01)
*A61B 5/024* (2006.01)
*A61B 5/053* (2021.01)
*A61B 5/08* (2006.01)
*A61B 5/1455* (2006.01)

(52) U.S. Cl.
CPC ........ *A61B 5/6817* (2013.01); *A61B 5/02055* (2013.01); *H04R 25/00* (2013.01); *A61B 5/021* (2013.01); *A61B 5/02416* (2013.01); *A61B 5/053* (2013.01); *A61B 5/0816* (2013.01); *A61B 5/14551* (2013.01)

(58) Field of Classification Search
CPC ......... H04R 1/10; G06F 3/044; G06F 3/0414; G06F 3/04142
USPC ........................................ 381/74; 341/33, 34
See application file for complete search history.

(56) References Cited

U.S. PATENT DOCUMENTS

| | | | |
|---|---|---|---|
| 2,803,308 | A | 8/1957 | Mattia |
| 6,094,494 | A | 6/2000 | Haroldson |
| 6,513,621 | B1 | 2/2003 | Deslauriers et al. |
| 7,130,437 | B2 | 10/2006 | Stonikas et al. |
| 8,047,207 | B2 | 11/2011 | Perez et al. |
| 8,186,478 | B1 | 5/2012 | Grason |
| 8,229,128 | B2 | 7/2012 | Keady |
| 8,251,925 | B2 | 8/2012 | Staab et al. |
| 8,391,534 | B2 | 3/2013 | Ambrose et al. |
| 8,522,916 | B2 | 9/2013 | Keady |
| 8,548,181 | B2 | 10/2013 | Kraemer |
| 8,631,801 | B2 | 1/2014 | Keady |
| 8,649,540 | B2 | 2/2014 | Killion et al. |

(Continued)

FOREIGN PATENT DOCUMENTS

| | | |
|---|---|---|
| DE | 102012221233 | 3/2014 |
| DE | 102013203334 | 5/2014 |

(Continued)

*Primary Examiner* — George C Monikang
(74) *Attorney, Agent, or Firm* — Aikin & Gallant, LLP

(57) ABSTRACT

An electronic device tubular structure with sensors to control the device's functions.

20 Claims, 33 Drawing Sheets

(56) References Cited

U.S. PATENT DOCUMENTS

| | | |
|---|---|---|
| 8,678,011 B2 | 3/2014 | Goldstein et al. |
| 8,774,435 B2 | 7/2014 | Ambrose et al. |
| 8,792,669 B2 | 7/2014 | Harsch |
| 8,903,113 B2 | 12/2014 | Gebert |
| 8,942,405 B2 | 1/2015 | Jones et al. |
| 9,288,592 B2 | 3/2016 | Basseas |
| 9,338,568 B2 | 5/2016 | van Hal |
| 9,462,100 B2 | 10/2016 | Usher et al. |
| 10,045,107 B2 | 8/2018 | Kirsch et al. |
| 10,057,675 B2 | 8/2018 | Mankodi et al. |
| 10,506,320 B1 | 12/2019 | Lott |
| 10,917,711 B2 | 2/2021 | Higgins |
| 11,006,198 B2 | 5/2021 | Lott |
| 11,012,770 B2 | 5/2021 | Hatfield et al. |
| 11,294,619 B2 | 4/2022 | Usher et al. |
| 2004/0258263 A1 | 12/2004 | Saxton et al. |
| 2011/0079227 A1 | 4/2011 | Turncot et al. |
| 2013/0136285 A1 | 5/2013 | Naumann |
| 2013/0251172 A1 | 9/2013 | Mosseri |
| 2014/0205123 A1 | 7/2014 | Lafort et al. |
| 2016/0050483 A1 | 2/2016 | Kulavik et al. |
| 2016/0127818 A1 | 5/2016 | Ambrose |
| 2016/0295311 A1 | 10/2016 | Keady et al. |
| 2018/0098390 A1 | 4/2018 | Yagishita et al. |
| 2018/0220239 A1 | 8/2018 | Keady et al. |
| 2019/0387305 A1 | 12/2019 | Keady |
| 2021/0152924 A1 | 5/2021 | Keady |
| 2022/0061767 A1 | 3/2022 | Goldstein et al. |

FOREIGN PATENT DOCUMENTS

| | | |
|---|---|---|
| EP | 1841283 | 10/2007 |
| EP | 2749043 | 7/2014 |
| EP | 2991381 | 4/2019 |
| EP | 3068142 | 9/2019 |
| FR | 2560520 | 9/1985 |

121

250

270

280

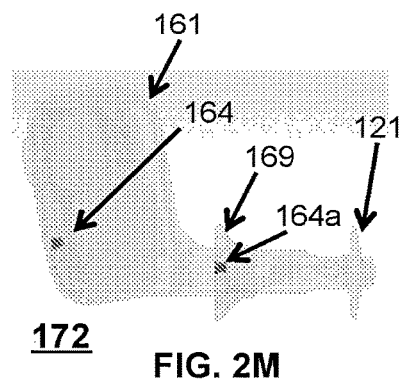
172   FIG. 2M
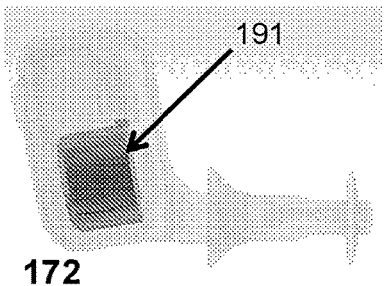
172   FIG. 2N
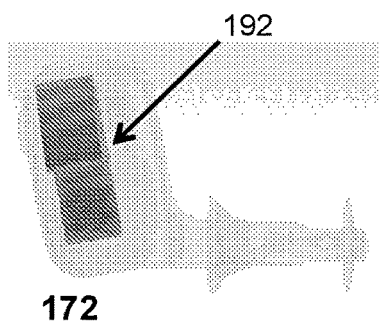
172   FIG. 2O
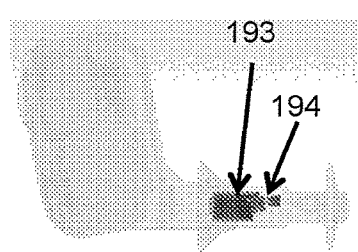
172   FIG. 2P
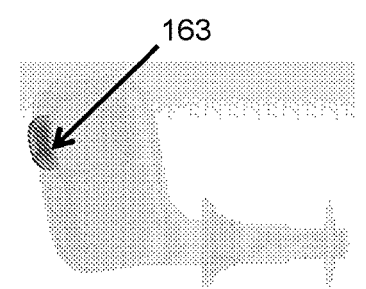
172   FIG. 2Q
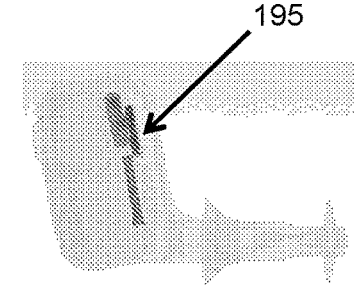
172   FIG. 2R
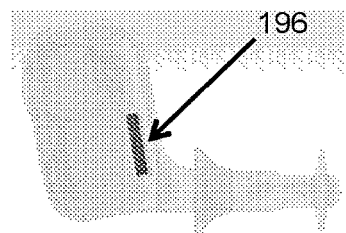
172   FIG. 2S
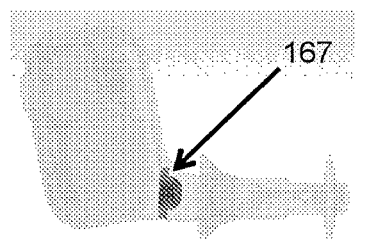
172   FIG. 2T
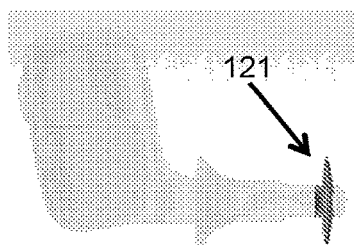
172   FIG. 2U
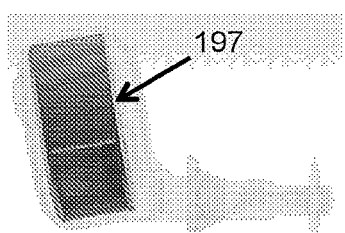
172   FIG. 2V

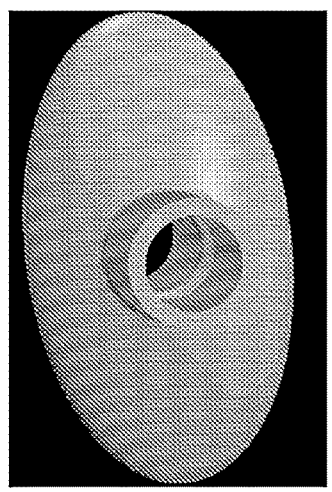
FIG. 2Z(1)
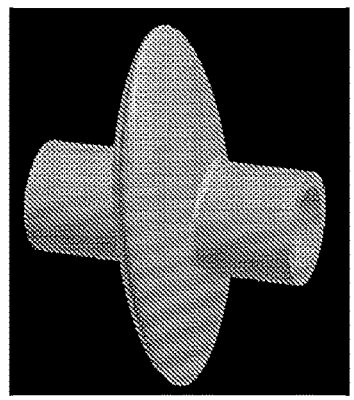
FIG. 2Z(2)
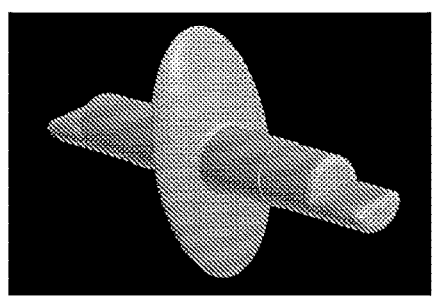
FIG. 2Z(3)
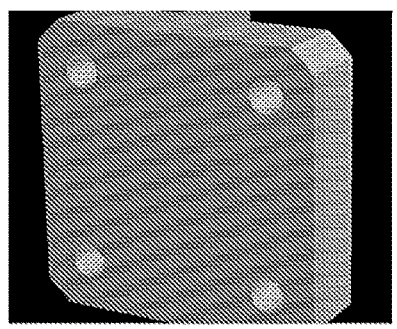
FIG. 2Z(4)
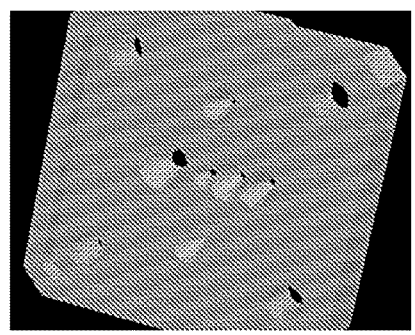
FIG. 2Z(5)
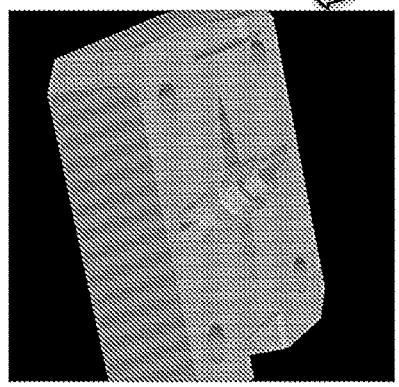
FIG. 2Z(6)
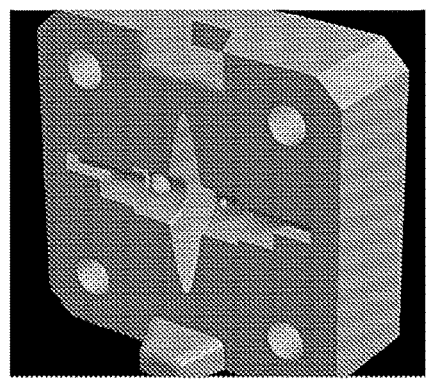
FIG. 2Z(7)

300

400

410

Side View

Top View

440

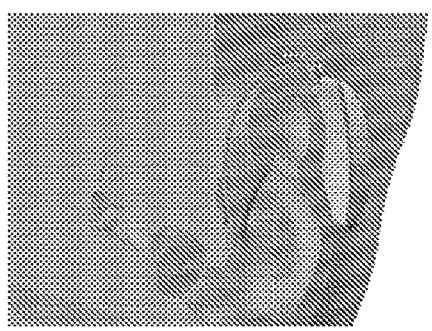
FIG. 4L
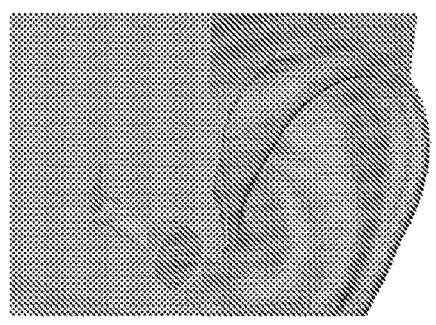
FIG. 4M
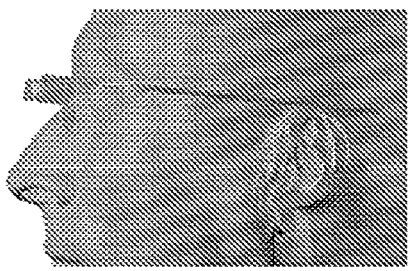
FIG. 4N
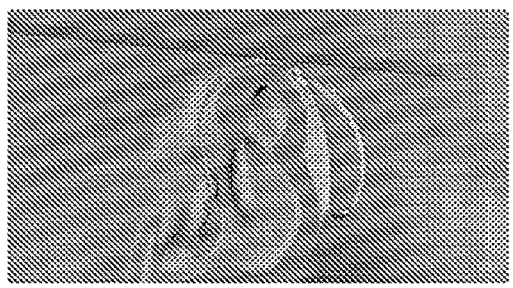
FIG. 4O
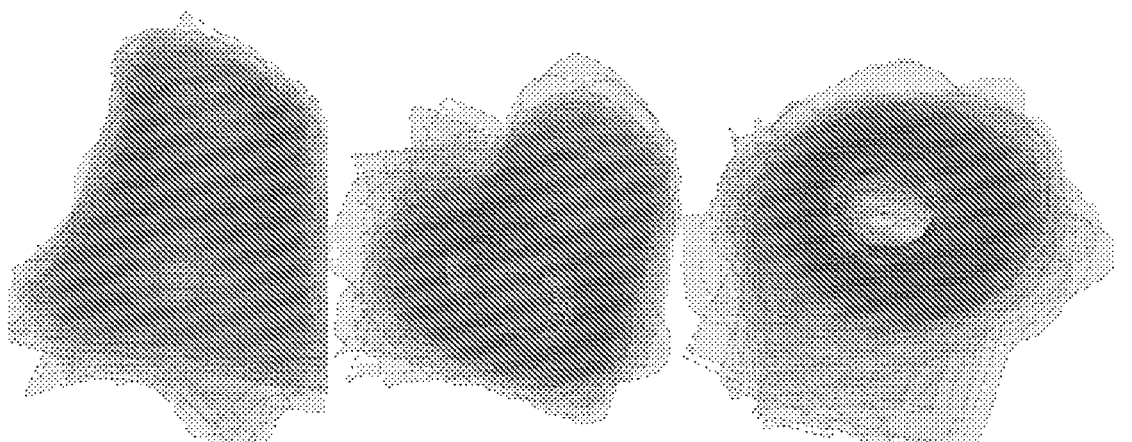
FIG. 4P(a)    FIG. 4Q(a)    FIG. 4R(a)
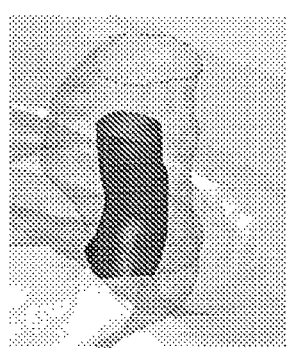   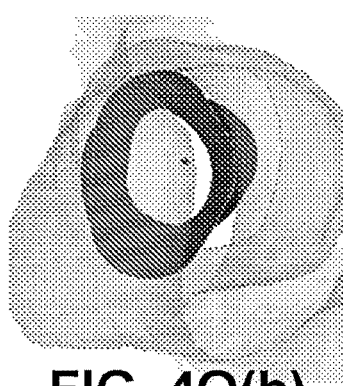   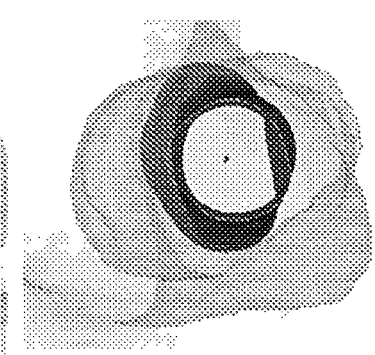
FIG. 4P(b)    FIG. 4Q(b)    FIG. 4R(b)

$ar = d\!\downarrow\!max / d\!\downarrow\!min$

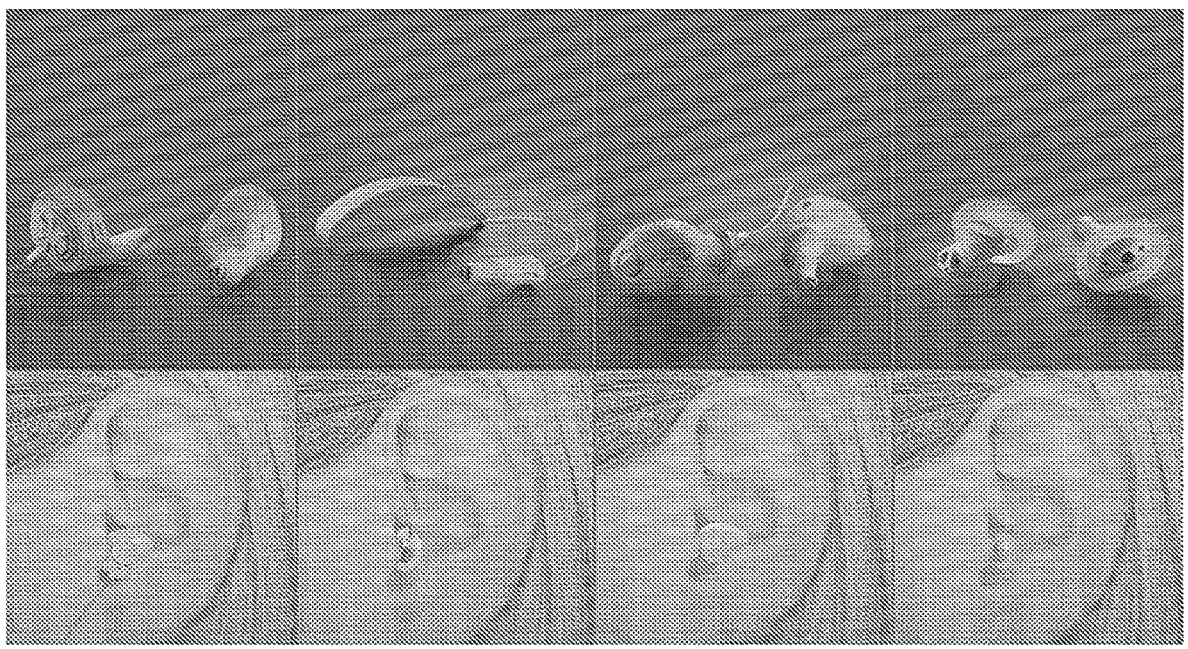
| 680 | 685 | 690 | 695 |
| FIG. 6K | FIG. 6L | FIG. 6M | FIG. 6N |

696

683

683

700

800

SENSOR CONTROL OF AN AUDIO DEVICE

CROSS REFERENCE TO RELATED APPLICATIONS

This application is a continuation of U.S. patent application Ser. No. 16/545,680 filed 20 Aug. 2019, which is a continuation of U.S. patent application Ser. No. 14/964,041 filed 9 Dec. 2015 that claims a priority benefit to Provisional Patent Application No. 62/090,136 entitled "Membrane and Balloon Systems and Designs for Conduits" filed on 10 Dec. 2014, the entire contents of all are incorporated herein by reference in their entirety.

FIELD

The present invention relates to optimally shaped membrane and designs, and more particularly, to balloon systems and designs used in human conduits such as ear canals.

BACKGROUND

Ergonomics and human functions are a fundamental part of good product design. Product usability, user-product performance, user satisfaction, and product safety and comfort are particularly important for devices that are in physical contact with the user for extended periods of time, such as, but not limited to, in-ear devices including earphones, hearing aids, and ear plugs. Comfort may be considered the most important factor regarding product compliance for products that are being worn. Ear interfacing fit and comfort for such products may be optimized through a myriad of design criteria including: tip insertion diameter, geometry, and material construction which reside internal to the External Auditory Canal (EAC), concha bowl housings geometry and their materials, as well as the geometry, weight and construction materials of behind-the-ear (BTE) type worn devices. Products not primarily worn for extensive periods of time, but used as tools for medical applications (e.g., ear-based drug delivery systems) have other factors besides comfort as a design consideration. Still other products that play music or provide a means of communication or information will also introduce further design considerations.

BRIEF DESCRIPTION OF THE DRAWINGS

FIGS. 2M-2V illustrate internal views with various components highlighted of the earpiece of FIG. 2L in accordance with an embodiment;

FIG. 2Z(1) through FIG. 2Z(7) illustrate a unique balloon geometry and method of manufacture using a core pin and mold;

FIG. 4L illustrates a best fit, curve and shape of another wireless behind the ear media accessory in accordance with an embodiment shown with a portion of a pinna removed;

FIG. 4M illustrates the wireless behind the ear media accessory of FIG. 4L with the pinna included such that the accessory remains hidden in accordance with an embodiment herein;

FIG. 4N illustrates the wireless behind the ear media accessory of FIG. 4L with the pinna removed and further operationally connected to eyewear in accordance with an embodiment herein;

FIG. 4O illustrates a closer view of the interconnection between the ear wear accessory and the eyewear of FIG. 4N;

FIGS. 4P(a), 4Q(a), 4R(a) and FIGS. 4P(b), 4Q(b), 4R(b) illustrate statistical models of the ear canal with a lower bound surface in accordance with an embodiment;

FIG. 5A illustrates a side view of eyewear communicatively and mechanically coupled to the wireless wearable media accessory in accordance with one exemplary embodiment;

FIG. 6K illustrates a wired wearable media device that includes a balloon;

FIG. 6L illustrates a wireless wearable media device in a BTE format in accordance with an embodiment;

FIG. 6M illustrates a wireless wearable media device worn in the concha bowl in accordance with an embodiment;

FIG. 6N illustrates a wireless wearable media device worn in the ear canal in accordance with an embodiment;

DETAILED DESCRIPTION

Figure 1A:
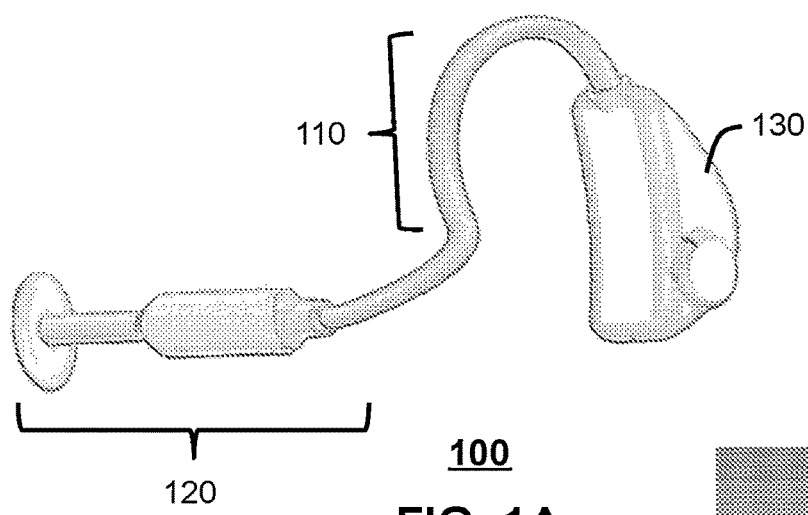
FIG. 1A illustrates a wireless wearable media accessory in accordance with an exemplary embodiment.

Some of the various embodiments herein stem from characteristics of the unique balloon geometry "UBG" sometimes referred to as stretched or flexible membranes, established from anthropomorphic studies of various biological lumens such as the external auditory canal (EAC) and further based on the "to be worn location" within the ear canal. Other embodiments herein additionally stem from the materials used in the construction of the UBG balloon, the techniques of manufacturing the UBG and the materials used for the filling of the UBG. Some embodiments exhibit an overall shape of the UBG as a prolate spheroid in geometry, easily identified by its polar axis being greater than the equatorial diameter (See item 121 of FIGS. 2A, 2B or item 602 of FIG. 6A). Prolate spheroids are elongated along a line, whereas oblate spheroids are contracted. (See FIG. 4T) The prolate spheroid is defined by the equation for some arbitrary constant c, in prolate spheroidal coordinates. Further, the UBG may take on the form of a specific ellipsoidal pattern known as a triaxial ellipsoid. This particular shape is an example that has been calibrated for specific locations within a human ear canal. The width and geometry of the balloon as well as the edge width (outside diameter or OD edge width, e.g., 0.5 mm) is specific to the goal of the wearability and comfort while being worn in the EAC. The width of the contact area may change based on the size and shape of the target orifice location and its corresponding geometry. In other embodiments, the wear location can include other human conduits (e.g., the nasal cavity or other biological conduits), but the UBG for the EAC is described herein as an exemplary embodiment. An ideal size of 0.5 min for an OD edge width as determined from user feedback as well as from analysis obtained from computerized tomography (CT) scanning of general populations significantly drives the design and sizing. This narrow profile (e.g., with the 0.5 mm OD edge) facilitates an interface, which allows for the least amount of surface contact area and thus minimizes stimulation on the densely populated nerves residing within the ear canal. In this embodiment, the UBG could be worn at any location between the orifice to the end of the canal, but for illustration will be worn approximately 1-2 millimeters distal to the first bend of the EAC, typically 6-9 millimeters in length as measured from the orifice. Existing rubber plugs containing three to five flanges often referred to as "Christmas Tree" designs are very broad in their radius and are traditionally 7 mm in length while making contact with the epithelium walls of the EAC. This translates to approximately 25-30% of the total EAC wall surface being in contact with the rubber plug. Foam plugs are traditionally 13 mm in length and contacts approximately 40% of the total contact surface within the ear canal when worn correctly. The UBG embodiments significantly reduce the total contact surface within the ear canal (to only 2-5%) yet provides enhanced acoustic attenuation performance over existing foam and rubber plug products. This is an example of using CT scanning technology to design an optimally shaped membrane for an outcome of maximum acoustical benefit and comfort. Other benefits can be engineered to include "best solution" across a broad range of canal geometries, maximum acoustical attenuation characteristics, maximum comfort, maximum stability, and best fit for a range of canal geometries and range of insertion depths. Further, the UBG outer body in whatever form it takes, could have smooth sides, ridges or undulations. Further, the UBG outer body in whatever form it takes could have variable flexibility, rigidity and pliancy.

The balloon can be used to enable a number of different solutions such as a passive hearing conversation device or as part of an active (amplified) device with or without biometric sensing implementations. It can also be used to occlude an ear canal to mitigate water flow such as needed for swimmers. In addition, the balloon can serve for passive acoustic attenuation such as to mitigate external/ambient sounds for enhancement of sleep, relief from loud traffic noise, relief from industrial noise and for basic hearing protection. Other factors should be considered if the overall earpiece is used for more than passive acoustic attenuation, which would include active electronics, battery, human factors as design based in operational interface requirements, etc. Yet other factors such as mandibular movement may need to be considered, if the device would be worn during episodes of chewing. Still other applications allow for the use of the balloon for TMJ treatment. In another embodiment, the UBG or balloon can be used to dispense and deliver medication, which can further be titrated based on some predetermined time constant. In another embodiment, the balloon can be used to occlude a portion of the anatomy be it human or animal for various purposed including, but not limited to inhibit bleeding or to use as a feeding tube to deliver nutrients to a patient. Still another embodiment utilizes the balloon for nasal valve expansion by carefully optimizing the shape of a balloon to fit in specific areas of the nasal passageway. Other embodiments consider the balloon having a extremely broad range of applications for use in other body orifice(s) and biological lumens such as vessels, (arteries and veins) ducts, air passages and cavities such as: ureter, urethra, ductal system as the biliary tree, and pancreatic duct and tracheal-bronchial system, neurological and the ventricular system.

In some embodiments, the UBG is produced as a solid member rather than a fluid filled device. In another embodiment, the UBG is filled with a material chosen from at least one of water, aphrons, water with solid or gelatinous particles suspended, or oil with particles suspended. In another embodiment, the UBG may be a hybrid system including a solid center with an outer area filled with one of the various mediums disclosed herein, yet in other embodiment the inner portion could be a fluid or gas medium with the outer surface as a solid. In some embodiments, the UBG can include a hollow core. A tunnel or aperture directly in the center or off axis can exist to accept a lumen or for affixing a lumen for audio input/output such as connections to speakers and microphone. In another embodiment, the UBG can be fabricated to include small internal passageways for which the filling medium must travel thorough. Reservoirs (see FIG. 2A or 2B) operate to store as well as provide for passage of fluid or other medium between the one or more reservoir areas and the balloon. Yet in another embodiment, the passageways could be elongated across the body of a device (see FIG. 6O) as to produce channels, which might be 0.25 mm to multiple millimeters in overall length. The length and corresponding surface area of the channel could be optimized as to tune the balloons' attenuation and resonance characteristics.

In one embodiment, the shape of the UBG is designed to reside and fit at the location near to the first bend or the second bend of the EAC. The UBG can have a narrow profile (see 121 of FIG. 1F, 272 of FIG. 2D or 2E, 292 of FIG. 2W, FIG. 2Z(2) as examples), be oval shaped, and designed to fit in a particular location in the EAC such that the UBG is prevented from dislodging out of the canal. The narrow profile or thin edge of the UGB reinforces the concept of having minimal physical impact on the canal. Silicone, thermoplastic elastomers (TPE), thermoplastic polyurethanes (TPU) or other materials providing elastomeric memory characteristics would be ideal in some embodiments. In some embodiments, the UBG would be produced larger than the target EAC diameter thus having an outward expanding force. Operationally during placement in or removal from the EAC, the UBG would not distort permanently, but would rather substantially retain its shape.

Relating to human anatomy, it is well known that there is a large degree of morphological variation across individuals. An example of such variation is the EAC, concha, pinna and pinna distance to the skull. Such variation often leads to custom molding of an earpiece for individuals for certain applications especially when comfort and fit and long-term wear are the target goals, but further study of such variations can lead to more adaptable products and solutions that are not as costly and labor intensive to produce than customized ear interface devices. International Patent Application WO2013086116 entitled Methods and Systems for Ear Device Design using Computerized Tomography (CT)-Collected Anthropomorphic Data describes the use of CT scans of ear anatomy for defining critical landmarks, morphological and anthropomorphic measurements which are used for designing various embodiments of an earpiece system whether passive or active. Similar studies can be accomplished for other body worn devices as to enable efficacy improvements and comfort. Still other studies can be performed to design specific UBG for surgical procedures.

Relating to the ear, the UBG and supporting operating electronics (also to be worn) have design criteria that are strategically identified based on application and location worn (or inserted to) or used. Various criteria used to make such determination, as an example, considering an earpiece operating in the ear, should consider the following (non-exhaustive list of) criteria: Degree of physical invisibility or on the opposite extreme the degree of visibility, attenuation performance, ones own perception of a foreign body inserted or worn within their ear canal, occlusion mitigation, duration of wear cycles, worn during sleep periods, ease of insertion and/or removal, biometric performance and robustness, ear canal microphone intelligibility, overall gain, hearing correction or augmentation, full-occluding or partial-occluding of the EAC, stability as considered from issues manifesting from the earphone accidently dislodging from the ear while worn, deformation of the pinna, based on sleep or helmet wear and its secondary impact of a device worn in part within the concha bowl, insertion depth of balloon in the EAC which and can vary from a shallow insertion typically identified as a location from the orifice of the canal to the first bend of the EAC to a deep insertion typically identified in proximity from the second bend to near (2-3 mm) of proximal of the tympanic membrane (TM).

The UBG designs for the ear as well as the methodology described in the various embodiments can cooperatively function with other passive (e.g., plugs) or active (e.g., electronic) components in an overall system. The primary examples described are generally for earpieces and communication systems (e.g., ear interface devices or ear canal based medication delivery systems) used in a variety of applications that provide one or more functions. Of course, the UBG design and implementation techniques are not necessarily limited to ear interface devices and can be used for other human conduits, lumens, orifices and cavities, but the focus of the remaining description will concentrate on earpieces and the ear canal. Some embodiments provide hearing protection devices capable of tunable acoustic attenuation. Some embodiments relate to ear plugs comprising a fluid-containing balloon or solid filled balloon for fully or partially occluding the ear canal, which are capable of being adjusted, for example, by modifying fluid composition and/or pressure within the balloon to vary attenuation at different frequencies of the audible sound spectrum. Other embodiments provide an ear-plug with fixed attenuation having a body of compressible/expandable-recovery material shaped and sized to fit in an ear canal and at least one chamber disposed within the body and comprising a filler material chosen from at least one of water, aphrons, water with solid or gelatinous particles suspended, or oil with particles suspended.

The balloon is often expanded from a smaller form factor to a larger form factor Once the balloon is inserted in the desired location in the canal and as such its design generally requires filling (dilation) with a gas or liquid (or other filler) and thus requires specific material barrier properties for the balloon construction based on criteria considering permeability, solubility, diffusivity and interaction of the of the fluid medium diffusion through the membrane of balloon material. A critical component of utilizing a balloon to occlude any of the human conduits, lumens, orifices and cavities, is that the balloon when required can be smaller in its overall volume and form factor than the body pathway it is traveling into or out from. Thus, the balloon in a less than fully inflated state (and subsequent reduced volume) can navigate the passageway with less friction and subsequently less trauma to adjacent tissue, than if it were fully inflated and passed to the same target location in the canal or in other body lumens or conduits. Furthermore, applications of the UBG drives balloon design limits in terms of its total expanded volume and geometry for reasons of safety, comfort fit, and wearability, as is used for occluding the ear canal or in other body lumens or conduits. In the case of the EAC, the balloon's manufactured final inflated shape should not expand beyond 20% of the design shape, as the balloon may no longer reside in the preferred location (see FIG. 2Y or FIG. 4V). Additionally, as the balloon in some embodiments is designed to travel deep into the ear canal, it requires the balloon diameter at times to be smaller in overall radius (OD) to enable navigation or traversing through the EAC's complex pathway, until it reaches its desired worn location. Limiting the volume of fluid, liquid, gel, or gas (or other filler) transferred to fully dilate the UBG accomplishes the goal of allowing a reduction of size (and associated mechanical and electronics in some cases) to travel into the ear canal and reach its intended target location. At that point, additional fluid or gas (or other filler) may be transported to the UBG via a lumen attached to the UBG as to expand across its horizontal and vertical axis so that the UBG either fully-occludes or partially occludes the EAC. Since the UBG's length is constrained by design, the length will not expand laterally more than 20% in this design. Accordingly, another characteristic of the polymer material used in the embodiments makes the UBG malleable and enables it to take on a smaller form-factor than the volume and external OD radius geometry when fully inflated when maximum operational pressure or fluid volume exists. As such, the membrane material used in the construction of the UBG in some embodiments exhibits semi-compliant behavior and properties and the polymer materials used in the construction of the UGB often offers elongation of 100%-1000%. In other words, when at full inflation, the balloon conforms to the general shape of the design model (said mold shape) of the EAC; yet the UBG also conforms to the unique geometry of the individual's EAC at a particular insertion-depth location.

The UBG is initially produced using one of many novel techniques regardless of the specific geometries, which will be discussed shortly. In one embodiment, the UBG may be produced from a low durometer elastomeric material such as silicone. Other polymer materials exhibiting similar elongation capabilities of 200%-1000% can be substituted. One process for the production of the UBS utilizes a core pin in tandem with a mold (see FIGS. 2Z(1)-2Z(3) of a core and pin and FIGS. 2Z(4)-2Z(7) of the mold. FIGS. 2Z(4) and 2Z(5) illustrate the respective outside portions of the mold. FIG. 2Z(6) illustrates a 3D internal surface of the mold and represents the inside surface of the mold portion of FIG. 2Z(4) when turned or flipped toward the left along on a vertical axis. FIG. 2Z(7) illustrates another 3D internal surface of the mold and represents the inside portion of the mold portion 2Z(5) when turned or flipped right along a horizontal axis). The mold would incorporate the outer geometrical shape of the UBG, A core pin (seen in FIG. 2Z(3)) would be used to allow for a portion of the internal geometry of the balloon to be void of any solid material (Ms. 2Z(1) and 2Z(2) illustrate the balloon void of any solid material). During the molding process, the core pin is removed leaving an internal cavity. The balloon could then be filled with various mediums such as a high viscosity fluid. In the case of an earpiece, the fluid would enhance the acoustical attributes of the UBG and would allow for the UM to be act as noise mitigation membrane. In another embodiment, a rotational molding part technology used to produce elastomeric products such as blood pressure bulbs, cuff manometer bulbs, dust blower, ear- and ulcer syringes, nasal aspirators, manual breast pumps, breast shells, vaginal douches, enemas, irrigation systems, seat cushions, hot water bottles, massage and reflex balls in the rotational mold can be used. In another embodiment, a blow-molding process is utilized beginning with an extrusion and mold, which is calibrated to produce the final desired geometry and dimensions of the UBG. In some embodiments, the desired balloon geometry can be spherical. In some embodiments, the desired balloon geometry is ovular (oval in shape and see discussion of prolate ellipsoid or prolate spheroid-shaped balloon further below) and has a narrow-width (or profile) edge of 0.5 mm-2 mm (see 158 in FIG. 1E for example). The width of the balloon is controlled based on the elongation properties of the polymer materials used as well as how it is bonded to the lumen, which is used to inflate the balloon. When comparing the semi-compliant balloon to a fully-compliant balloon, a fully-compliant balloon has an overall geometry that changes based on the volume of gas, fluid (or other filler) or based on the inflation pressure of the balloon.

The overall width can be further influenced, based in part on the two bonding sites that may be only 1 mm-2 mm apart as this provides for the balloon's overall width to be constrained. The narrow width serves a number of functions including the prevention of "billowing" of the balloon whereby the shape of vertical walls tend to flex and thus the entire balloon geometry broadens. Another benefit of the narrow width is the reduction in the interface (contact area) area between the balloon and the ear canal (tissue/bone) walls. One of the design goals is for minimal contact force on the very sensitive canal walls as well as the other regions of the body, thereby mitigating trauma to the nerves and pathways where the balloon is resting. For example, in the EAC, the UBG provides a reduction in the sensations caused by sensory innervation on the sensory auricular branch of the facial nerve.

The ovular geometry balloon is essentially shortest in a horizontal profile (see FIG. 1D or 1E for example), which enables the required volume of filling medium to be reduced in comparison to a spherical balloon. In one embodiment of the ovular balloon geometry, such UBG requires approximately 0.33 cc of fluid to reach full expansion. The smaller volume of fluid used to achieve full dilation (or filling and full expansion) of the UBG results in a smaller reservoir required (external to the UBG) to transfer the fluid into the UBG. The reservoir (or bladder) would typically be located external to the EAC, either in a temporary state or permanent state. The reservoir typically resides in the concha bowl or is located in a separate BTE body in some embodiments (See FIGS. 2A and 2B). In yet other embodiments, no reservoir is used, but the UBG or an associated earpiece can include a port or valve where filler materials can be injected using a separate external source of filler introduced when filling the UBG is desired. In one embodiment, the UBG can be pre-filled at the manufacturing stage and then the final fitting can occur in the field once the user attempts to fine tune the fitting of the UBG.

A balloon according to one embodiment roughly requires 0.3 cc of volume to expand it to a state of normal operation. It can be made from various polymers such as Polyurethane material such as Elastollan as well as Pebax or various silicone based materials. One enabling attribute is focused on the acoustical performance, which involves mitigation of the occlusion affect as well as the attenuation of ambient sound. Another attribute enables the fitting of the earpiece into a wide variety of ear geometries and expands to occlude the EAC regardless of the individual EAC geometry. Yet another attribute is the geometry of the balloon itself, which promotes maximum comfort during wear as the contact area between the balloon and the EAC wall and sensory nerves are physically minimized. The balloon is additionally physically designed for stability during wear and is also shaped with a narrow or thin profile. In one embodiment, when used in the EAC, the balloon extends past the first bend and when fully expanded and deployed provides a locking mechanism that enables the balloon to set into place at the first bend or just past the first bend in some embodiments and/or at the second bend or just past the second bend in other embodiments. Utilizing such a balloon design, which is produced with a thin profile, as described above minimizes the contact interface on the walls of the EAC.

In contrast to the UBG, open or closed cell foam plugs are always in a state of expansion and typically take up 7 mm-12 mm of contact area length within the EAC wall when properly inserted in the EAC. The foam plugs expand within seconds of roll-down (see page 2 of "Tips & Tools for Fitting and Using EAR™ Foam Plugs", by Aearo Company, 2001) and insertion and applies a pressure on the nerves within the ear canal and create wearing fatigue and irritation for the user which only increases over time. Existing rubber plugs also have similar detriments as the foam plugs although the rubber plug/tip is often shorter than a foam plug, yet it is designed to be larger in area than the location for which it is intended and as such exerts an undue force on the canal walls.

The UBG instead causes less sensory innervation. Sensory innervation of the auricle (or external ear) can be from many sources. For example, the outer more superficial surfaces of the auricle are supplied by the great auricular nerve (anterior and posterior inferior portions) and the lesser occipital nerve (posterior superior portion) from the cervical plexus and the auriculotemporal branch of the mandibular nerve (anterior superior portion). The deeper parts of the auricle are supplied by the vagus nerve (the auricular branch) and the facial nerve (which sends a branch to the auricular branch of the vagus nerve). Thus, a thin profile balloon such as the UBG would minimize stimulation impact on the various nerves residing in the EAC.

Minimization of the balloon is another design goal that ensures easy insertion and minimal discomfort by insertion of the balloon into the EAC. In some embodiments, the UBG is only partially inflated, thus in a smaller (rather than a fully inflated) configuration prior to insertion into the EAC and can be further inflated after insertion and placement in a resting position. Another feature enables the user to have full control over the operating volume and or pressure of the device while in the orifice. The overall operating pressure in combination with the filling medium will cause the balloon to exhibit a specific level of attenuation as well as modulate the sensation of the nerves. The level of attenuation is based generally on two factors, the first being the contact force which is applied to an ear canal, and the acoustical properties of the balloon and filler materials (see U.S. Patent Publication No. 2014/0146989 by Steven W. Goldstein and incorporated herein by reference). Based on a desired acoustical noise reduction level, the target expansion-area (e.g., expanding a body conduit so blood flow can be improved), where the balloon is installed or inserted in, or personal preferences, the balloon's contact force can be modulated from a low interface contact to a high-interface contact. As an example for acoustic based requirements, while in a battlefield condition, the user may choose to exert maximum force (sealing force) to mitigate potential Noise Induced hearing Loss. In another example, overall comfort may be the desired objective for a particular application, such as during sleep. In this situation, the balloon volume and thus its contact force may be dialed down to offer the greatest amount of comfort while still offering an adequate level of ambient noise reduction (attenuation). The enabling process to modulate the contact force is the transfer of fluid, gas or other filler to or from a bladder (or other reservoir) to the balloon residing in the canal as well as the operating pressure supplied to the balloon. Such modulation can be accomplished using a fluid transfer system with or without a direction and or pressure relief valve. The various types of filler used in a particular scenario may also serve as a modulating factor.

The tillable balloon is in contrast to open-cell or closed-cell foam plugs that are designed to be larger in radius (OD) (in its normal uncompressed state) than the typical geometry of the intended worn location within the EAC, and thus requires compression of the foam to take place (as to manipulate the foam in a shape) to be insertable into the canal. The foam plug is designed with memory materials so it attempts to return to its original shape, thus occluding the canal based on a much larger radius than is really necessary. As a result of the foam plug's material state of expansion, the foam plug constantly applies a contact force on a significant portion (defined by a length of the canal) of the EAC and often leads to, physical and sensory discomfort over time. In addition, as the contact force is constant with a foam plug, so is the level of attenuation. The foam plug only provides a static or fixed amount of attenuation based on the foam material properties along with the plugs insertion fit and depth of insertion typically guided by the wearer of the plug. Thus the attenuation is not controllable by the user.

As mentioned above, the gases, gels, and fluids (and other fillers or mediums) used to fill the balloon can be varied and configured for different purposes or applications. In some embodiments, the mediums can be a gas to enable a high pass filter (See US Patent Publication no. 20140146989) for mitigation of sounds such as low frequency sounds from compressors, low frequency rumbles, and human procured sounds such as snoring. In some embodiments, the medium can be a fluid used as to enable a low pass filter. Another characteristic of a high pass passive system is increased situation awareness for certain sounds in the environment, as a gas filled balloon tends to effect and mitigate acoustical energy below 1000 Hz. Accordingly, such a high pass passive system can be designed to distinguish important vs annoying sounds where important sounds that need to be heard such as glass braking from as a home invasion, or a baby crying can be better heard with the gas filled balloon as compared to foam or rubber type plugs. These other non-balloon devices will mitigate acoustical energy at about 1000 hz with greater attenuation, so they tend to decrease the wearers situation awareness and could promote a decreased sense of critical sounds and other dangerous auditory stimulus levels. In yet other embodiments, specific fluid can be used to achieve a broadband filter (see US Patent Publication no. 20140146989). The balloon itself and the fluids, gases and other mediums used to fill it with can be made of biocompatible materials to avoid irritation and pathological changes to the user (particularly in the event of an unforeseen rupture of the balloon). In some embodiments, the fluids can further be thermally stable and resistant to heat conduction. Such fluids such as silicone oil are available in a variety of medium to high viscosities and are considered thermally stable and heat resistant based on the range of temperature a user would typically experience. Ambient heat and cold typically experienced while the earphone is being carried by the user (versus worn by the user) may reduce the viscosity of silicone-based oils, but heat transfer or thermal conduction is minimal and thereby suitable for placement in an ear canal even in extreme conditions of heat or cold.

In one application, a specific type of fluid is used to fill the balloon, as is the case of impulse noise created by gunfire. The peak sound pressure level (SPL), and spreading of pressure wave and other physical characteristics of the impulse noise from weapons are well studied. The peak SPLs at the shooter's ear rings from 132 dB (miniature rifle) to 183 dB (howitzer). The spectral content of the main part of the acoustic energy was less than 400 Hz (peak 16-100 Hz) for large-caliber weapons and 150-2,500 Hz (peak 900-1,500 Hz) for small-caliber weapons (rifles). Similar acoustic events can occur in the industrial/manufacturing environments.

These extreme acoustical damaging conditions require a level of protection which exceeds that of most consumer protection requirements. One enablement of the balloon is to use a non-Newtonian fluid as the fill medium. These fluids offer shear thickening characteristics under stress causing the transfer of acoustic energy entering into the canal to be significantly attenuated as the acoustical incident is extreme in SPL and short in duration, the initial acoustical pressure wave which impact the balloon membrane causes the sound wave to be dampened by a strong mass effect enabled by the non-Newtonian fluid. Further, based on the Rheopecty property of some non-Newtonian fluids, the level of peak attenuation protection is increased due to the time-dependent increase in viscosity as the longer the fluid undergoes a shearing force when shaken and or stimulated, the higher the viscosity of the fluid.

Cerumen is produced in the outer third of the cartilaginous portion of the ear canal. It is a mixture of viscous secretions from sebaceous glands and less-viscous ones from modified apocrine sweat glands. Cerumen is composed mostly of dead skin cells and keratin with a small mixture of sweat, and oil. Cerumen is secreted from the ceruminous glands located in the first third outer part of the ear canal and is thought to be composed mainly of cholesterol, squalene, wax esters, ceramides, and triglycerides. The cerumen also has antimicrobial properties which can be attributed to its slight acidic pH.

Cerumen production is generally a good substance you would want the body to produce, as it lubricates your EAC and thus protects the canal from becoming dry and guards off infection. Cerumen is a combination of lubricating secretions, sloughed skin cells and dirt and dust trapped in the ear canal while trying to exit the canal. For the most part, the cerumen clears itself out of the EAC as it is continuously pushed out of the ear canal by the slow migration of the top layer of skin cells from the tympanic membrane towards the outer ear. The cerumen traps any foreign particles and organisms on its way out of the EAC. Attempts to manually clean the cerumen can do more harm than good, if wax is pushed further into the ear canal rather than extracted.

Cerumen can become impacted. This is frequently the case with people who wear hearings aid, or who use insert (in the canal) earphones, or foam plugs/rubber plugs. The constant insertion of these devices causes the cerumen to be compressed on itself and then pushed deeper in the EAC. The problem is further exacerbated as artificial devices such as hearing aids, or foam or rubber plugs are physically made to be larger in radius than the EAC itself as the cerumen debrides from the EAC walls and becomes compressed into the canal upon physical insertion of the larger radius devices. There are two implications of the balloon with respect to cerumen. The first is that the balloon does not scrape across the wall of the canal when at locations where the cerumen is produced, as it is smaller in volume than the EAC at the region. Additionally, the radius of the balloons walls are designed to facilitate the removal of the cerumen as the device is removed from the canal. This is accomplished with the design of the edge of the balloon such that the edge carries out cerumen upon removal of the balloon from the canal.

Jaw movement is also a significant consideration in the design of an earpiece and corresponding balloon. The majority of ear canals undergo significant movement relative to the concha. Medial-Lateral movement ranges from +2.0 to −3.8 mm; Superiorly-Inferiorly movement ranges from +3.7 to −2.7 mm; and Anteriorly-Posteriorly movement ranges between +7.5 and −8.5 mm. Recent studies have shown the variability of canal movement relative to the concha and does not support previous reports that suggest that the ear canal only widens with jaw opening. As such, the wall thickness and materials used to fill the balloon is of importance. The balloon geometry will need to flex, as the basic polymer will need to be malleable as to accommodate the jaw movements. Accordingly the overall balloon system will recover quickly and return itself to its original geometry. This malleability is accomplished by an appropriate selection of polymer materials for the balloon, the medium used to dilate the balloon, and the operating pressure of the balloon.

Acoustic emissions of polyurethane (PU) expansion is yet another consideration in the balloon design. At times, the balloon design is for wearing in the ear (versus in other orifices). As such, the balloon or membrane itself will exhibit an unwanted acoustic transmission behavior when expanding (dilating) and or during compression when flexed by chewing. This stems from when polymer facets suddenly buckle from one configuration to another. Studies have proved that every discrete pop one hears can be traced to a single facet of the (balloon) sheet undergoing a change of configuration; sounds do not appear to be produced directly by the formation of creases. To mitigate the phenomenon, one can apply or affix an elastomer film or electrometric polymer suspended in an aqueous form to both the exterior and interior of the balloon Polyurethane material. Another embodiment allows for the UBG to be made of a tri-layer material of PU and films such as Thermoplastic elastomers having a TPU Shore 50 A that can be bi-extruded or tri-extruded to produce the final extrusion, which will be blown into a balloon. The PU of Shore 80 A is sandwiched between the two outer layers of Thermoplastic elastomers of low durometer material which will isolate and mitigate acoustical emissions stimulated by the expansion and compression and movement of the PU.

Another feature of the balloon design is the aspect of "One or two sizes fits most". Anthropomorphic studies have guided the design of creating one or very few sizes that would accommodate a broad spectrum of the target population for these balloons and their accompanying earpiece elements without losing most or all of the benefits attributable to such design. The balloon can vary its overall outer dimensions as much as 50% based on the materials chosen and their elongation characteristics. As such, the balloon can be enlarged or reduced in OD based on an amount of fluid contained within the balloon and providing that the polymer selection for the balloon offers a suitable level of elongation. As such, only a few sizes are necessary to fit a large variation of EAC dimensions and geometries using a UBG with appropriately selected material characteristics. Further detail with respect to the descriptions below of FIGS. 4I, 4J, 4K, 4P, 4Q, and 4R among others will make this more apparent.

In some embodiments, biocompatible battery chemistry can be used as the fluids to fill the balloon and further provide a way to power electronic components of an associated earpiece. A balloon design can be partitioned into two discrete sections or other divisions to enable the operations of one or more flexible cathodes and anodes. In some embodiments, the material used for the balloon would be a dielectric elastomeric polymer. In some embodiments, the balloon would include a non-conductive (or semi-conductive) separator between the various battery chemistries. In some embodiments, the battery chemistry can include a biocompatible enzyme sugar while in other embodiments alkaline chemistry can be used. The bio-compatible battery liquid in the separate balloon chambers can generate power responsive to electrolysis, for instance, by creating an electrochemical gradient (voltage) between a first and a second bio-compatible battery liquid to power the electronic circuitry in the earpiece. In some embodiments, the dielectric material used for the balloon would use a layer of film to mitigate permeability of the balloon layer to avoid leaking.

Balloon wall thickness is another design consideration. The process of manufacturing a semi-complaint balloon is well known to those in the industry of balloon design. A process known as blow molding is typically utilized. First, a mold is created typically constructed of stainless steel. The mold is either machined or produced using Electrical Discharge machining to yield the final geometry of the balloon. A hollow tube called an extrusion is introduced into the mold and clamped off on one end. The mold is heated and the air or heated air is applied to the extrusion at a particular pressure (PSI), which often reaches up to 500 PSI. The extrusion then takes the form of the stainless steel mold and a balloon in the designated geometry is rendered. The wall thickness of the blown balloon is typically between 0.00005-0.000020 mm. This wall thickness enables the balloon to be malleable and to comply to the unique geometry of an individual ear canal yet also enables a physical boundary surface which will maintain the original geometry of the balloon without significant distortion under the intended operating pressure of the balloon while residing in the EAC. These pressures are typically between 1.2-1.4 ATM PSI. Based on other body orifices that the balloon would be designed to occlude, the wall thickness, geometry, materials, filling medium, operating pressure, resistance to specific body chemistry, (and if the balloon would be used to deliver medications) will all impact the operating design criteria and end product.

Applications for creating water resistant conduits (e.g., for swimming) presents additional considerations. In some embodiments, the balloon can be designed and shaped to include one or more seal rings or edges to seal out water from the EAC and yet still provide ease of insertion and comfort while being worn. The balloon itself can include anti-microbial materials to prevent the growth of bacteria on the device and the material can be soft, comfortable and flexible.

In some embodiment, the UBG can effectively enable delivery of medical solutions and agents to desired target areas in a human anatomy and equally prevent inadvertent leakage or flow of such solutions and agents in undesired areas of the human anatomy. In some embodiments, the UBG can form purposeful choke-off points or re-direct flow of bodily fluids or of ingested or injected fluids.

In some embodiments, the UBG can be used in the treatment of or for alleviation of Temporomandibular Joint disorder (TMJD). The UBG can replace the functionality of prosthetic devices described in US Patent Publication No. 20110130786, or US Patent No. 20140076336 or U.S. Pat. No. 8,002,829. In some embodiments, the UBG can support the TMJ and associated musculature to reduce strain in the TMJ and surrounding area. The UBG can further be designed to enable a user to more readily recognize their own habits such as jaw clenching that aggravate TMJD. Jaw movement as discussed above significantly impacts the ear canal. As the UBG is inflatable in some embodiments, the UBG can be adjusted for varying sizes of ear canals among the general population. One UBG in each ear would likely be recommended for wearing simultaneously, but in some embodiments one UBG in either the left or right ear might be recommended. Additionally, the UBG can concurrently enhance sleep based on the attenuation characteristics of the balloon.

In some embodiments, the balloon material itself can be a semi-compliant material made of a polyurethane having a hardness in approximately the range of 70-90 Shore A. Such a material is accommodating when placed or inserted within the EAC and adds another comfort factor to the overall design. In some embodiments, the balloon can be made of multiple layers of different polymer materials to achieve desired characteristics. In one embodiment, the multiple layers provides for a specific permeability characteristic that mitigates the flow of the fluid filler molecules through the balloon as well as keeping ambient gases from entering into the balloon membrane. Total wall thickness after blowing can range from X to Y.

In some embodiments, the balloon can be designed for deep insertion beyond a second bend of the EAC. Deep insertion is generally unnecessary for many applications and in many embodiments only a shallow insertion of the balloon to the first bend or just beyond the first bend is suitable for the particular application. In this regard, the designs herein take advantage of the EAC geometry and bends in the EAC to provide a design that prevents dislodging of the device once inserted. The ovular shape of the UBG and the rotation characteristics and bend in the EAC enables the UBG to be inserted and essentially locked into place. Furthermore, the shallow insertion and overall smaller device architecture overcomes the psychological barriers or phobias that some people may have of inserting devices in their ears. For example, foam plugs typically use at least 8 mm of depth within the EAC to perform properly and some people resist or form a psychological barrier that prevents them from inserting the foam plugs to the appropriate depth. The foam plugs are then inserted to an ineffective depth as a result. Using a UBG designed for shallow insertion depth obviates such barriers and provides greater ease of use for a broader population of users.

In some embodiments, the UBG can serve as the appliance or facilitator to house or enable various sensors. As one example, a biometric sensor can be a constructed material layer that in conjunction with the balloon senses changes in balloon size, pressure or shape depending on physiological states, for example, changes in ear canal size and shape, humidity, temperature and air properties. The biometric sensor can detect one or more biometric signals, alone or in combination with other sensors, for example, sensors measuring pulse, temperature, blood pressure, blood oxygenation, heart rate, respiratory rate, perspiration, humidity and acceleration, and chewing. The biometric sensor layer can be material, capacitive, resistive or optical coated. In one embodiment, the UBG or balloon can include conductive traces on the surface of the balloon to serve as a surface acoustic wave sensor that can be used for measuring blood pressure. In some embodiments, the conductive traces can be embedded within the balloon material or underneath the surface of the balloon. In yet another embodiment, the balloon can include an infrared thermometer that can take accurate temperature readings near the skull region of a user. The wide range of benefits as a result of the marriage of knowledge of balloon technology and ear geometry or anthropomorphics will become further apparent in the remainder of the detailed description below. In some embodiments one or more biometric sensors can be in, on, or within the balloon or embedded or encapsulated in, on or within the balloon.

In some embodiments, the detection of physical movement of the jaw using the biometric sensors and other sensors described above can serve to monitor the intake of food or compliance of medicine and/or of pills being swallowed. For example, biometric sensors in the balloon can operate to detect the swallowing of a pill or the chewing of food as the jaw moves. In another aspect, certain sounds can be further modeled and detected using sound signature detection of particular events further using a microphone as one of the sensors operating in conjunction with sensors in the balloon or independently. For example, the swallowing of a pill can be modeled and detected. Tracking the swallowing of a pill can help with medicine compliance issues with patients that are not steadfast in tracking their own intake of pills and medicines.

The chewing of food can also be modeled and detected. In some instances, the chewing of certain particular foods can also be modeled and detected such that a distinction can be made between certain types of foods being chewed and ingested (nuts, hard candies, meats, fruits, vegetables, liquids, etc.). Each food category or each individual food item likely has its own sound signature as it is being chewed and in some instances as it is being swallowed.

In some embodiments, the biometric balloon sensors can be used to track the movement of the mandibular or jaw as part of a voice activity detector or VAD. Vocalization by an individual (i.e. any utterance, term, or word that is can be spoken and recognized) is associated with a jaw movement by the individual. Therefore we can use jaw movement as a means to detect voice activity.

User voice activity (VA) status is the current state of vocalization of an individual: if the status is "true", then the individual has voice activity, and if it is "False" it is otherwise. The status may also be expressed as a probability, e.g. a value between 0 and 1 where a low value of VA status represents a low probability of voice activity, and a high VA status represents a high probability.

Such a VA status metric can be used in a number of systems: for instance in voice communication systems VA status can be used to gate (i.e. adjust the gain applied to) an outgoing voice signal, e.g. from a microphone detecting near end voice to a far end receiving system. VA status can also be used to gate a voice signal sent to a voice analysis system, or a voice recording system.

Voice activity and the corresponding jaw movement will generally affect the cross sectional area of the ear canal of an individual. For instance, when uttering the phoneme /a/, as in the word "far", the jaw is open and the ear canal cross section is different from its location for an "at rest" jaw.

A change in the cross section of an ear canal will affect the pressure on a tight fitting balloon within that ear canal. Therefore, we can determine that jaw movement has occurred if the pressure of a fluid in the balloon changes from the "at rest pressure to a different pressure. The pressure of the fluid in the balloon can be determined using a pressure sensor on the balloon surface, or by detecting acoustic vibrations within the balloon using a pressure sensor in the balloon liquid or mounted external to the balloon.

By monitoring changes in the deformation of a balloon in the ear canal of an individual, it can therefore be possible to determine the general or specific vocalization class uttered by this individual. By "general" vocalization class we mean determining if a vowel or fricative phoneme is spoken, and by "precise" vocalization class we mean determining exactly which phoneme was uttered.

The proposed system would associate a deformation characteristic (for example, a change in the pressure of a liquid) with a general or specific vocalization. Such a system could enhance the accuracy of determining which word is spoke by an individual, for example for use with an Automatic Speech Recognition (ASR) system, for example for a machine control system.

In some embodiments the biometric balloon sensors are used by themselves for this purpose. In some embodiments, the biometric balloon sensors are used with existing or modified VAD technology to provide a more robust VAD system.

Ergonomics and physical size plays an important roll in how a device is operated and interacted with, where and how it is worn, how physically secure it will be with the human body, how visible or discrete the physical product is in appearance and use, and how the materials used in the overall construction are perceived and adopted by the user.

The materials used for the balloon and accompanying earpiece should accommodate for not only convenient placement and removal of the balloon and earpiece, but should also accommodate the EAC when chewing or when other movements of the jaw are exhibited (e.g, yawning). As such, the materials used for the balloon should be soft and forgiving to accommodate such actions without significantly impacting overall performance characteristics.

In some embodiments, a balloon on a distal end of an orifice insertion device for insertion into a conduit includes a semi-compliant material forming the balloon and having controlled expansion characteristics controlling at least an OD of the balloon and further including a thin edge of the balloon configured to contact a region of the wall of the conduit when the balloon is inflated. In some embodiments, the semi-compliant material has less than ten percent (10%) elongation under a pressure of 2 atmospheres or less. In some embodiments, the balloon has a predefined inflation shape configured to fit the geometry of the conduit. In some embodiments, selection of materials used to produce the balloon is configured to minimize permeability of the internal gas or other mediums through the balloon membrane. In some embodiments, the selection of materials used to produce the balloon is configured to maximize permeability and diffusivity (through the balloon membrane) of the fluid, gas or other medium, as is the case for the delivery of a drug for the treatment of an Ear Infection (Otitis Media and Externa). Effective medications include ear drops containing antibiotics to fight infection, and corticosteroids to reduce swelling of the ear canal. These drops are typically applied using a wick or gauze which is inserted in the ear canal. These solutions using wicks or gauze are fraught with issues such as the wick or gauze becoming dislodged and are further complicated as the user is attempting to sleep based on their inability to restrain head movement during sleep. In the preferred embodiment, the balloon is designed to deliver medication thorough the propagation of the fluid through the walls and surfaces of the balloon. Specific properties inherent in polymers chosen will offer a rate of fluid diffusivity through the polymer. In addition to the polymer selected, another attribute of the fluid diffusivity property of the balloon can be further modulated by the wall thickness of the polymer. Based on the geometry of the balloon, it offers an unprecedented level of fit and stability, thus promoting high compliance from the user with enhancement of drug delivery efficacy based on the balloon's stability within the canal. In some embodiments, the delivery of nutrients can be delivered to the body. In some embodiments, the balloon is filed with a biocompatible fluid having vapor characteristics that leaves minimal residue. In some embodiments, the conduit for which the balloon travels through is one of a vascular channel, an biological conduit, an artery, a vein, a nasal passage, a sinus passage, a tracheal passage, a respiratory tract, or a pipe.

In some embodiments, the balloon is approximately 2.6 mils in width in its widest area and having a $1/10000$ wall thickness. In one embodiment, the balloon has a shape of 15 mm in height and 7.7 mm in width. In some embodiments, the balloon is approximately, 14.5 mm by 8 mm by 3 mm with a peripheral edge thickness of approximately 0.5 mm as illustrated in FIG. 1G.

In some embodiments, the balloon is configured for placement at a second bend of the ear canal. In some embodiments, the shape of the balloon emulates or is designed to fit within a belly of a second bend of the ear canal. In some embodiments, the balloon in an uninflated state is less than 3 mm in diameter, which is 25% less than 5th percentile of the female ear canal measurements. In some embodiments, the balloon is filled with a non-combustible fully fluoridated liquid whose viscosity is less than water. In some embodiments, the balloon in an uninflated state is undersized to avoid scraping or irritating the ear canal upon insertion. In some embodiments, the balloon is impervious to the occlusion effect upon inflation when sealing any location along the span of the ear canal. In some embodiments, the earpiece further comprises a stop flange section. In some embodiments, the balloon is configured to fit between 5th and 95th percentiles of the geometries of human ear canals based on anthropomorphic studies.

In some embodiments, methods herein make use of a repository of 3D ear models based on Computerized Tomography (CT) scans of the head for identifying and detecting relevant anatomic features of the ear. The method can further include taking measurements based on the identified features and then analyzing a distribution of the ear shape and size across various populations (e.g., gender, race, height, etc.). In one example, about 2000 head CT scans were collected. For each case, metadata such as Unique ID, Hospital, Age, Gender, Race, Height, and Weight were recorded.

FIG. 1A depicts an illustration of a wireless wearable media accessory 100 in accordance with one exemplary embodiment. The wearable media accessory 100 includes a Behind-the-Ear (hereinafter "BTE") module 130 shaped in accordance with statistical ear anatomy studies that provide a "best fit" approach along a post articular groove of an ear and behind the ear as explained ahead, an earpiece 120 that fits within an ear canal designed in accordance with statistical ear canal shape studies as explained ahead, and a "smart tube" or bend sensor 110 that couples the BTE module 130 to the earpiece 120. The bend sensor 110 is flexible to fit around and into the ear, and includes an interactive "smart skin" surface that is responsive to touch and enables a gesture based control signal for controlling at least one or more functions of the earpiece 120, for example, a volume control, media control, directional control, mute control, recording, and phone control. In some embodiments, the bend sensor 110 can also be used to control the filling of or displacement of fluid to or from the UBG or to control the corresponding contact pressure that is applied by the UBG to a contact surface or area within the EAC.

Figure 1B:
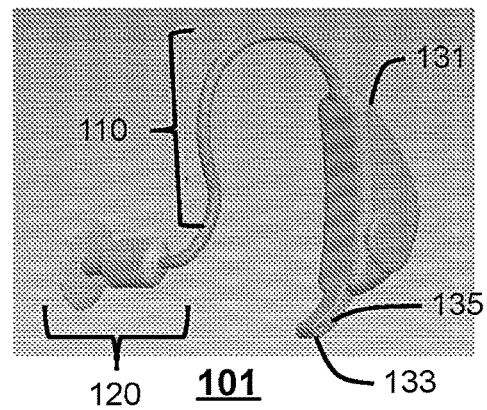
FIG. 1B illustrates another wireless wearable media accessory in accordance with an exemplary embodiment.

FIG. 1B illustrates a wireless wearable media accessory 101 similar to the accessory of 100 of FIG. 1A having the earpiece 120 and bend sensor 110, but alternatively including in some embodiments a BTE module 131 having an extension area 135 that includes an ambient sound microphone 133. Of course, an ambient sound microphone can be placed in other areas of the BTE module (130 or 131), the earpiece 120 itself, or in other locations operationally coupled to the wireless wearable media accessory 100 or 101.

Figure 1C:
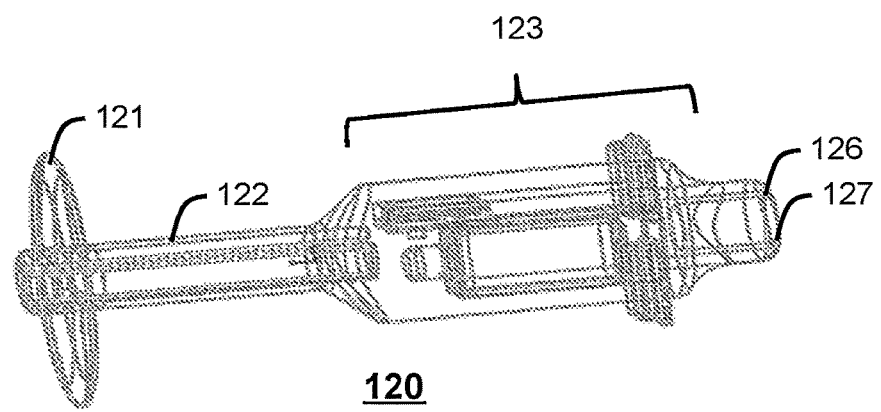
FIG. 1C illustrates an earpiece of the wireless wearable media accessory of FIG. 1A in accordance with an exemplary embodiment.

FIG. 1C is a detailed illustration of the earpiece 120 in accordance with one exemplary embodiment. The earpiece includes an expandable element such as a balloon 121, an extension 122 to seat the balloon within the ear canal, and a body portion 123 that fits comfortably within the opening orifice of the ear canal. The balloon 121 is a first feature that inflates within the ear canal for optimal comfort and sound experience, and by which to deliver audio signals and acoustic signals there through. The extension 122 ensures the earpiece balloon 121 is inserted at least past a first bend of the ear canal and is seated in proximity to the ear drum or tympanic membrane. The body portion 123 contains electronic components described below. In one arrangement, the earpiece 120 as shown is miniaturized to fit in its entirety within the ear canal. In some embodiments (as shown in FIGS. 1A and 1B), only portions of the overall device is intended to fit within the ear canal (with the BTE module 130 or 131 residing outside the ear canal).

The balloon 121 is inflated by way of a first lumen 126 serving as an inflation channel in the form of a tubular structure, which runs through the earpiece 120 to carry a fluid, or liquid, (or air or gel or other filler) to inflate and deflate the balloon. It may be a bio-compatible liquid or other non-allergic fluid for certain embodiments, and/or may carry an ion charge as part of a power source or battery in other embodiments. The first lumen 126, also called a fluid lumen conduit, in one embodiment can interface with the bend sensor 110 traveling its length to the BTE module 130 which stores the fluid. The fluid can be manually transferred through a physical pressing on a body of the BTE module 130, or electrically by way of a pump that transfers the fluid through the fluid lumen conduit to the balloon 121. In certain embodiments, the BTE module 130 or 131 (shown in FIG. 1A or 1B respectively) may also cause transfer of the fluid to perform the inflating or deflating operations of the balloon 121 responsive to touch based user interface gestures on the bend sensor 110. In some embodiments, the bend sensor 110 controls a pump residing in the BTE module, but the bend sensor 110 can be used for other controls as mentioned above and further discussed below. In other embodiments, the first lumen 126 may interface with a fluid source that is temporarily introduced such as a syringe or pressurized canister that delivers a controllable amount of fluid for inflation of the balloon 121, whereupon the fluid source is subsequently removed.

A second lumen 127, called an electrical lumen, also a tubular hollow structure, runs through the earpiece 120 and carries electrical wires to communicate and power the electronic circuitry in the body portion 123 of the earpiece 120. It also can interface through the bend sensor 110 traveling its length to the BTE module 130 for delivery of audio signals and the acoustic signals and to communicate control signals to the earpiece 120. As an example, the second lumen 127 carries a main wire for providing power, an audio signal wire to communicate audio content from the BTE module 130, and other wires for interfacing to microphones and transducers within the body portion 123 as will be seen ahead. One or both of the first lumen 126 and second lumen 127 may be present.

Figure 1D:
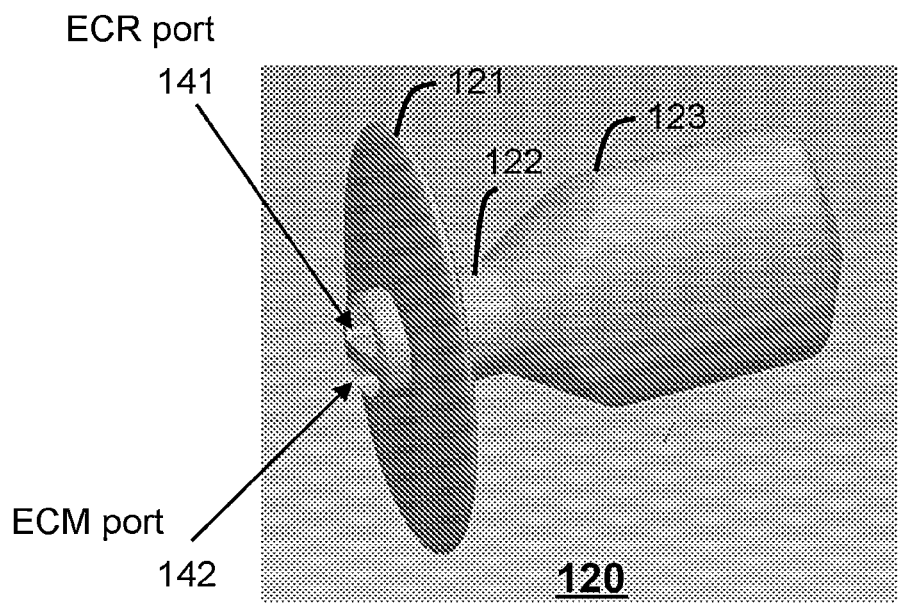
FIG. 1D illustrates a front perspective view of a balloon of the earpiece of FIG. 1B in accordance with an exemplary embodiment.

FIG. 1D is a more detailed illustration of the balloon 121 in accordance with one exemplary embodiment of the earpiece section. The earpiece 120 has been shortened in length only for illustration purposes; namely, the extension 122 and the body portion 123 shown in the previous figures have been shortened for illustration purposes. It should be noted also, that the extension 122, as will be described ahead, was designed to a predetermined length, width and durometer or hardness so as to be a best fit within a 95% confidence interval of a general population of ear canal sizes and shapes. The size of the extension may vary based on the overall design and intended location where the balloon may reside within the ear canal.

Figure 4A:
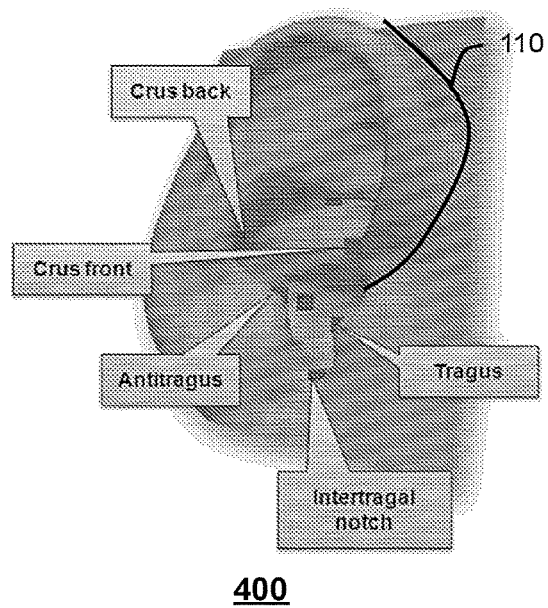
FIGS. 4A-4E illustrates an anatomy of the human ear with anatomical landmarks and features for study of an ergonomic and comfortable wearable earpiece component in the front of the ear.
Figure 4B:
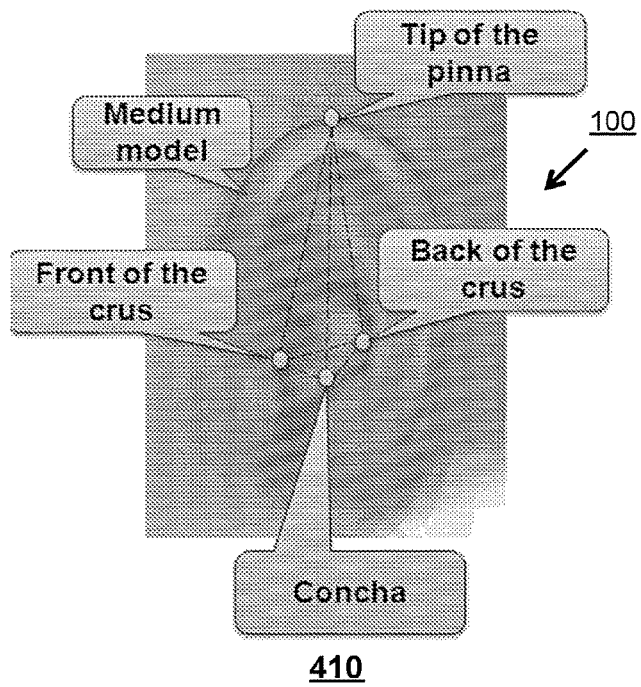
Figure 4C:
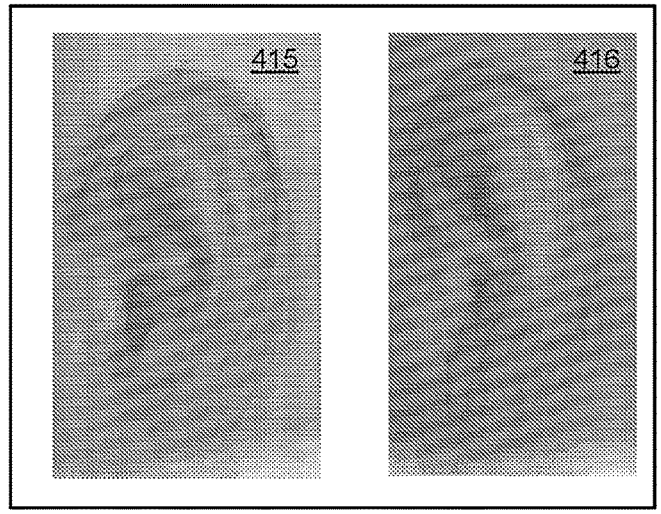
Figure 4D:
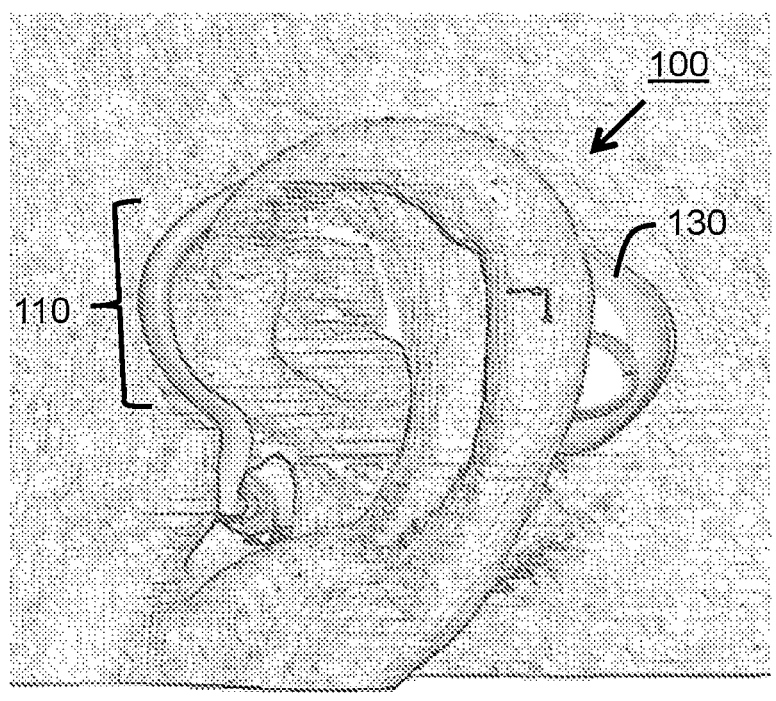
Figure 4E:
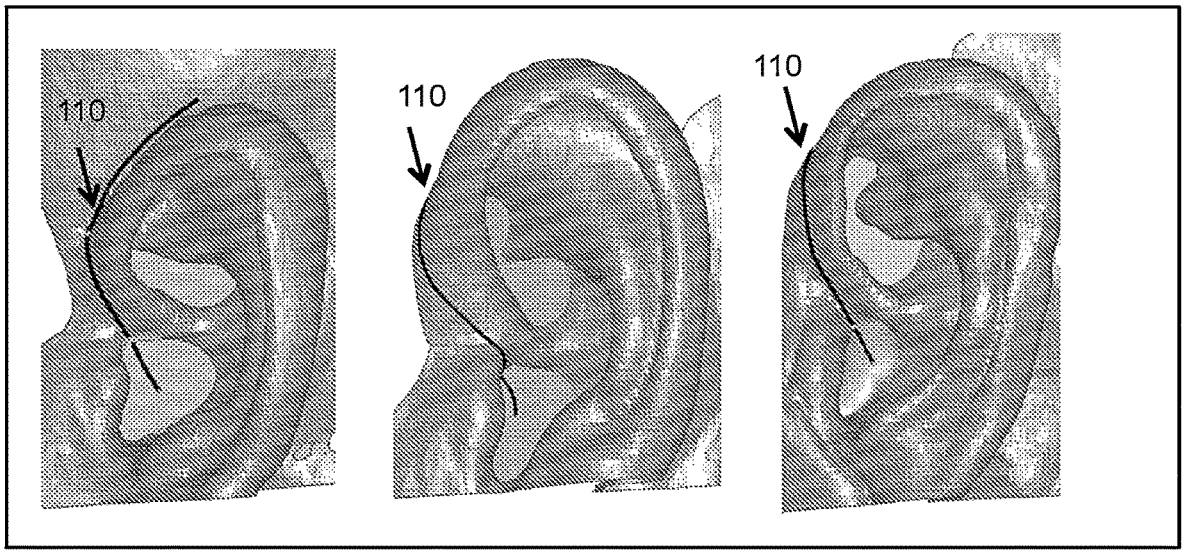
Figure 4F:
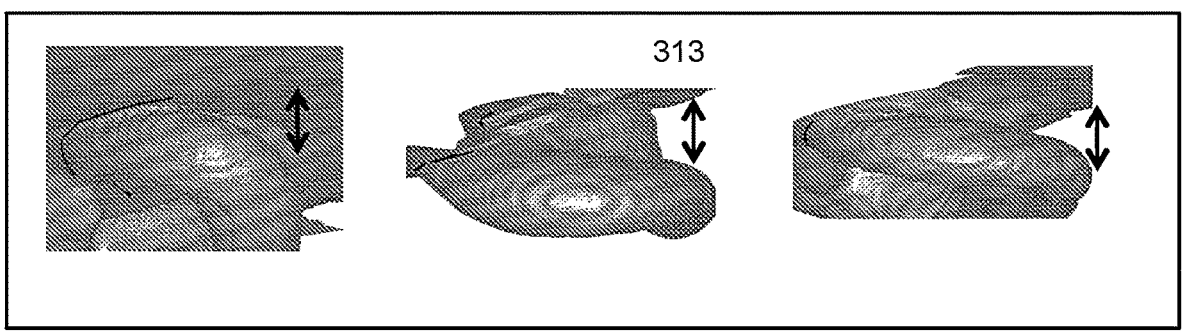
FIGS. 4F-4G illustrates an anatomy of the human ear with anatomical landmarks and features for study of an ergonomic and comfortable behind the ear component along the top of the ear.

The overall length of the earpiece can vary in different embodiments, but in some embodiments, the earpiece 120 is designed to fit between the orifice of the ear and the first bend of the EAC. In other words, the earpiece can be designed to fit in a cartilaginous region of the EAC rather than in a bony region of the EAC. The balloon 121 is also specifically designed in some embodiments to be ovular in shape due to the shaping of the first bend of the EAC. More particularly, the aspect ratio at the first bend is most dramatic as can be seen in FIGS. 4S-4U. Placement of the balloon at the first bend and use of an ovular shaped balloon using the UBG takes advantage of the shape of the EAC at the first bend and reduces the need to insert the earpiece further in the ear. Further note that such a device having a shallower insertion depth would likely create less discomfort while inserted in an ear since greater nerve density is generally found in the bony region deeper in the ear canal rather than in the cartilaginous regions of the EAC where the UBG is designed to seat.

Briefly, the balloon 121 extends and is expanded around the extension 122 to fill the ear canal there around, and seal the ear canal for an optimal comfort and sound experience. This design is configured to deliver audio signals and acoustic signals of high quality to the ear canal. In one arrangement, the balloon 121 semi-occludes the ear, for example if the balloon is partially inflated, or if inserted in a predetermined manner to intentionally partially seal the ear canal, for example, according to an applied rotation of the balloon within the ear canal. In another arrangement, the balloon 121 fully occludes and seals the ear canal from the external environment, for example, when the balloon is properly inserted to rotate and seat within a first bend of the ear canal (or within a second bend of the ear canal).

The use of the balloon has certain curious characteristics when used to occlude an ear canal, which makes the balloon immune to certain variables in terms of certain performance factors. For example, the size or length of the balloon and geometry of the balloon generally makes no difference in terms of mitigation of the occlusion effect and in terms of attenuation of ambient sound. Although some studies of foam plugs have indicated an improvement in the occlusion effect and attenuation the further foam plugs are inserted within the EAC, the balloon in contrast has no such variability or limitation. The balloon appears to work equally well whether placed beyond a second bend (for deep insertion devices) of the EAC or just beyond the first bend (for shallow insertion). As a result, several embodiments overcome the psychological resistance to deep insertion that some users may have of inserting earpieces within their ears since some embodiments only need to go only as far as the first bend of the EAC. Although some embodiments of the devices can be placed beyond the second bend, our devices in many embodiments just need to go only as far or just beyond the first bend (as a shallow insertion device) to operate as desired. In some embodiments when the earpiece is designed short enough, the earpiece can essentially remain hidden or invisible to an outside observer (see FIG. 6N).

An ovular shaped balloon (or a prolate ellipsoid or prolate spheroid-shaped balloon) with a thin edge or narrow profile further as in the UBG provides certain subtle characteristics. When using an ovular shaped balloon, the balloon can be rotated into the tortuous or spiral-like conduits of the EAC and can essentially lock into a first bend or a second bend (depending on the design of the overall earpiece). See FIG.

2X. This locking aspect makes the earpiece very stable once in place and very difficult for the earpiece to fall out. The thin edge of the balloon further creates a smaller contact area with the surface of the EAC and therefore mitigates overall contact area and reduces the possibility of necrosis of tissue. This arrangement provides more comfort and less fatigue when having the earpiece placed in the EAC. The ovular shaped balloon also mitigates the openings or possible leaks as the user moves their jaw when chewing or speaking. The thin ovular or oval shaped balloon also reduces the amount of fluid or air needed in a reservoir to inflate the balloon. Product materials can also provide further comfort and generally should be made of a soft low durameter material. As noted above, the balloon can be placed partially inflated and then further set by further inflation with filler material. In some embodiments, the balloon can already be filled with filler materials before insertion. In some embodiments, the balloon can be pre-filled at a manufacturing stage designed for a particular user. In some embodiments the balloon can already be filled with material that is already hardened and not necessarily in a fluid state, yet the shape remains as an oval having a thin edge or narrow profile.

One aspect of the balloon that does make a difference in performance is the filler, fluid or gas that is used to fill the balloon. Fluids generally provide greater attenuation performance than air or gases. Fluids chosen in one embodiment can use heavy viscosity fluids such as silicone oils that are available in different viscosities ranging from 1 centerpoise to 50,000+CP. In some embodiments, a broadband attenuation characteristic in the balloon design is desired and maintaining a system resonance above 4000 Hertz as to insure the ear canal microphone (ECM) pickup and lumen pathways, which transfer acoustical information, are not compromised. In one embodiment, a 1000 cP silicon fluid is used. In another embodiment, the addition of silica may be added to fluid to further increase the viscosity of the medium. Since the silicone fluid is thermally stable and heat resistant the fluid will not transfer high temperatures although the viscosity of the fluid may change. This is in contrast to materials like metal that would transfer heat when placed in contact with the ear. Note that complete attenuation to a human ear is generally impossible due to flanking pathways (such as passage ways from the eye sockets, nasal passages, mouth or throat) to the tympanic membrane and other parts of the ear.

Referring back to FIG. 1D and FIG. 1E, the extension 122 includes a first port 141 opening for a speaker such as an Ear Canal Receiver (151; see FIG. 1F) for delivering audio content to the ear canal. This hollow port 141 is where sound will be delivered from the earpiece 120 to the interior of the ear, for example, allowing the user to listen to music. The extension 122 may also include a second port 142 opening for a microphone such as an Ear Canal Microphone (ECM) (153; see FIG. 1F) whereby sounds within the ear canal are ported to the earpiece 120, for example, to measure sound levels within the ear canal, or to capture the users voice from internal voice articulations generated by speaking.

Figure 1E:
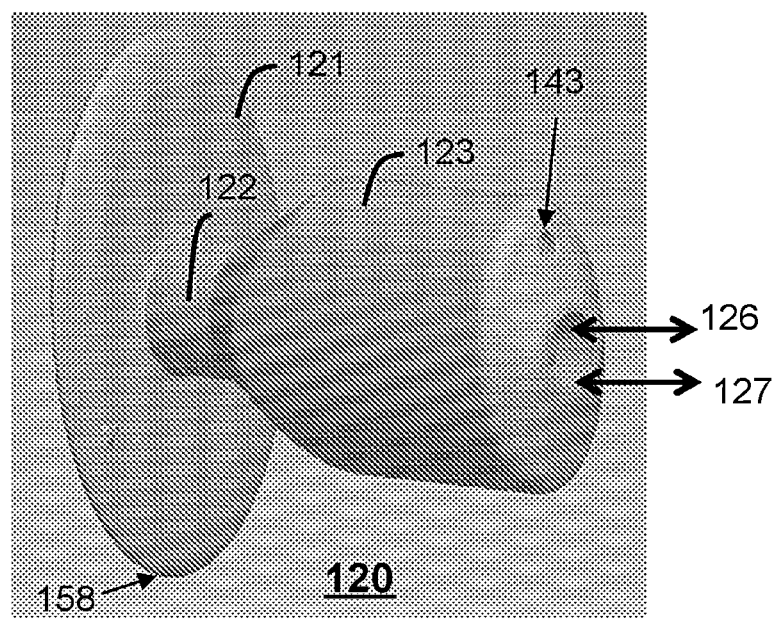
FIG. 1E illustrates a back perspective view of a balloon of the earpiece of FIG. 1B in accordance with an exemplary embodiment.
Figure 1F:
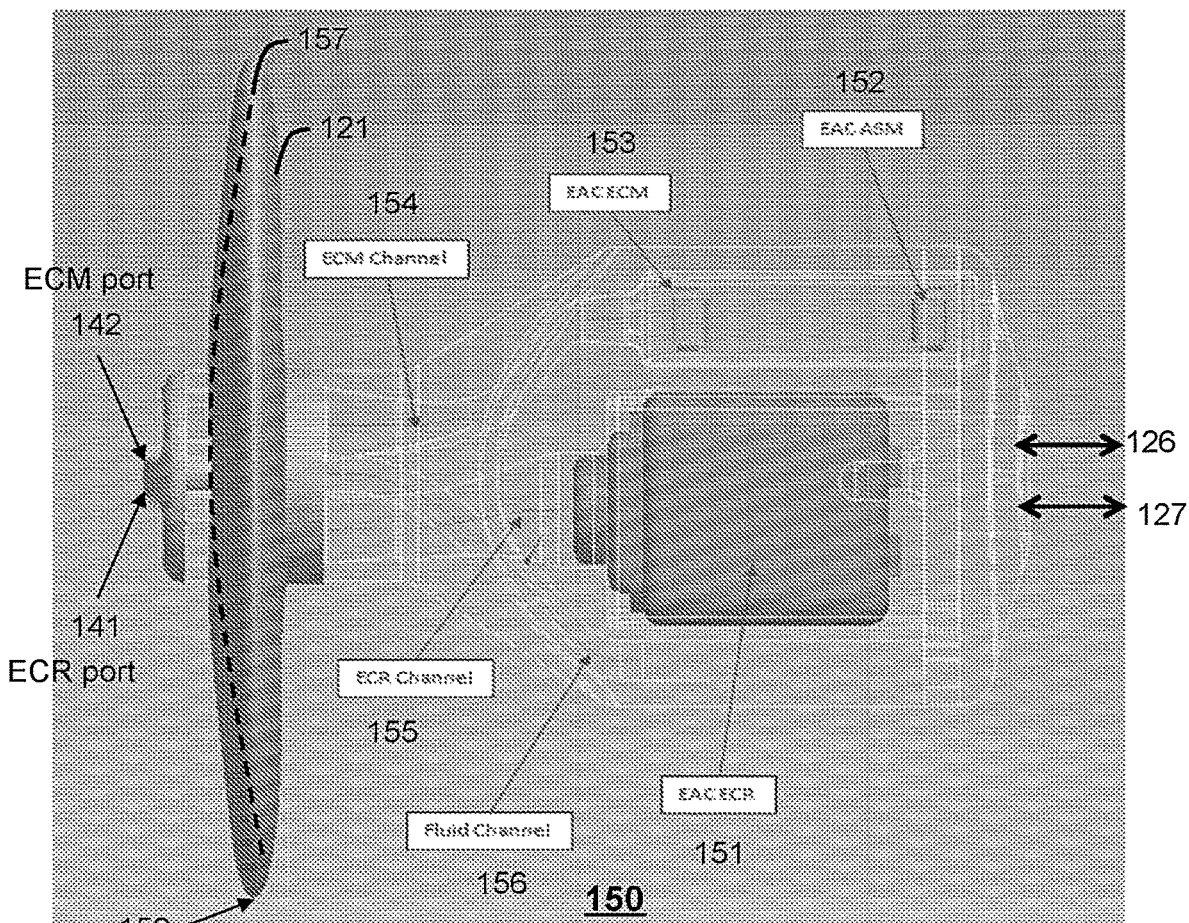
FIG. 1F is a schematic diagram of the electronic circuitry within the earpiece in accordance with one exemplary embodiment.
Figure 1G:
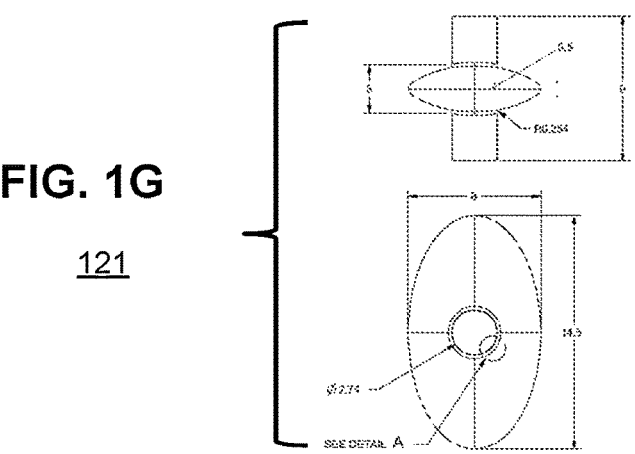
FIG. 1G is a side and top view of unique balloon geometry used with the earpiece or wireless wearable media accessory in accordance with an embodiment.

FIG. 1E is a perspective back view of the earpiece 120 in accordance with one exemplary embodiment. The earpiece 120 has also been shortened in length only for illustration purposes. The body portion 123 includes an Ambient Sound Microphone (ASM) port 143 for a microphone such as an ambient sound microphone 152 as shown in FIG. 1F. The port 143 is a hollow port which provides for passage of ambient sounds external the ear canal, for example, environmental sounds, such as background noises, conversations and other sound sources. The ASM port 143 also provides for "transparency" of acoustic sounds in the environment through the earpiece 120 by way of advanced audio signal processing, and for mixing of such ambient sounds with audio content delivered by the ECR when the ear canal is semi or fully occluded by the balloon 121 which has a narrow profile or thin edge 158. One example of advanced audio signal processing and mixing of ambient sounds with audio content is described in U.S. Patent Publication No. 2014/0093094 entitled "Method and Device for Personalized Voice Operated Control", published on Apr. 3, 2014 by the Assignee herein and hereby incorporated by reference. Notably, more than two lumens are also contemplated in certain embodiments, for example, to provide for passage between other structures or containers within the BTE module for providing other capabilities. Again, the first lumen 126 and second lumen 127 may be present as previously shown in FIG. 1C.

FIG. 1F is a schematic diagram of the electronic circuitry within an earpiece 150 in accordance with one exemplary embodiment. The electronic circuitry includes, but is not limited to, an Ear Canal Receiver (ECR) 151, an Ambient Sound Microphone (ASM) 152, and an optional Ear Canal Microphone (ECM) 153. The Ambient Sound Microphone (ASM) 152 captures ambient sound as previously described. The Ear Canal Receiver (ECR) 151 delivers audio content and optionally audible messages to the ear canal. The ECR channel 155 interfaces to the ECR port 141 previously described for passage of acoustic signals. The Ear Canal Microphone (ECM) 153 can be configured to capture an internal spoken voice and measure sound pressure levels. The ECM channel 154 interfaces to the ECM port 142 previously described for passage of acoustic signals. In some embodiments, the earpiece 150 can be a self-contained earpiece device that further includes a power source to power the electronic circuitry within the earpiece 150 (see FIG. 6O, for example). In some embodiments, the balloon 121 can include or be filled with battery chemistry or a small battery can be placed within the earpiece 150. In some embodiments, the earpiece 150 can be powered externally. In yet other embodiments, a rechargeable battery can be internal to the earpiece 150 and optionally externally connected to a power source for powering the earpiece and recharging the rechargeable battery or batteries within the earpiece 150. The balloon can be used as a bladder to fill with low to medium viscosity fluids that would allow the balloon envelope to be used and contain a battery chemistry which is very malleable. In some embodiments, the balloon can be used to not only power the earpiece, but it can optionally be remotely charged through proximity or inductive (either contact or contactless) methods.

In one embodiment, the battery cell technology used in conjunction with the balloons herein can include an electrochemical energy cell that has a galvanic cell including an anode electrode unit, a cathode electrode unit, an electrolyte body between the anode and cathode electrode units and contacting both the anode and cathode electrode units, and a separator layer including the electrolyte body and placed within the cell to contact both the anode and cathode electrode units to bring the anode and cathode electrode units in contact with the electrolyte body. The cathode electrode unit includes a cathode material including, for example, a powder mixture of a powder of hydrated ruthenium oxide and one or more additives. The anode electrode unit includes, for example, a structure formed of an oxidizable metal, and the separator layer includes a material that is porous to ions in liquid and is electrically non-conductive. A flexible electrochemical cell can be configured for a reduction-oxidation reaction to generate power at a surface of the electrode unit(s). See US Patent Application No. 2013/0089769, which is incorporated herein by reference.

The body portion 123 (shown in FIG. 1C) also includes passage for the first lumen 126 and the second lumen 127 when present. A processor in the BTE module 130 (in FIG. 1A) is operatively coupled to the ASM 152 and ECR through the bend sensor 110 by way of the electrical lumen 127. The processor in the BTE module 130 may also be operatively coupled to the ECM 153, if present, through the bend sensor 110 by way of the electrical lumen 127. Similarly, the fluid stored in the BTE module 130 can be transferred back and forth to the balloon 121 through the fluid channel 156 (of FIG. 1F) interfacing to the fluid lumen conduit 126 of the bend sensor 110 as previously described. A more detailed description of the earpiece assembly, in other embodiments, is discussed ahead in FIG. 7, and to which the reader is referred.

A distinguishing feature of the earpiece 120 and part of the electronic circuitry within the earpiece 120 shown in FIG. 1F is the biometric sensor 157, which in certain embodiments is integrated with the balloon 121. As one example, the biometric sensor can be a constructed material layer that in conjunction with the balloon senses changes in balloon size, pressure and shape depending on physiological states, for example, changes in ear canal size and shape, humidity, temperature and air properties. The biometric sensor 157 detects one or more biometric signals, alone or in combination with other sensors, for example, a pulse, a temperature, blood pressure, blood oxygenation, heart rate, respiratory rate, perspiration, humidity and acceleration. The biometric sensor layer can be material, capacitive, resistive or optical coated.

Depending on the technology used, the biometric sensor 157 can be configured to measure pulse waves and Pulse Arrival Time in the interior of the ear and can simultaneously acquire a single channel Electrocardiogram (ECG), a dual wavelengths Photoplethysmogram (PPG), the pressure in both ears, the body core temperature, as well the subjects motion. The acquired measurement data can either be saved on local on-board memory or transmitted wireless via Bluetooth or other wireless protocol or wired via USB to a host PC for further analysis. In another embodiment, conductive patterns can be formed in or on the balloon surface to form a surface acoustic wave sensor that can be used in pulse oximetry measurements for example.

In some embodiments, the earpiece can include a sensor for measuring bioimpedance or a bioimpedance characteristic as a wearable sensor that passively recognizes people. Such a sensor uses the unique electrical properties of a person's body to recognize their identity. More specifically, the sensor uses bioimpedance—a measure of how the body's tissues oppose a tiny applied alternating current—and learns how a person's body uniquely responds to alternating current of different frequencies. One study shows that such a sensor can accurately recognize people in a household 90% of the time.

In one configuration, by way of the electrical lumen 127 (shown in FIG. 1C, 1E or 1F), the biometric signal is communicated to the BTE module 130 (in FIG. 1A) to store on a local memory at least a parameter of the biometric signal, for example, a pulse rate, a humidity level, a blood oxygen saturation level, or other measured characteristic of the human physiology captured and identifiable within the ear canal. Similarly, the earpiece 120 can also transmit the at least one parameter of the biometric signal to a connected device, for example, a medical device within proximity and communicatively coupled thereto by way of a transceiver on the BTE module 130, for example, over a Bluetooth or Wi-fi connection. The earpiece 120 can also provide an audible message to a wearer of the earpiece responsive to identifying a parameter of the biometric signal. For example, upon the biometric sensor 157 (in FIG. 1F) identifying a heart rate and a blood pressure exceeding a preset threshold, or other established indicator, the earpiece 120 can then present an audible notification to the wearer, for instance, a voice message warning the user of a rate change or increase of a biometric parameter above or below a predetermined threshold, and also providing indication of the biometric parameter.

Various types and configurations of a biometric sensor are herein contemplated. In one configuration, the biometric sensor layer is resistance based comprising two thin, electrically resistive layers separated by a small gap there between, such that applied pressure on the balloon causes the two layers to touch and become connected and lowering a resistance, where the earpiece monitors for a change in a resistance there between that detects the biometric signals. This can include for example, detection of articulation causing the jaw bone to move and compress the ear canal from spoken voice. In another configuration the biometric sensor layer is capacitive based comprising an insulating layer and an outer coating, such that a perturbation on the balloon results in a distortion of the balloon's electrostatic field, where the earpiece monitors for a change in an electrostatic field thereon that detects the biometric signals. In yet another configuration, the biometric sensor layer is optical based comprising an infrared transceiver and an optical coating, such that light impingement on the balloon results in a distortion of the balloon's light spectrum, for example, for pulse oximetry, where the earpiece monitors for a change in the light spectrum that detects the biometric signals. Some embodiments using optical sensing could include infrared LEDs or other LEDs as illustrated and further discussed with respect to FIG. 6A.

The balloon shape, size, material, contents, and placement within a conduit or tube such as an ear canal form some of the features or elements of the embodiments herein. The balloon is primarily discussed herein within the context of an ear canal, but note that the balloon can be used with any number of channels, tubes, or conduits that form part of the human anatomy or not. For example, the balloon contemplated herein can be used with vascular channels, ileal conduits, arteries, veins, nasal passages, sinus passages, tracheal passages, respiratory tracts, or pipes or other conduits used for plumbing, or transfer of fluids, liquids or gases.

Using extensive anthropomorphic studies in some embodiments relating to the ear canal, the balloon can be designed, for example, in two sizes to fit every human ear canal. In this regard, the shape of the balloon can be predefined to fit the geometry of the human ear canal and be designed to have comfort to have the smallest contact area in the ear canal. In contrast to other devices that attempt to seal the ear canal, the balloon is generally immune or impervious to the occlusion effect (disturbing reverberation in the sealed ear canal) no matter how or where the balloon is placed within the ear canal. Other devices attempt to place the sealing area as close as possible to the tympanic membrane to reduce the area causing reverberation due to the occlusion effect. The balloon mitigates or eliminates the occlusion effect whether the balloon is placed at a first bend or at a second bend of the ear canal or at any other location of the ear canal.

In some embodiments, the balloon is made with materials that minimize permeability and avoid leakage. In some embodiments, the fluid used within the balloon is biocompatible and has a vapor characteristic that does not leave much residue. In one embodiment, the fluid used can be Fluorinert™ Liquid FC-770 by 3M™, which is a nonconductive, thermally and chemically stable fluid with a wide liquid range (−125 to 95 degrees C.) for use in many low temperature heat transfer applications. FC-770 has thermal and chemical stability, a wide liquid range, a non-conductive characteristic, a narrow boiling range, and is bio-compatible. FC-770 is a fully fluorinated liquid whose viscosity and centipoise is less than water and is not combustible. FC-770 also has very quick evaporation qualities, and won't leave much in terms of residue. Other fluids having similar characteristics can also be used and other fluids having very different characteristics could also be used, particularly for different applications not involving human conduits.

The balloon may be configured to partially or fully occlude ear canal to provide various degrees of acoustic isolation (i.e., attenuation of one or more frequencies of ambient sound) at the tympanic membrane. The balloon filled with liquid can offer unprecedented attenuation that can be characterized and can form a control mass as further described in WIPO Publication WO2014/039026 by the assignee herein and hereby incorporated by reference in its entirety.

The material for the balloon in some embodiments can be partially made of polyurethane having a hardness in approximately the 80 Shore A range which makes the balloon very compliant or semi-compliant. The balloon can be made starting with an extrusion that is approximately 2.6 mils in diameter and having approximately a 1/10000 of an inch wall thickness. The balloon would be capable of being blown to a particular shape where the shape was developed based on the anthropomorphics of the ear canal. In some embodiments, the shape can be 11 mm in height by 7.7 mm in width. During placement in the ear canal, the balloon can be placed at the second bend of the ear canal, which has a belly in it. The belly of the second bend is bigger than the area before it (including the area of the first bend or the second bend). During inflation, the balloon opens up larger than the few millimeters prior to preceding the second bend during insertion (towards the tympanic membrane) such that the balloon is expanded and seeded in the proper orientation and provides an excellent fitting for occlusion and anchoring within the ear canal. The balloon can be designed to traverse the ear canal to the second bend so that it anchors well (but anchoring to the second bend may be unnecessary in many applications as discussed above and anchoring to the first bend would be sufficient). The balloon is then anchored and hard to pull out once the balloon is in the belly of the second bend after inflation. Control of the geometry of the balloon is done in a manner that the shape of the balloon emulates the ear canal at the second bend and drives the fit of the balloon. In other words, the balloon takes on the form factor of the canal and applies an equal amount of pressure around the second bend. Of course, the balloon can also be designed to anchor with the first bend as discussed above.

In some embodiments, the balloon is deliberately made with a narrow profile or thin at a radial edge since it would require more fluid if made wider and would further cause other detriments to the ear canal anatomy such as necrosis. The balloon has a very thin edge that forms a contact area that minimizes the number of nerves that come in contact with the balloon. Less physical dermis area is thereby affected using a thin edge on the balloon. The dimensions of the concha bowl (see FIG. 4B) governs the width of the balloon. The concha bowl is only so large and can only have so much fluid in it. Furthermore, the fluid within the balloon needs to migrate into the ear canal when inserted. There is a relationship or correlation between ear canal and a concha bowl and an external auditory canal.

In some embodiments, the balloon is semi-compliant (like an airbag in a car that is shaped) where the expansion characteristics of the balloon are controlled by controlling at least a width of the balloon. The volume of the concha bowl in some regards dictates the shape of the balloon. In some embodiments, the balloon is made of a semi-compliant material having less than 10% elongation under pressure of 2 atmospheres or less. Under normal circumstances the balloon will not change in volume by more than 10%.

When the balloon is not inflated, the balloon has less than 3 mm in diameter, which is about 25% less than the 5% (fifth percentile) of the smallest female ear canal. This sized balloon easily goes past the first and second bend of the ear canal if desired. In contrast, the use of rubber or foam in ear canals causes the rubber or foam to become trapped at the first bend, even when the foam or rubber is squeezed or rolled down. Rubber and foam has memory causing them to return to their original quiescent state. Foam and rubber are always in a state of expansion, which applies a force on the ear canal and causes headaches, TMJD, and other issues by the constant outward expansion of the force. Foam and rubber produces limited blood supply to the tissue causing tissue necrosis. Use of the balloon in accordance with the embodiments herein has a minimized contact force and contact area, which gives rise to less irritability, less nerve issues, and less of a presence in the ear canal.

Figure 2A:
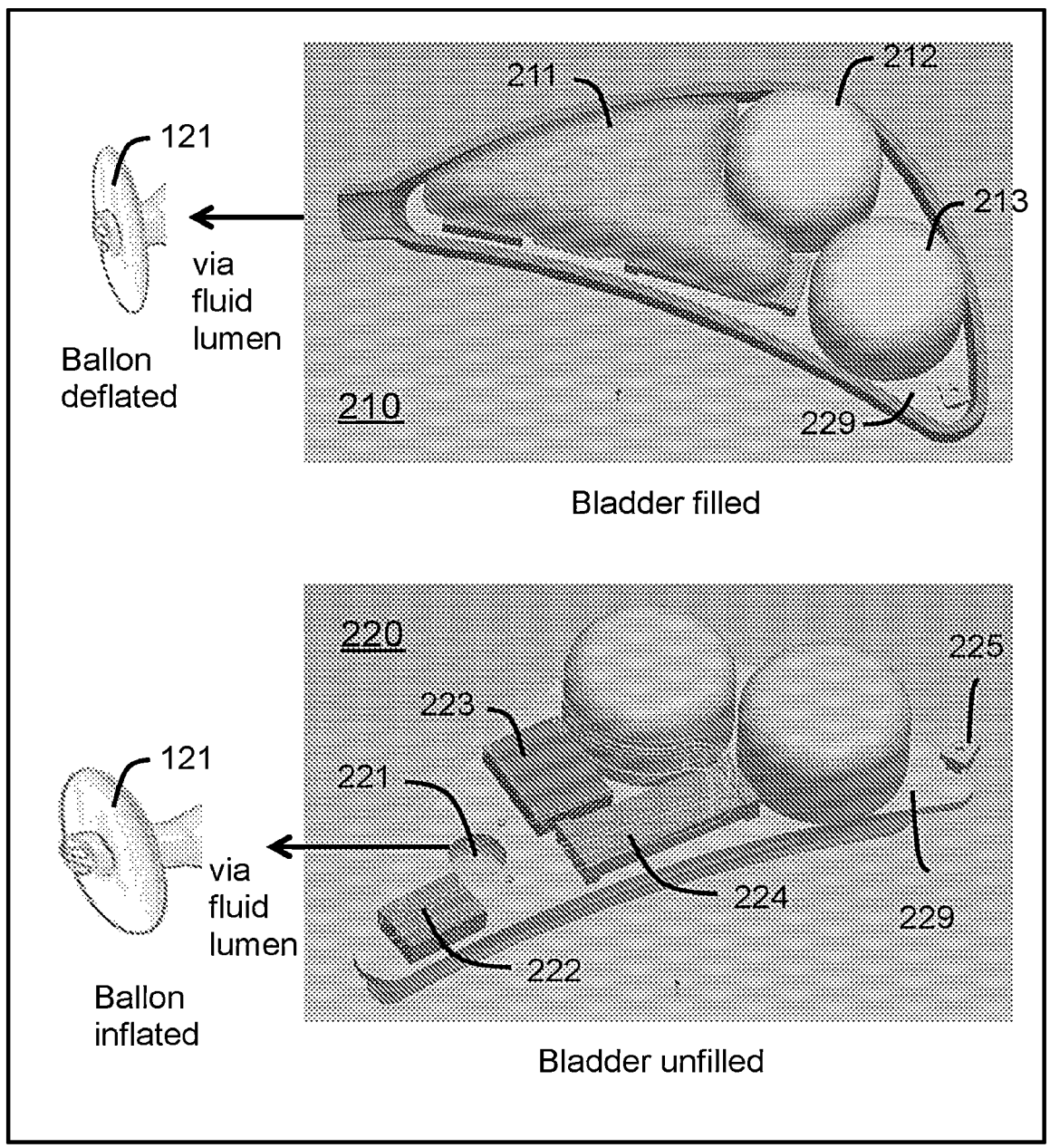
FIG. 2A is an illustration of a front side of a BTE module of a wearable media accessory device in accordance with one exemplary embodiment.

FIG. 2A is an illustration of a front side of the BTE module 130 in accordance with one exemplary embodiment. When worn, the front side rests against the back of the pinna and comfortably fits within the post articular groove (see FIG. 4G). As shown in subplot 210, the BTE Module 130 includes a bladder having a first volume 211 on the front side, a first reservoir 212, and a second reservoir 213 on a first (front) side of a printed circuit board (PCB) 229. In one arrangement, the reservoirs 212/213 are batteries, for example, small button cell batteries used in hearing aids (e.g., size 10; 100 mah) to provide power. Underneath the first volume 211 are electronic components. These can be seen better when the bladder is made transparent for illustration in subplot 220. As shown in subplot 220, the BTE Module shows a transceiver (e.g., Bluetooth low energy chip) 222, a memory chip (e.g., SDRAM) 223, and an antenna (2.5 GHz) 223 on a second (front) side of the PCB 229. Again, these components are on the same front side of the PCB 229, but underneath the first volume 211 of the bladder. A pass-through 221 permits for fluid exchange of the bladder between the front side and the back side as will be explained ahead.

The BTE module 130 may also include a behind-the-ear (BTE) Ambient Sound Microphone (ASM) 225. The BTE ASM 225 captures acoustic signals, the transceiver 222 receives and transmits audio signals to and from the earpiece 120, the memory 223 temporarily buffers the audio signals and the acoustic signals, and the first reservoir 212 and second reservoir 213 serve as a battery for supplying power to the ambient sound microphone, the transceiver and the memory. It should be noted that the components although located as shown for optimal placement, can also be arranged in other configurations or in more or less than the number of PCB layers shown without departing from the scope of the embodiments.

Another feature of the earpiece 120 is a utility of the balloon as a bladder to support battery chemistry. In this arrangement, the first reservoir 212 is a first chamber to store a first bio-compatible battery liquid for the bladder 211, for example, a negative ion fluid. The second reservoir 213 is a second chamber to store a second bio-compatible battery liquid for the bladder 211, for example, a positive ion fluid. In this arrangement, the bio-compatible battery liquid in the bladder is shared between the reservoirs 212/213 and the bladder 211, whereby power is generated for the BTE module responsive to electrolysis, for instance, by creating an electrochemical gradient (voltage) between the first 212 and second 213 bio-compatible battery liquid to power the electronic circuitry. Other fluid types may also be considered here without departing from the scope of the invention. If the arrangement is not being used with human conduits, then there is less of a need for a bio-compatible battery liquid and thus a wider range of fluids (such as alkalines) can likely be used to support a battery in this manner.

Figure 2B:
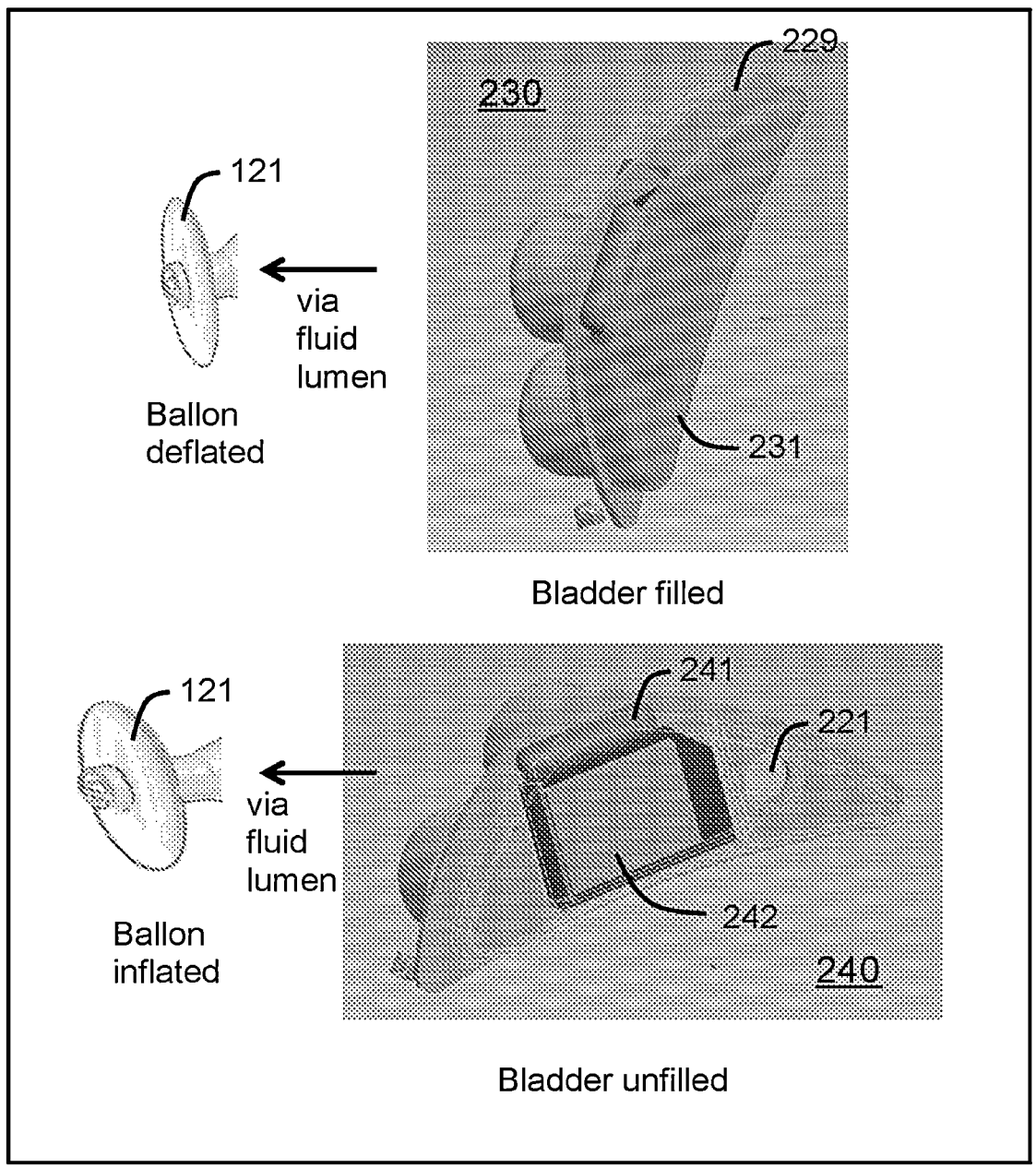
FIG. 2B is an illustration of a back side of a BTE module of the wearable media accessory device in accordance with one exemplary embodiment.

FIG. 2B is a perspective illustration of a back side of the BTE module in accordance with one exemplary embodiment. As shown in subplot 230, the BTE Module includes the bladder, which as previously noted, occupies a second volume 231 on the back side of the PCB 229. In this configuration, the second volume 231 of the bladder intentionally occupies most of the space on the back side. Similarly to the front side, underneath the second volume 231, are other electrical components of the BTE module 130, which can be seen better when the bladder is made transparent for illustration. As shown in subplot 240 of FIG. 2B, the BTE module includes a compartment 242 which can store; for example, a water based dispersion of a spherical, micronized partially saponified Montan wax (e.g., WM 8220).

Figure 2C:
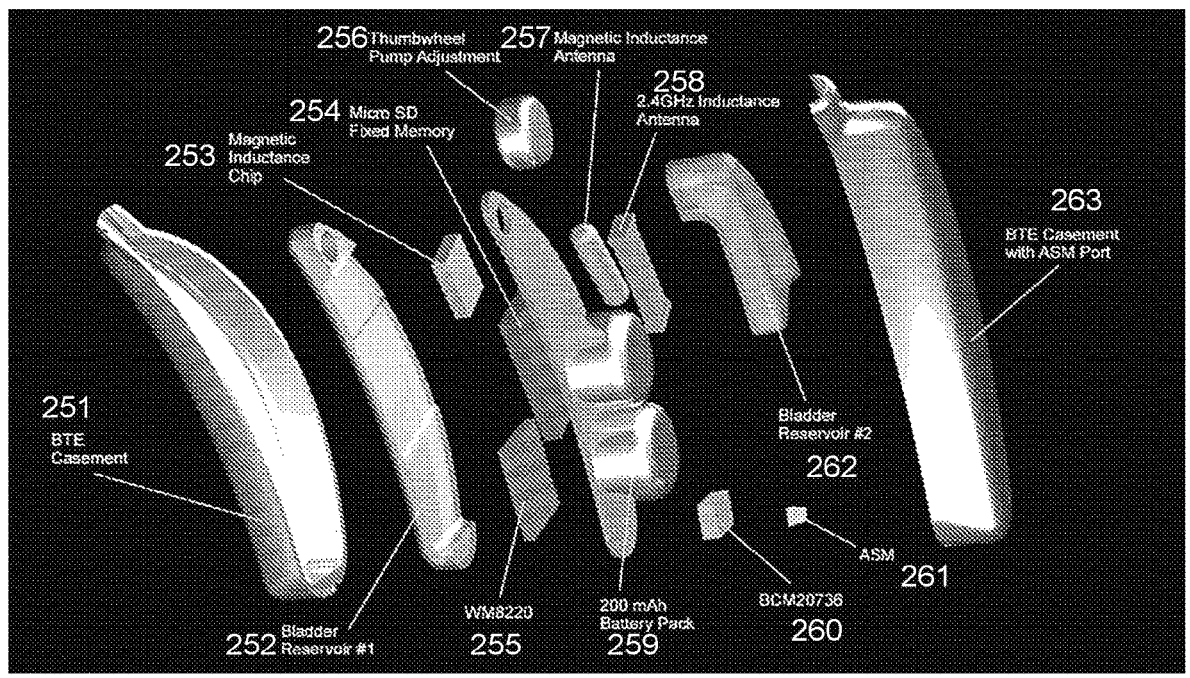
FIG. 2C is an exploded view of the BTE module in accordance with one exemplary embodiment.

FIG. 2C is an exploded view of yet another BTE module 250 in accordance with the embodiments. The BTE module 250 includes a number of components encased within a rear BTE casement or cover 251 and a front casement or cover 263. The front casement 263 can include an ambient sound microphone (ASM) port enabling exposure to the environment for an ASM 261. Many of the components included in BTE module 250 operate similar to the embodiment of FIGS. 2A and 2B. The BTE module 250 includes a first bladder reservoir 252, a magnetic inductance chip 253, a wax dispersion module 255 (WM 8220), a micro SD memory card 254, a thumbwheel pump adjustment module 256, a magnetic inductance antenna 256, a 2.4 GHz inductance antenna 258, a 200 mAh battery pack 259, a Bluetooth module 260, a second bladder reservoir 262 as well as the ASM 261. The magnetic inductance chip 253 and magnetic inductance antenna 257 or 2.4 GHz inductance antenna can be used for short range or near field communication. The thumbwheel pump adjustment 256 provides an alternative method of moving fluid between different chambers or reservoirs in the BTE module 250 and a balloon (such as balloon 121 shown in FIG. 1C) that resides external to the BTE module. As an alternative to the various antennas, a single antenna could be designed that allows for Bluetooth and RF transmissions and additionally provide proximity charging via a wireless charger. In yet another alternative, a single chip can include and combine all or some of the functions of processing Bluetooth and RF signaling, DSP functions, 802.11 functions, power recharging functions, and biometrics monitoring functions.

Figure 2D:
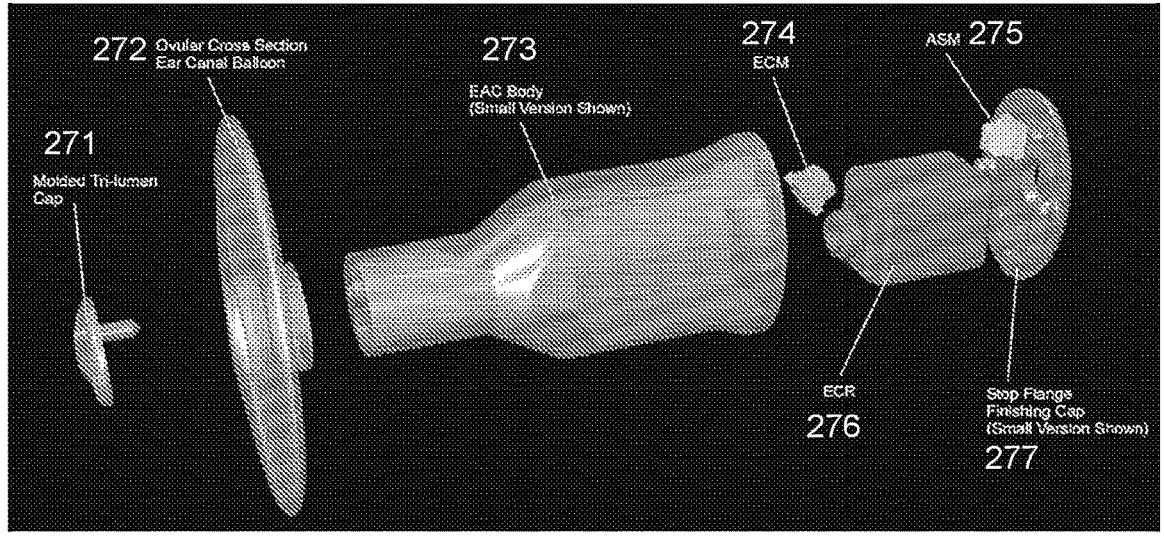
FIG. 2D is an exploded view of the earpiece in accordance with one exemplary embodiment.

FIG. 2D is an exploded view of another earpiece 270 in accordance with the embodiments. The earpiece 270 comprises at a distal end (the end inserted into the ear canal) a molded tri-lumen cap 271 used to retain a balloon 272 (such as an ovular cross sectional ear canal balloon) up against a distal end of an external auditory canal (EAC) body 273. The EAC body 273 can be made of a low durometer liquid injection molded silicone, but can be made of other materials such as thermoplastic elastomers, thermoplastic polyurethanes or other elastomeric biocompatible materials. In one embodiment, the material used can have a durometer range of 15-20 Shore A. The EAC body 273 can hold or enclose an ear canal microphone 274 and an ear canal receiver (speaker) 276 that is inserted and retained within a proximal end of the EAC body 273 using a stop flange finishing cap 277. The EAC body 273 (as well as some of the other external components) should be made of flexible, soft, low durometer materials that will not swell (hydrophobic). The EAC body 273 and other housing components need to traverse a tortuous or spiral-like ear canal during insertion of the earpiece and thus should be flexible and malleable.

Figure 2E:
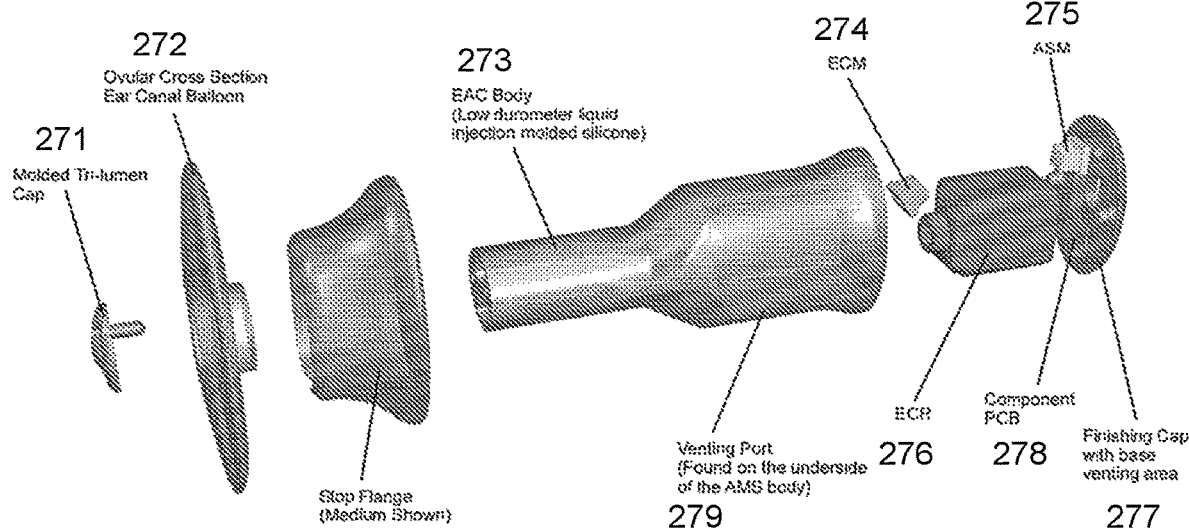
FIG. 2E is an exploded view of the earpiece in accordance with another exemplary embodiment.

FIG. 2E is an exploded view of yet another earpiece 280 similar to earpiece 270 of FIG. 2D and in accordance with the embodiments. The earpiece 280 comprises at a distal end a molded tri-lumen cap 271 used to retain a balloon 272 and a stop flange 278 up against a distal end of an external auditory canal (EAC) body 273. The stop flange 278 can be made of similar materials as the EAC body since it will also need to be flexible and malleable. The EAC body 273 can be made of a low durometer liquid injection molded silicone. The EAC body 273 can include a venting port 279. The EAC body 273 can hold or enclose an ear canal microphone 274, an ear canal receiver (speaker) 276, and printed circuit board component 278 that is inserted and retained within a proximal end of the EAC body 273 using a stop flange finishing cap 277. The stop flange finishing cap 277 can also include a venting port (not shown). The stop flange 278 and/or stop flange finishing cap 277 can be made of a translucent material so that the skin that it covers when the earpiece is inserted in the ear canal essentially shows through the translucent materials. Thus, the translucent material contributes to the overall device being "invisible" to outside observers.

Figure 2F:
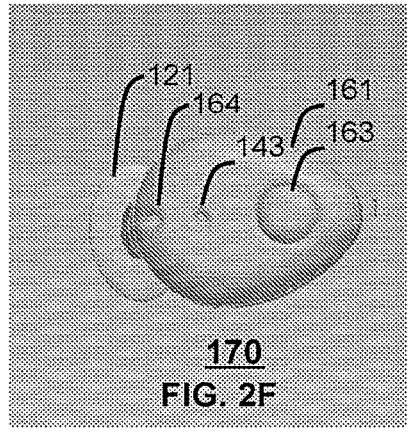
FIGS. 2F-2J illustrate various views of an alternative earpiece in accordance with an embodiment.
Figure 2G:
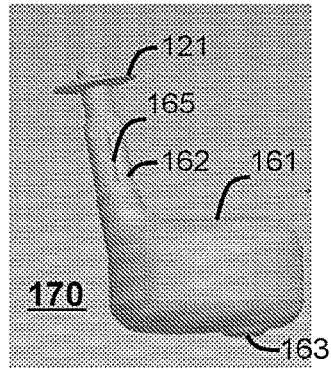
Figure 2H:
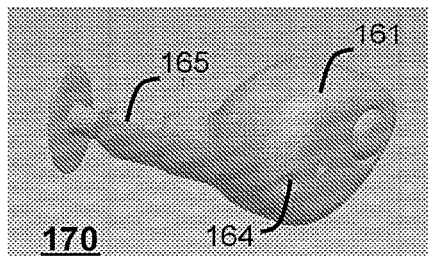
Figure 2I:
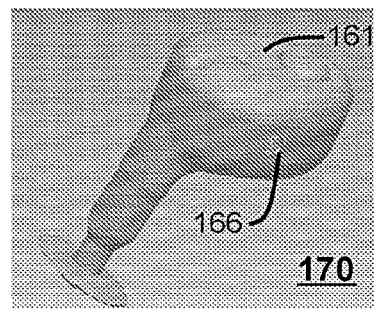
Figure 2J:
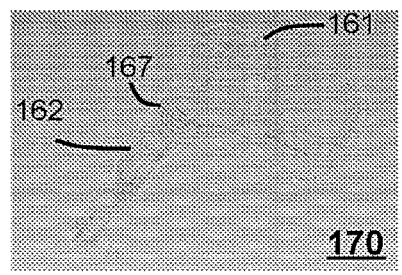
Figure 2K:
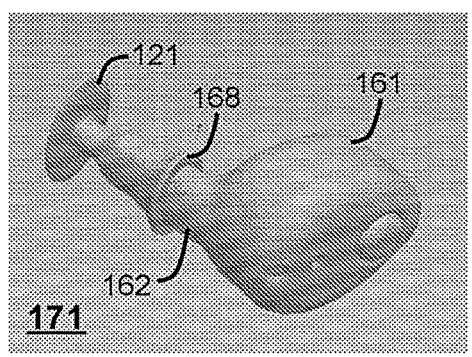
FIG. 2K illustrates a perspective view of an earpiece with a small flange in accordance with an embodiment.
Figure 2L:
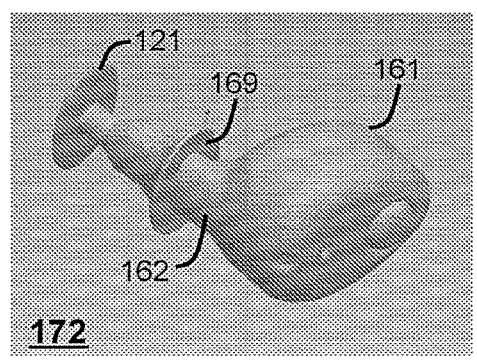
FIG. 2L illustrates a perspective view of an earpiece with a larger sized flange in accordance with an embodiment.

FIGS. 2F-2L illustrate several plan views of other embodiments that do not include a BTE module and is instead an in-concha embodiment of a wearable media accessory 170. FIGS. 2F, 2G, 2H, and 2I illustrate respective front plan, top plan, and side perspective views of the wearable media accessory 170 having a balloon 121 (similar to the previous embodiments above) coupled to a main earpiece portion 161 via an extension 162 (shown in FIG. 2G). The main earpiece portion 161 includes an ambient sound microphone port 143 (similar to previous embodiments above) and a push button interface 163 for expanding the balloon 121 using a pump that would force fluid from a reservoir or other chambers or conduits within the wearable media accessory 170 towards the balloon 121. FIGS. 2F and 2H also depict a venting port 164. FIG. 2G is a top plan view and FIG. 2H is a top perspective view of the accessory 170 illustrating a venting slot 165 and the venting port 164 which are aligned to protect against the occlusion effect within the earpiece 161 and extension portion 162. FIG. 2I is a bottom perspective view further depicting a magnetic connector interface 166 on the bottom on the main earpiece portion. Although the accessory 170 is primarily intended to be wireless, the magnetic connector 166 enables the accessory to optionally have a wired connection for any of power, control signals, or data, audio or content signaling and synching. The magnetic connector 166 can connect the accessory 170 to a BTE module or alternatively to a smart phone, tablet, laptop or desktop computer for example. The magnetic connector 166 can also be used to directly connect a left earpiece with a corresponding right earpiece (see FIG. 6M). FIG. 2J illustrates an internal view of the accessory 170 having an internal pump or a mini-valve 167 positioned between the extension 162 and main earpiece portion 161. In other words, the mini-valve or pump 167 is strategically placed at the orifice and the neck of the in-concha device. FIG. 2K is another top perspective view of yet another wearable media accessory 171 very similar to the accessory 170. The accessory further includes a stop flange 168 of medium size on the area of the extension 162 between the main earpiece section 161 and the balloon 121. FIG. 2L is another top perspective view of yet another wearable media accessory 172 very similar to the accessory 172 except the accessory includes a stop flange 169 of a larger size on the area of the extension 162 between the main earpiece section 161 and the balloon 121. The variable sized stop flange section (168 or 169) are designed to fit between the 5% and the 95% ($5^{th}$ and $95^{th}$ percentile) geometry of human ear canals.

In some embodiments the BTE module is designed to be hidden or invisible to an outside observer by placing the BTE module behind the pinna. In some embodiments, the functions in the BTE module are incorporated into the earpiece and the earpiece in designed to be placed within the ear canal or partially within the ear canal and concha bowl.

FIGS. 2M-2V is a series of see-through side perspective views that selectively highlight various components of the wearable media accessory 172. As in FIG. 2L, the accessory 172 in FIG. 2M illustrate the main earpiece portion 161, the stop flange section 169, and balloon 121. FIG. 2M further illustrates the venting port 164 and the optional venting port 164a within the stop flange section 169. FIG. 2N further illustrates a bladder portion or battery 191 and FIG. 2O illustrates a bladder portion or battery 192. FIG. 2P illustrates an ear canal receiver (speaker) 193 and an ear canal microphone 194. FIG. 2Q highlights the push button interface 163 while FIG. 2R highlights the various antenna or antennas 195 used for RF, Bluetooth, or 802.11. FIG. 2S highlights an inductive antenna 196 used for inductive charging or alternatively for near field transfer of information. FIG. 2T highlights the mini-pump or valve 167 while FIG. 2U highlights the balloon 121. FIG. 2V highlights yet another reservoir 197 that can be used with the wearable media accessory 172.

Figure 2W:
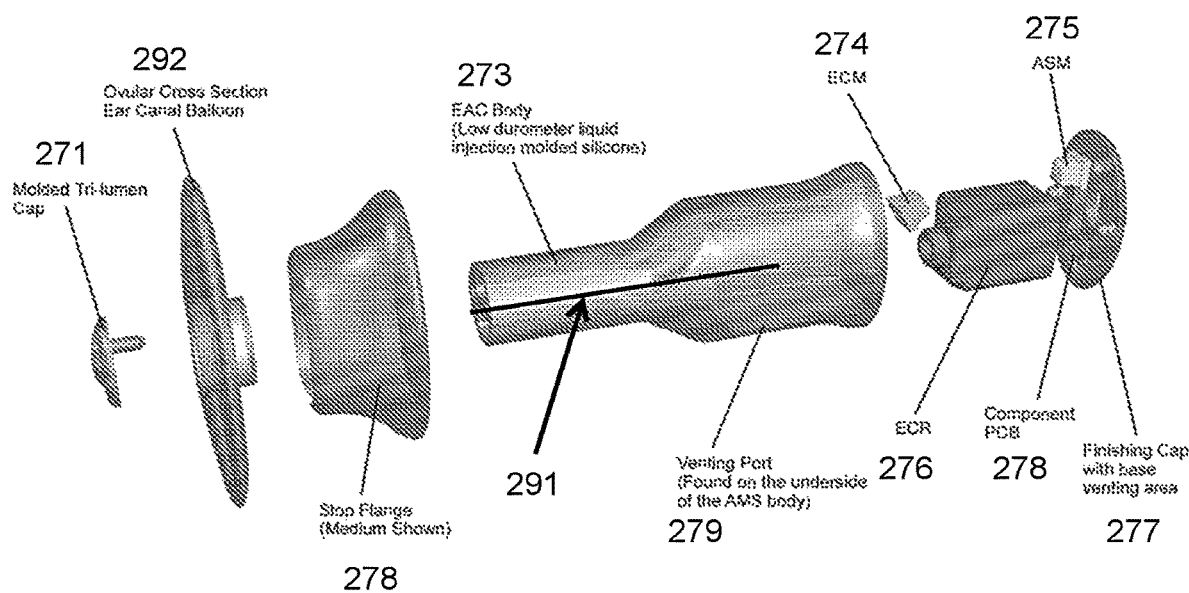
FIG. 2W illustrates an exploded view of another earpiece in accordance with an exemplary embodiment.

FIG. 2W illustrates an exploded view of yet another earpiece 290 in accordance with the embodiments. The earpiece 290 comprises at a distal end (the end inserted into the ear canal) a molded tri-lumen cap 271 used to retain a balloon 292 (such as an ovular cross sectional ear canal balloon), and a stop flange 278 up against a distal end of an external auditory canal (EAC) body 273. The EAC body 273 can include a venting port 279. The EAC body 273 can be made of a low durometer liquid injection molded silicone. The EAC body 273 can hold or enclose an ear canal microphone 274 and an ear canal receiver (speaker) 276, and printed circuit board component 278 that is inserted and retained within a proximal end of the EAC body 273 using a stop flange finishing cap 277. The stop flange finishing cap 277 can also include a venting port (not shown). The earpiece 290 can further include an antenna 291 used for RF, Bluetooth, and/or magnetic induction.

Figure 2X:
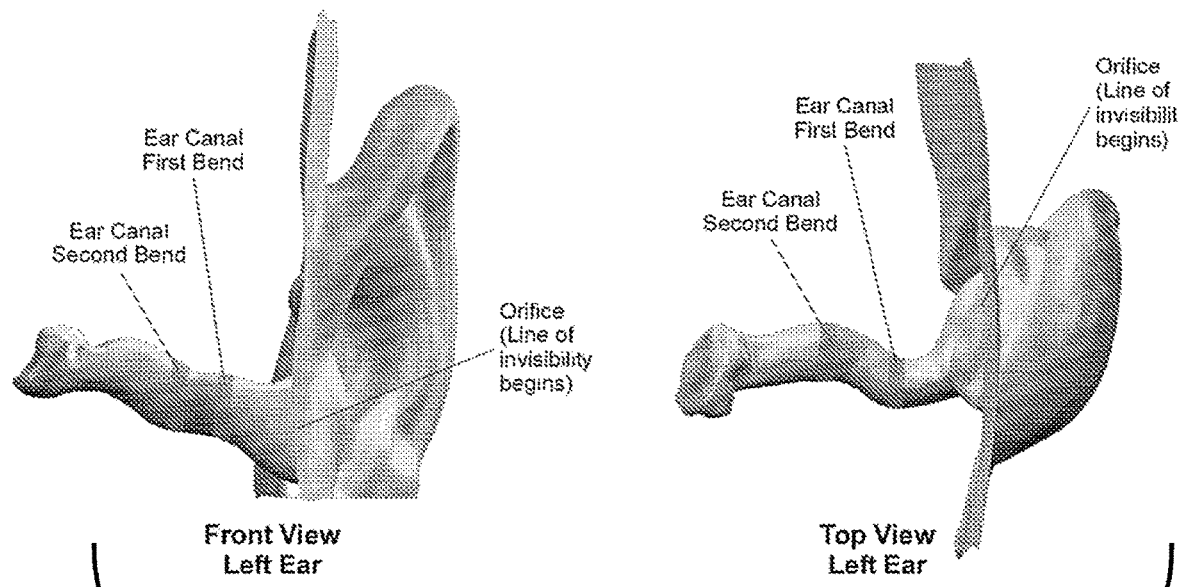
FIG. 2X illustrates a front view and a top view of the anatomy of a left ear and left ear canal.

FIG. 2X illustrates a front view of a left ear and ear canal and a corresponding top view of the left ear and ear canal. The illustrations highlight anatomical points of interest that interface with the various embodiments described herein including an orifice where a line of invisibility begins as well as the first bend of the ear canal and the second bend of the ear canal.

Figure 2Y:
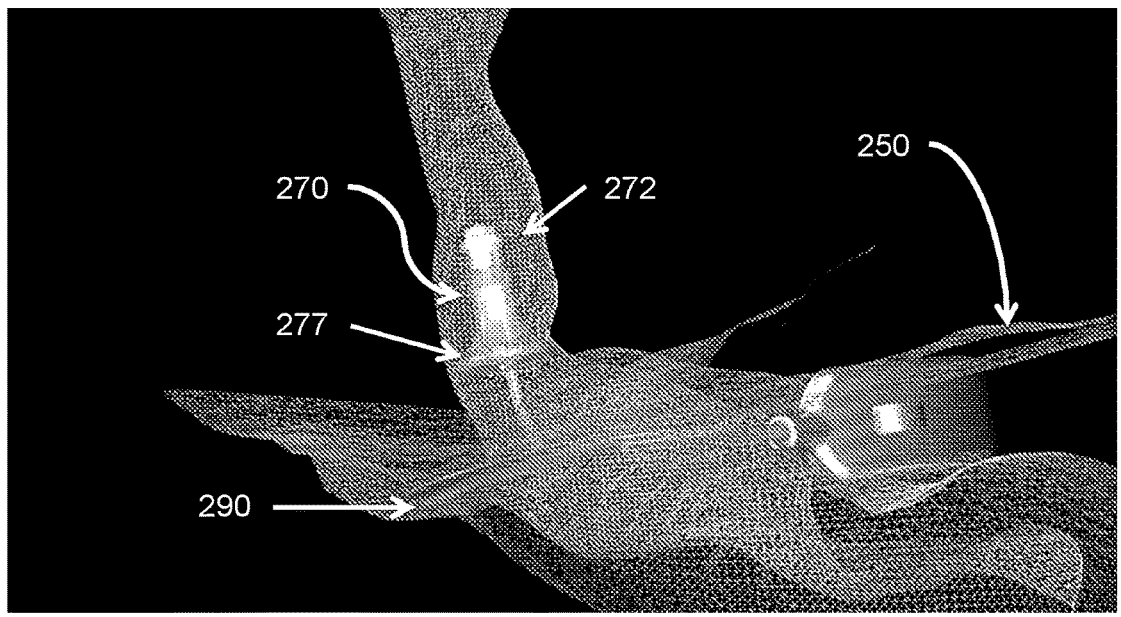
FIG. 2Y illustrates the placement of the earpiece within the second bend of the ear canal in accordance with an embodiment herein.

FIG. 2Y depicts an internal top view of a wearable media accessory system 295 inserted into a left ear before inflation of a balloon 272. As shown, the earpiece 270 is inserted into the ear where the balloon 272 goes just beyond a second bend of the ear canal and the stop flange 277 of the earpiece 270 stops at the (first) bend of the ear canal. The BTE module 250 is placed behind the ear (or more particularly the pinna of the ear) and can be coupled to the earpiece 270 via the smart tube 290.

Figure 4G:
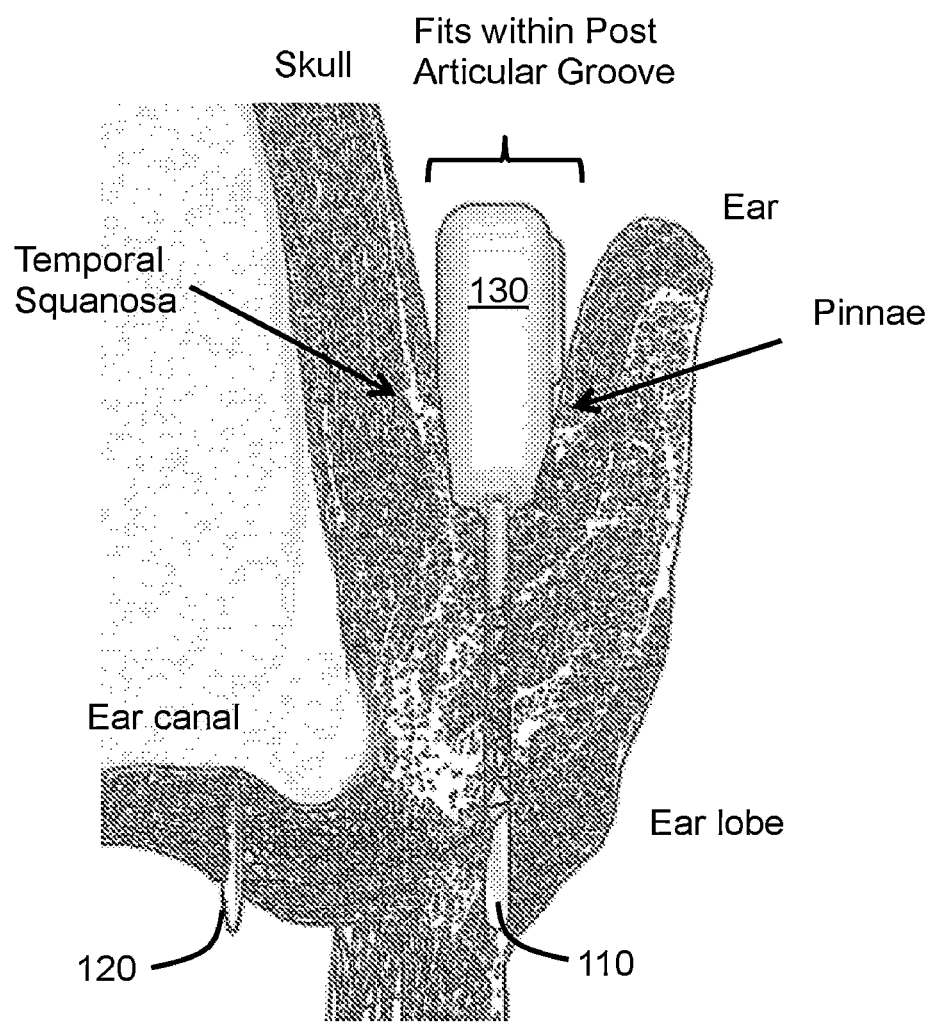
Figure 4H:
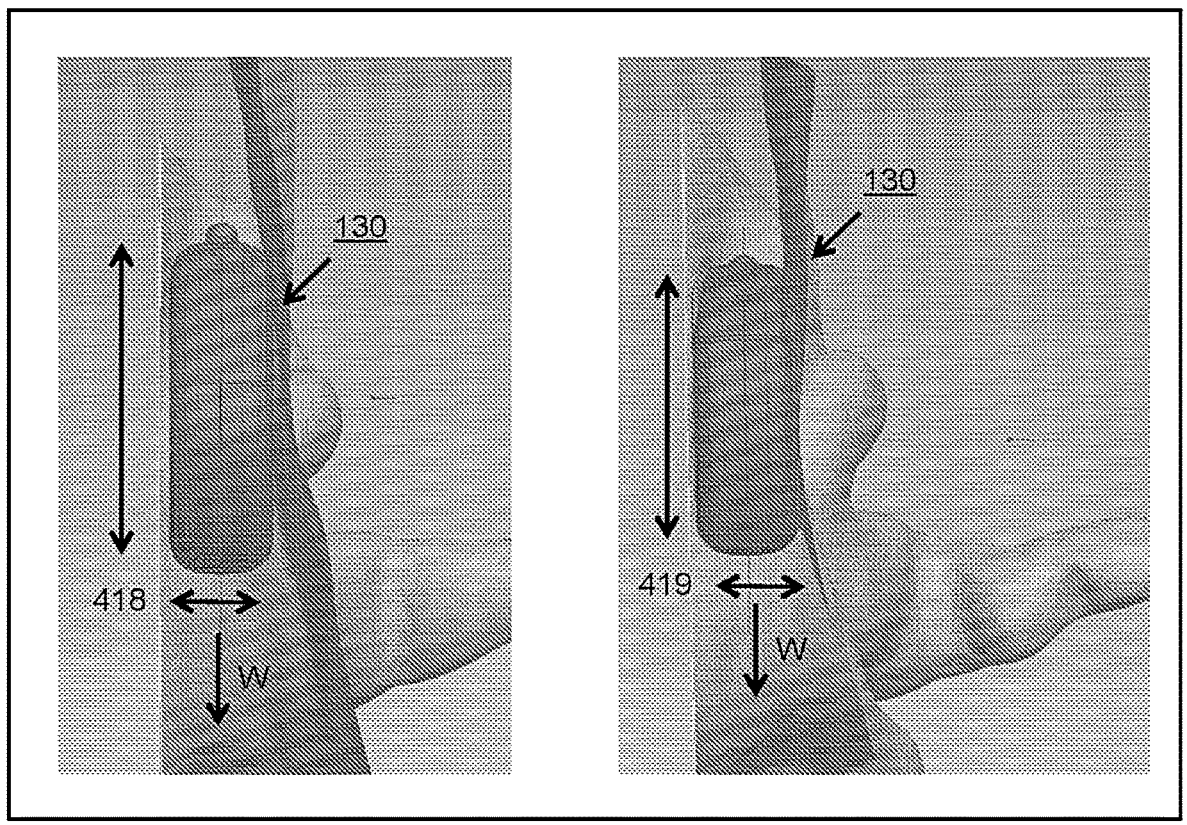
FIG. 4H illustrates an anatomy of the human ear for study of an ergonomic and comfortable behind the ear component along the back of the ear.
Figure 4I:
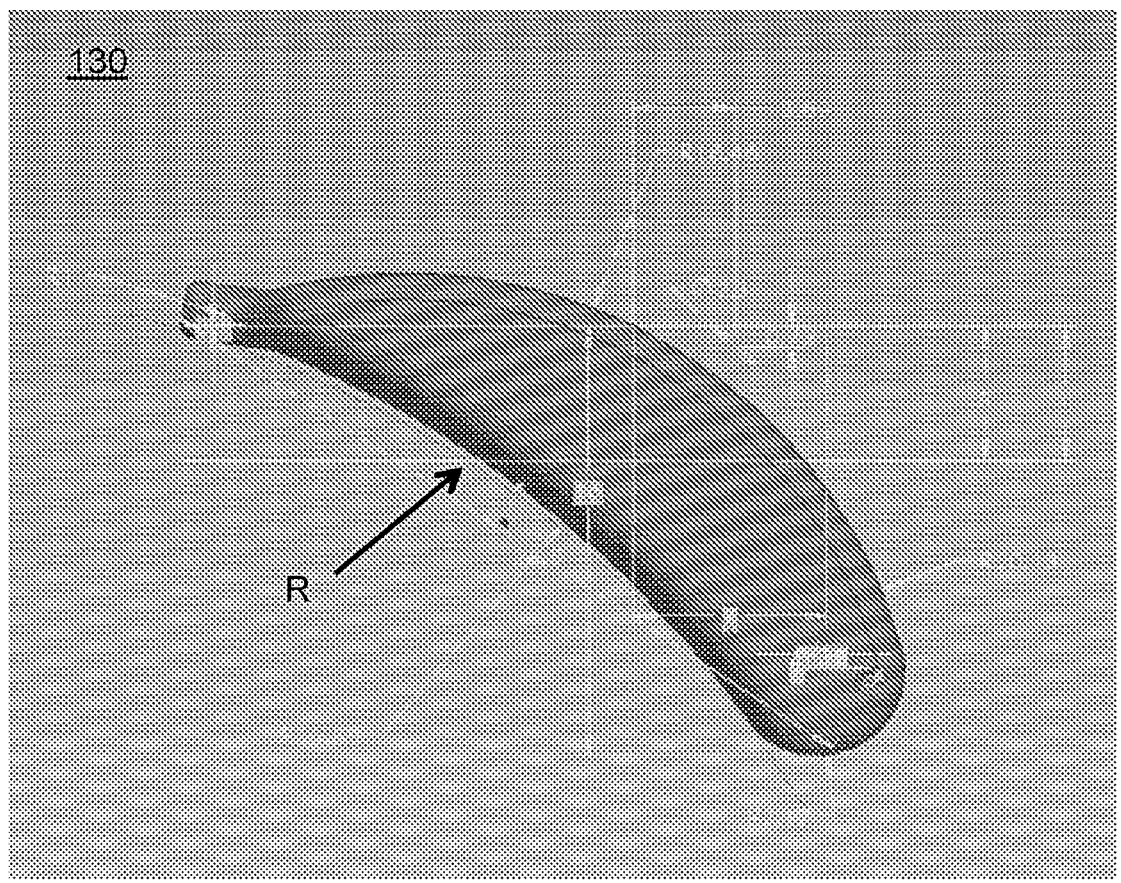
FIG. 4I depicts a diagrammatic illustration of a radius function for the BTE module in accordance with one exemplary embodiment.
Figure 4J:
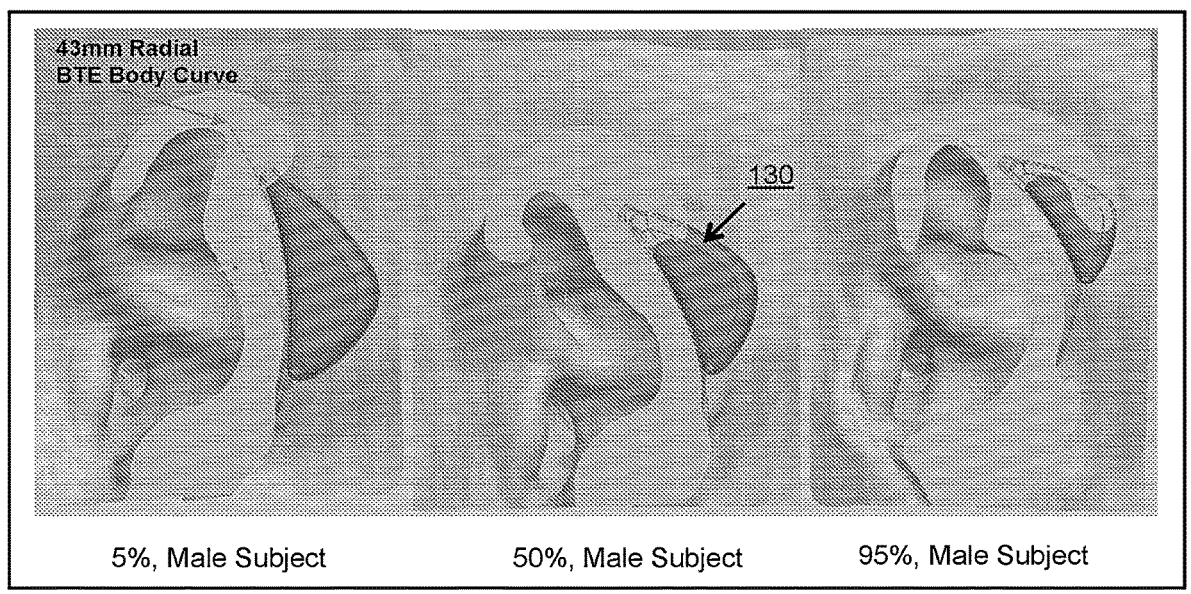
FIG. 4J illustrates a best fit, curve and shape of a wireless behind the ear media device accessory from study of a ears in a male population in accordance with one exemplary embodiment.
Figure 4K:
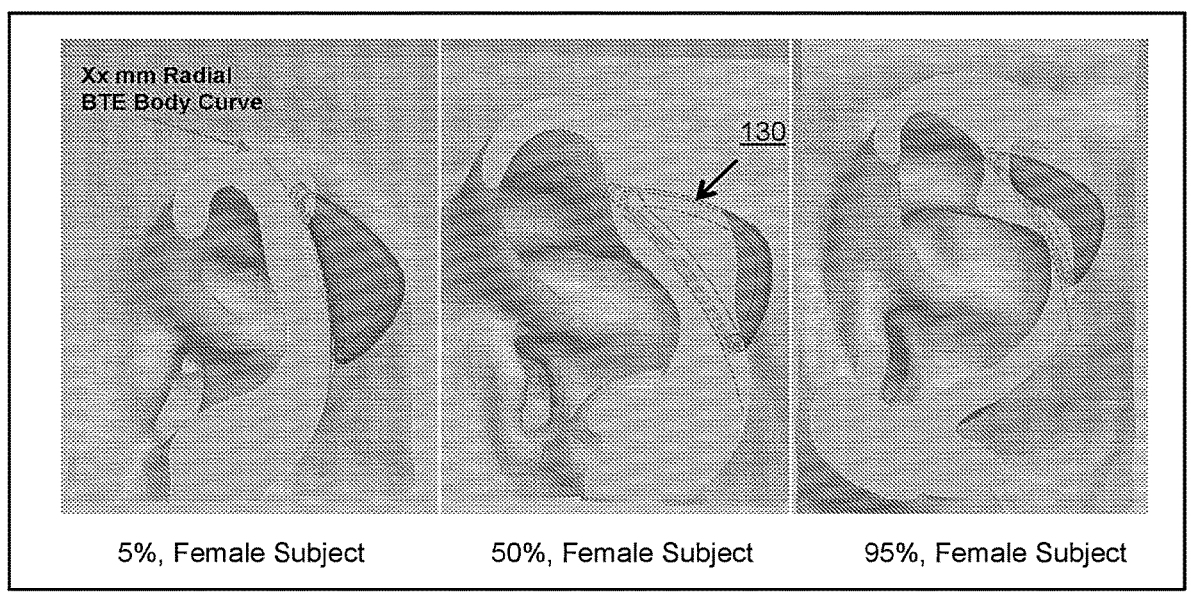
FIG. 4K illustrates a best fit, curve and shape of a wireless behind the ear media device accessory from study of a ears in a female population in accordance with one exemplary embodiment.
Figure 4S:
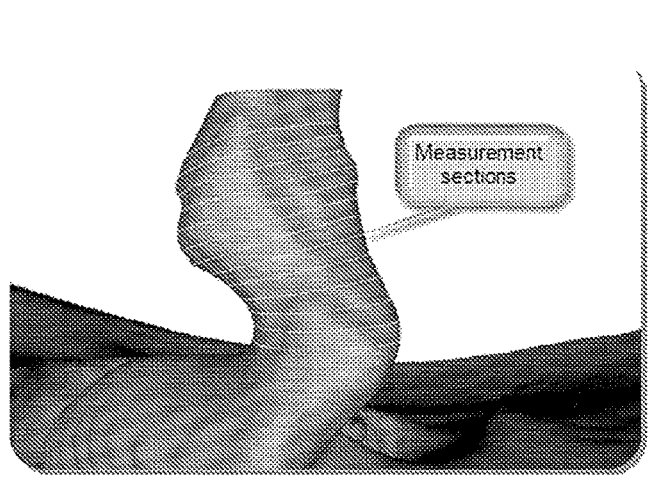
FIG. 4S illustrates a ear canal and various sections.
Figure 4T:
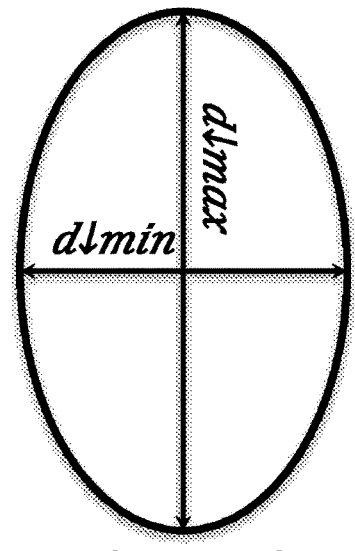
FIG. 4T illustrates the diameter configuration at the first bend of the ear canal.
Figure 4U:
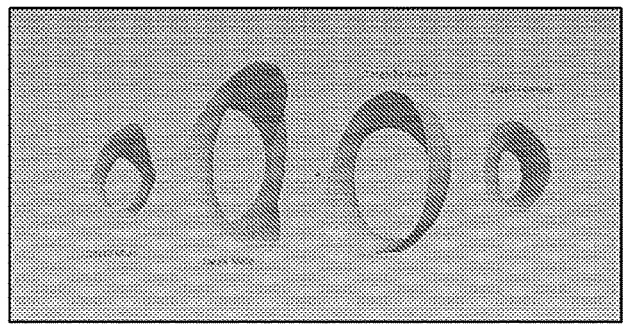
FIG. 4U illustrates the various opening or orifice size ranges for the ear canal for large and small males and females.

Briefly, as shown in FIG. 4G, the back side of the BTE module (such as BTE module 130) rests against the skull with a shape designed to accommodate the temporal squanosa anatomical landmark and comfortably fits within the post articular groove. The volume distribution of the bladder and BTE module shape was designed to accommodate a preferred weight to width and length relation of the ear anatomy for best fit, and with regards to balance and position as shown in FIGS. 4J-4K. Although the bladder is partitioned on both sides of the PCB 229 (see FIGS. 2A and 2B) to specific volumes within the BTE module as illustrated, there are other embodiments where the bladder may be partitioned to different volumes or shapes or even occupy only one side of the PCB 229. The bladder 211, which by way of the first volume and second volume can hold upwards of 0.145 (cc)+0.149 (cc) when split between the first side and second side PCB 229 by way of the pass through (bladder feed through) 221, which permits for fluid exchange between the two sides. Moreover, the bladder 211 responsive to a user directive transfers the fluid to the balloon 121 on the earpiece, for example, responsive to touch based user interface gestures on the bend sensor 110, as described next.

Figure 3A:
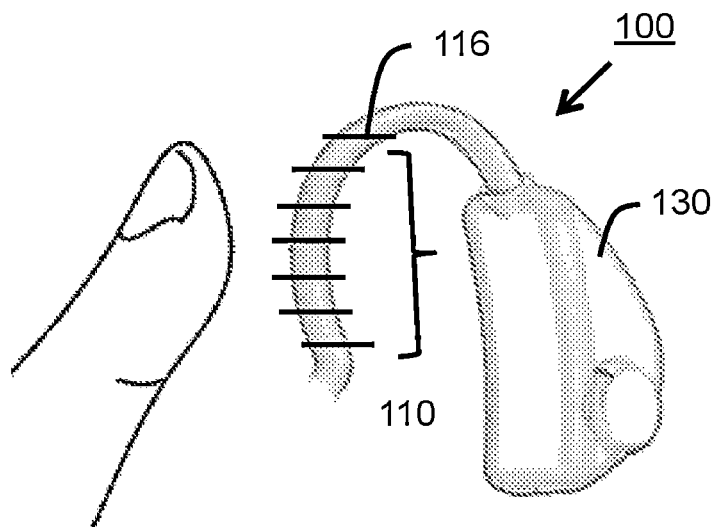
FIG. 3A is an illustration for a user interface control of the wireless wearable media accessory in accordance with one exemplary embodiment.
Figure 3B:
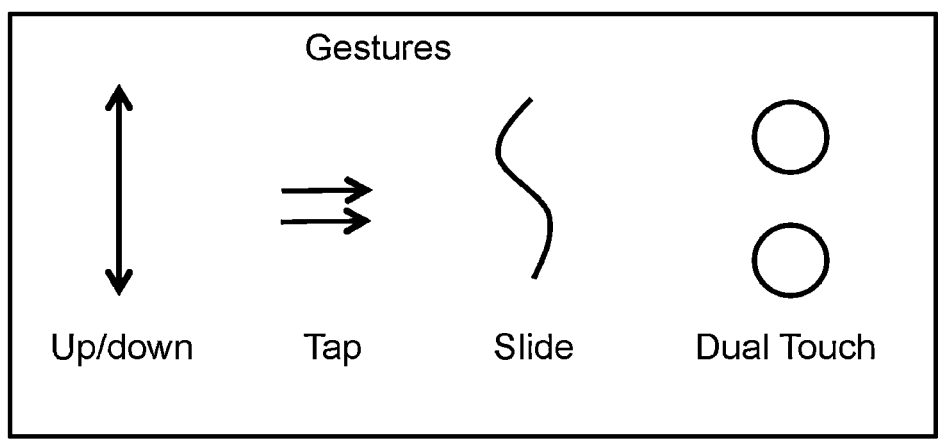
FIG. 3B illustrates an exemplary set of gestures for user interface control of the wireless wearable media accessory in accordance with one exemplary embodiment.

FIG. 3A is an illustration of user interface control of the wearable media accessory device 100 in accordance with one exemplary embodiment. As illustrated, a user can touch the bend sensor 110, which includes thereon a smart skin surface to control a function of the earpiece, for example, a volume control, media control, directional control, mute control, recording, and phone control of the earpiece. The bend sensor can also be designed to control the displacement of fluid to or from reservoir(s) within the BTE 130 and to or from a balloon on an earpiece (not shown in FIG. 3A, but see FIG. 2D or 2E for example). Of course, the bend sensor 110 can also be configured to control any number of other functions. FIG. 3B illustrates an exemplary set of gestures, which the bend sensor 110 identifies for gesture control of one or more functions; an up/down movement of the finger, a tapping of the finger, a sliding motion, a pinch and a dual finger touch of the smart skin. Any one of these gestures, alone or in combination can serve to adjust or control a function of the earpiece. As one example, the user can perform an up gesture to increase a volume, and a down gesture to decrease the volume. It should also be noted that the earpiece and bend sensor can work in conjunction with voice control, for example, upon the user saying 'volume', the smart skin surface will be responsive to touch for adjusting a volume. Similarly, if the user says 'messages', the smart skin surface will be responsive to scrolling a message list for audible playing a selected message.

Figure 3C:
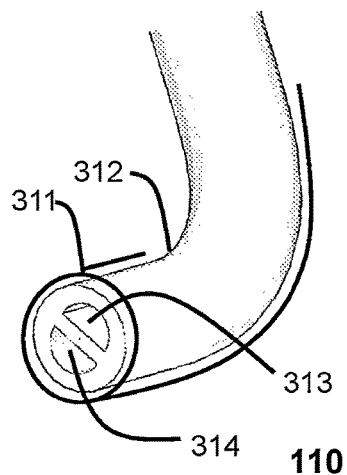
FIG. 3C depicts a portion of a smart skin surface for user interface control of the wireless wearable media accessory in accordance with one exemplary embodiment.

FIG. 3C depicts a section of the smart skin surface 311 on an exterior 312 of the bend sensor 110. Various types and materials of the smart skin surface are herein contemplated. In one configuration, the smart skin surface is resistance based comprising a series of resistance bands separated by small gaps there between, such that touching by a finger along the resistance bands changes a resistance, where the BTE module monitors for a change in the resistance thereon that detects user input gestures for gesture control. Referring back to FIG. 3A or ahead to FIG. 3E, these resistance bands are seen as sections 116. In another arrangement, the smart skin surface is resistance based comprising two thin, electrically resistive layers (311/312) separated by a small gap there between, such that applied pressure by a finger along a length of the bend sensor causes the two layers to touch and become connected and lowering a resistance, where the BTE module monitors for a change in the resistance thereon that detects user input gestures for gesture control of functions.

Figure 3D:
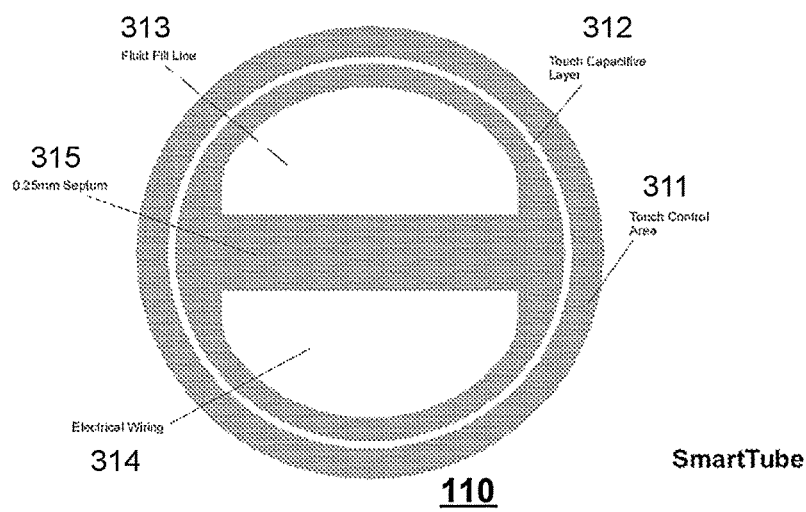
FIG. 3D depicts a front plan view of the smart skin tube or SmartTube in accordance with an embodiment herein.
Figure 3E:
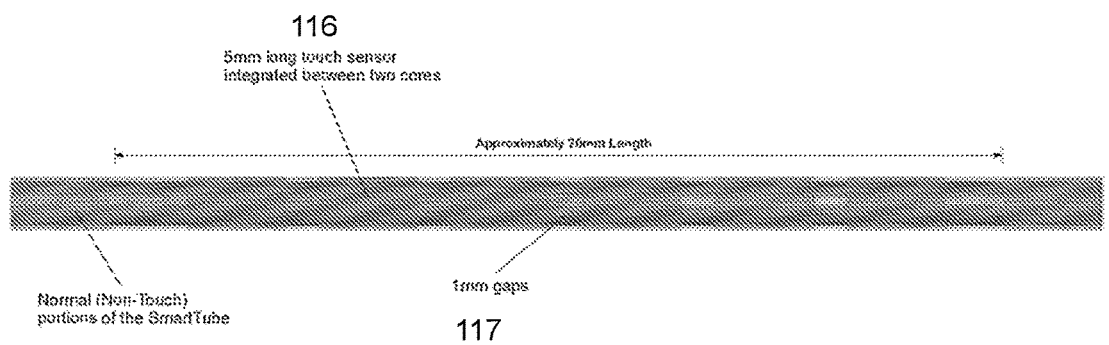
FIG. 3E depicts a side view of the smart skin tube in accordance with an embodiment herein.

In another configuration the smart skin surface is capacitive based comprising a series of capacitive bands separated by small gaps there between, such that touching by a finger along the capacitive bands changes a capacitance, where the BTE module monitors for a change in the capacitance thereon that detects user input gestures for gesture control of functions. FIG. 3D illustrates a front plan view of an embodiment of the bend sensor 110 which includes a first passage 313 which serves as a lumen for fluids, a second passage 314 which serves as a lumen for electrical wiring, a touch control area 311, a touch capacitive layer 312, and a septum 315 dividing the first passage 313 from the second passage 314 in the bend sensor 110. Referring back to FIG. 3A and to FIG. 3E these capacitance bands are seen as sections 116 separated by gaps 117. In another arrangement, the smart skin surface is capacitive based comprising an insulating layer (312) and an outer coating (311), such that a touching of a finger on the outer coating 311 results in a distortion of the smart skin's electrostatic field, where the BTE module monitors for a change in the electrostatic field thereon that detects user input gestures. In yet another configuration the smart skin surface is optical based comprising an infrared transceiver and an optical fiber, such that a touching of a finger on the optical fiber results in a distortion of the smart skin's light spectrum, where the BTE module monitors for a change in the light spectrum that detects user input gestures.

Also note that the first passage 313 of the bend sensor couples the fluid lumen conduit 126 to the balloon 121 in the earpiece 120 at one end and the bladder 211 in the BTE module 130 at the other end (See FIGS. 1C, 1E, and 1F). Also shown is the second passage 314 of the bend sensor, which recall, passes the wires of the electrical lumen conduit 127 to the electronic circuitry of the earpiece 120 at one end and the electronic components in the BTE module 130 at the other end.

FIGS. 4A-4B illustrate an anatomy of the human ear with anatomical landmarks and features. This figure is referenced for study of the front of the ear for ergonomic and comfort fit of the wearable media accessory 100. FIG. 4A shows anatomical features of the crus back, crus front, antitragus, intertragal notch, and tragus for best fit of the bend sensor 110. FIG. 4B shows the tip of the pinna and the concha for determining best fit around the ear. FIG. 4C illustrates a large statistical sampling of ear dimensions among female 415 and male 416 populations for determining metric ranges of the BTE module, for example, width, length, and height ranges. Understandably, the statistical study provides a valuable indication of the breadth of shapes, sizes and designs the BTE module could assume.

FIGS. 4D-4E illustrate the novel shaping of the bend sensor 110 for the front of the ear in accordance with the best fit, curve and shape of the anatomical features identified in FIGS. 4A-4B and through the statistical analysis shown in FIG. 4C; features that were critical to identifying the best and most comfortable fit for the bend sensor 110 for the anatomical locations of the front of crus and tragus. It is one of the reasons the bend sensor 110 is flexible and of low durometer within a 10 mm section from an entrance of the ear canal entrance orifice to a first bend within the ear canal to provide manual shaping and comfortable fit. Also note that the bend sensor can be made of a translucent material or colored to best match the skin color of the user to make the overall device less visible to an outside observer.

FIGS. 4F-4G illustrate an anatomy of the human ear with anatomical landmarks and features. This figure is referenced for study of an ergonomic and comfortable wearable earpiece component along the top of the ear. FIG. 4H illustrates the novel shaping of the behind the ear module 130 in accordance with the best fit, curve and shape of the anatomical features identified in FIGS. 4A-4B and through the statistical analysis shown in FIG. 4C. The features of FIG. 4F have been critical to identifying the best and most comfortable fit within the posterior articular groove between the temporal squanosa and back of the pinna as shown in FIGS. 4G-4H.

Notably, the shaping design of BTE module 130 along the post articular groove of the ear is formed in accordance with these ear anatomy studies; namely those identifying anatomical landmarks and features for a best fit to within a 95% confidence interval of studied ears. For example, the shaping design of BTE module 130 between the temporal squanosa and the pinna of the ear is formed in accordance with these ear anatomy studies identifying anatomical landmarks and features for a best fit to within a 95% confidence interval. In other words, these studies identify anatomical landmarks to ultimately produce products that are designed to fit between the 5% and the 95% (5th and 95th percentile) geometry of human conduits such as ear canals. Moreover, the shape, weight and size of the BTE module 130 was designed in view of the anatomical and statistical studies above for best fit with respect to comfort, placement and balance and in view of the device 100 parameters (e.g., width, length, height, shape, volume, etc.) Another feature of the embodiments is the radius curvature of the BTE module 130. A diagrammatic illustration of the radius function (see R) is shown in FIG. 4I. The radius function characterizes one primary aspect of the best fit. This benefit of the radius of curvature and BTE module 130 design is shown in FIG. 4J, which illustrates a best fit, curve and shape of a wireless behind the ear media device accessory from study of a ears in a male population in accordance with one exemplary embodiment. As can be seen, the BTE module 130 is preferably seated for balance and weight distribution between the 5% and 95% male population samples, having taken into account the anatomical features and the statistical variation of ear landmarks above. The radial body curve of the BTE module 130 along a post articular groove specific to a male ear anatomy provides a best fit to within 5% to 95% of male population with respect to BTE module positioning and balance. FIG. 4K illustrates a best fit, curve and shape of a wireless behind the ear media device accessory from study of ears in a female population in accordance with one exemplary embodiment. As can be seen, the BTE module 130 is preferably seated for balance and weight distribution between the 5% and 95% female population samples, having taken into account the anatomical features and the statistical variation of ear landmarks above. The radial body curve of the BTE module 130 along the post articular groove specific to a female ear anatomy provides a best fit to within 5% to 95% of female population with respect to BTE module positioning and balance.

FIG. 4L depicts the placement of the BTE module behind the ear and the earpiece within the ear canal. As shown, the pinna is removed to more clearly show the BTE module positioning. FIG. 4M includes the pinna and further illustrates that the BTE modules lays well hidden behind the ear, essentially hidden from view from the front or side. FIG. 4N further shows the wearable media device coupled to eyewear via a mechanical coupling such as a magnetic connector. FIG. 4O further illustrates a closer view of the coupling between the wearable media device and the eyewear. The description of FIGS. 5A and 5C provide greater detail of the mechanical coupling to eyewear in a particular embodiment.

Figure 4V:
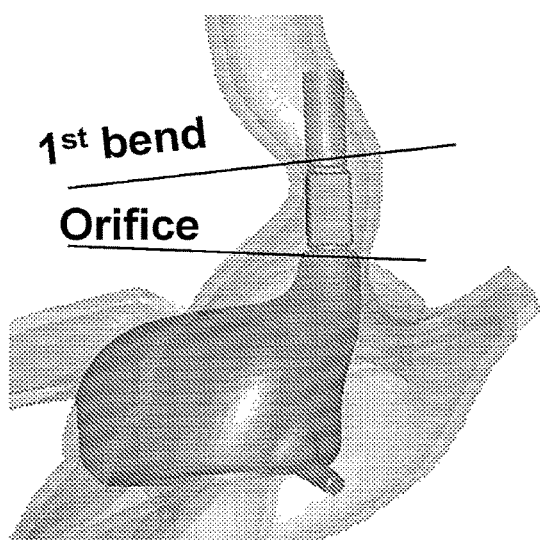
FIG. 4V illustrates the placement of an in-ear earpiece between the orifice and first bend of the ear canal in accordance with an embodiment.

FIG. 4P(a) through FIG. 4R9(b) graphically illustrate the results of anthropomorphic studies done to show the statistical shaping of the EAC and the orifice for a best fit test. FIGS. 4P(a), 4Q(a), and 4R(a) illustrate a statistical model of the ear canal with a lower bound surface that is essentially highlighted in the central area of each figure. FIGS. 4P(b), 4Q(b), and 4R(b) illustrate a corresponding statistical model of the ear canal with a lower bound surface that is also highlighted in the central area of each figure. FIG. 4S illustrates the various sections of the EAC that were studied in the statistical analysis, but a primary focus was the area between the orifice and the first bend of the EAC as illustrated in FIG. 4V where an earpiece would reside between the orifice and the first bend. The first bend of the EAC generally has the most dramatic differential in diameters among the varied sections measured as illustrated in FIG. 4T where the vertical diameter of the ellipse is significantly larger than the vertical diameter. FIG. 4U further illustrates the shape of the orifice from left to right respectively of a small male, large male, large female, and small female. As can be seen, the variability and size can be significant, but the design of the product can be made to accommodate such variability as a result of these studies.

Referring to FIG. 5A, an eyewear 50 that communicatively and mechanically couples to the wearable media device 100 is shown in accordance with one embodiment. As illustrated, the eyewear 50 when placed on the face and then oriented downward 51 so the left and right arms of the eyewear are positioned to rest along the posterior articular grove of the left and right ear (see FIG. 4G) respectively, the eyewear 50 communicatively couples to the wearable media device 100 to operate holistically as a wearable system 500. As previously discussed in FIGS. 4A-4J, the BTE module 130 resting position on the pinna (see W gravity vector, width and length 418 (male)/419(female) in FIG. 4H) was designed for a best fit, orientation and balance with the arm of the eyewear to accommodate a 95% confidence interval of studied ears to comfortably sit the arm on the BTE module 130. Similarly, the back ear groove width and length of the BTE module 130 was shaped to a best fit, orientation and balance with the arm of the eyewear to accommodate a 95% confidence interval of studied ears to comfortably sit the arm on the BTE module 130.

Figure 5B:
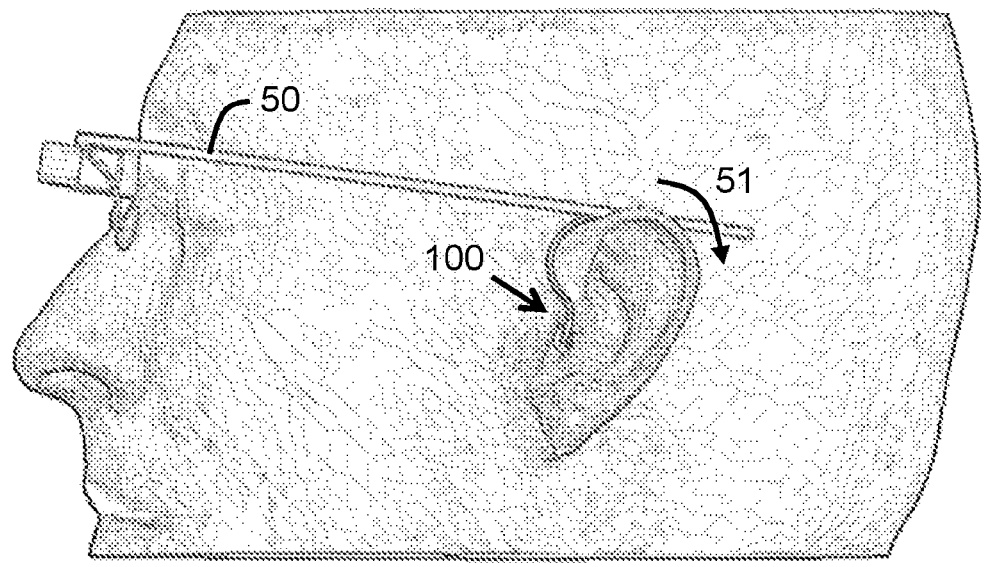
FIG. 5B illustrates a front view of the eyewear of FIG. 5A in accordance with one exemplary embodiment.
Figure 5B:
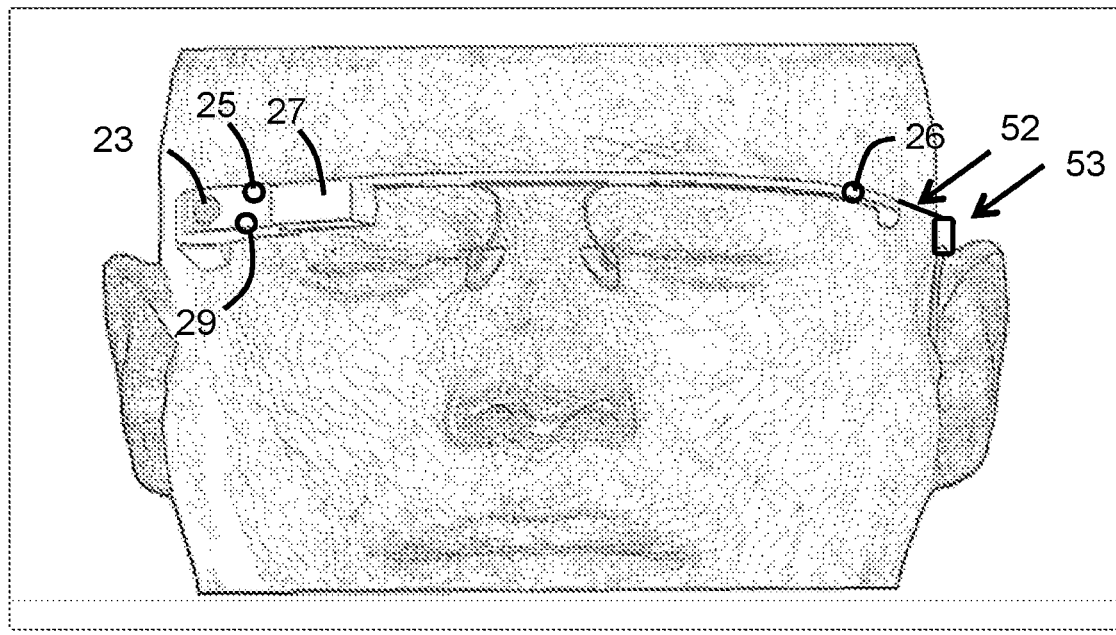
Figure 5C:
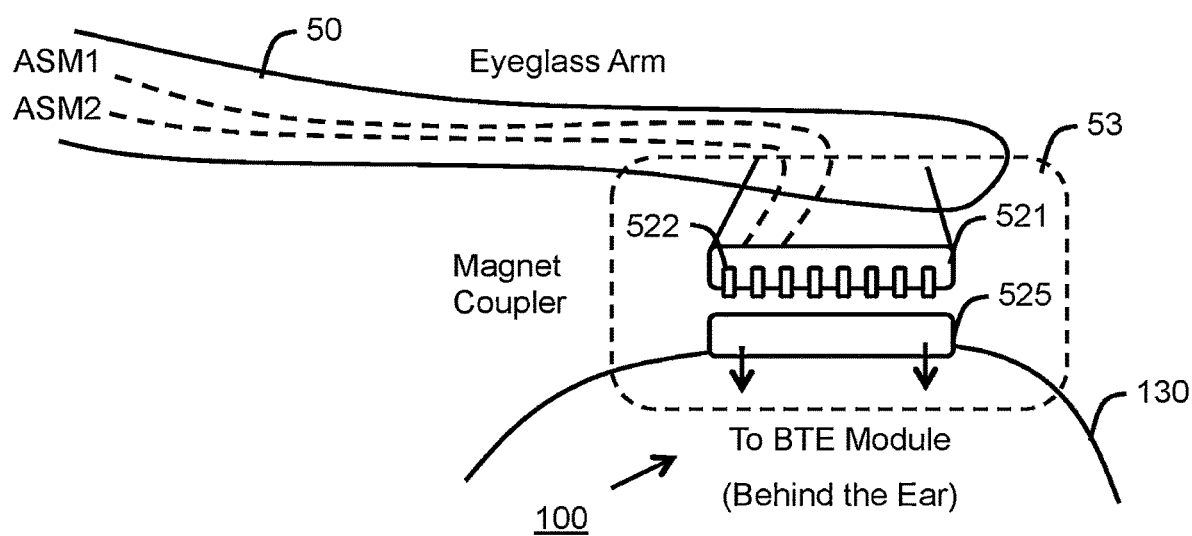
FIG. 5C illustrates a magnetic coupler providing for mechanical and communication coupling of the eyewear and the wearable media accessory in accordance with one exemplary embodiment.

As shown in FIG. 5B, the eyeglasses 50 include at least one microphone 25 for capturing sounds in proximity to, and in front of the eyeglasses. A second microphone 26 can be used to capture stereo sounds. In conjunction with the ambient sound microphone located on the BTE module 130, which is nearer the back of the wearer's head, the system 500 can also be configured to provide full surround capture when used with two earpieces 100; that is, 2 microphones in the front and 2 microphones in the back. These microphone signals can be communicated to the earpiece 100 by way of the magnetic coupler 53. The eyeglasses 50 can also include one or more optical elements, for example, a camera 23 situated at the front for taking pictures or video.

The camera 23 can capture images and video and by way of a processor (on the eyeglasses, earpiece, or communicatively coupled thereto) perform there from image recognition, upon identifying a person, place or object in the images or video, communicates audible information related to the person, place or object to the earpiece as a whisper notification. For example, the wearable media accessory 100 upon receiving personal information can quietly and discretely present the information to the wearer of the earpiece 100, for example, the name of a person to whom the wearer is speaking but not remembering that person's name.

A display 27 may be present on an interior panel of the eyeglasses 50 thereby permitting the wearer to receive visual information, for example, the pictures taken with the camera 23 or other images provided by other users. The display can be an interior projecting visual display that presents visual alert messages to a wearer of the eyewear regarding at least one operation of the earpiece, including at least one among a battery power level, an incoming audible message, an identified ambient sound, and an incoming mobile device call. The eyewear can also include an exterior illumination element 29 that presents visual status to users within proximity of a user wearing the eyewear, regarding at least one operation of the earpiece, including at least one among ambient sound capture status, a recording status, a warning status, a do not disturb status, and a welcome interaction status. Although not shown, the eyeglasses may also contain a transceiver for communicating with other mobile devices or systems, for example, via Bluetooth, Wi-Fi or other communication protocol. This transceiver can also communicate with the earpiece 100 for coordination and management of audio information.

As illustrated in FIG. 5B, the arm 520 of the eyewear 50 communicatively couples to the BTE module, via a magnetic coupler 53 that provides mechanical stability and electrical coupling leads to establish a media communication that coordinates delivery of audible and visual messages between the eyewear 50 and the earpiece 100. The magnetic coupler 53 is yet another feature that, besides coupling communication between the devices, can provide power from the eyewear 50 to the earpiece 100, for example, in order to recharge the BTE module 130 without removing it from the ear. In this way, the eyeglasses refresh a battery power of the BTE module through the electrical leads of the magnetic coupler. It may also recharge the battery via inductive charging. In such an arrangement, the system 500 established by the earpiece 100 and eyeglasses 50 operate as the wearable computing device, for collective processing of acoustic signals (e.g., ambient, environmental, voice, etc.) and media (e.g., accessory earpiece connected to eyeglasses for listening) when communicatively coupled to a media device (e.g., mobile device, cell phone, etc.). In this arrangement, analogous to an earpiece with microphones but rather embedded in eyeglasses, the user may rely on the eyeglasses for voice communication and external sound capture instead of requiring the user to hold the media device in a typical hand-held phone orientation (i.e., cell phone microphone to mouth area, and speaker output to the ears). That is, the eyeglasses 50 sense and pick up the user's voice (and other external sounds) for permitting voice processing and in operation with earpiece 100 providing audio and voice.

FIG. 5C is an illustration magnetic coupler 53 in accordance with one exemplary embodiment. It includes a first attachment 521 on the eyeglasses 50, and a second attachment 525 on the BTE module 130 of the earpiece 100, such that the first attachment 521 and second attachment 525 when in proximity and magnetically coupled preferably orient the eyeglasses with the BTE module 130 in a predetermined physical alignment. This is done to also correlate a person's visual orientation with the BTE module; that is, it calibrates the balance and orientation of the earpiece 120 with the orientation of the eyeglasses 50, for example, in order to assess a direction of a sound from multiple microphones with respect to the wearer's visual orientation and looking direction. Recall, the eyewear 50 can include a left ambient sound microphone with left lead wires, and a right ambient sound microphone with right lead wires, where the left lead wires and the right lead wires 522 electrically couple to the BTE module 130 via the magnetic coupler 53, and the BTE module 130 additionally processes ambient sounds with audio content delivered to the earpiece captured via the left ambient sound microphone and the right ambient sound microphone.

Figure 6A:
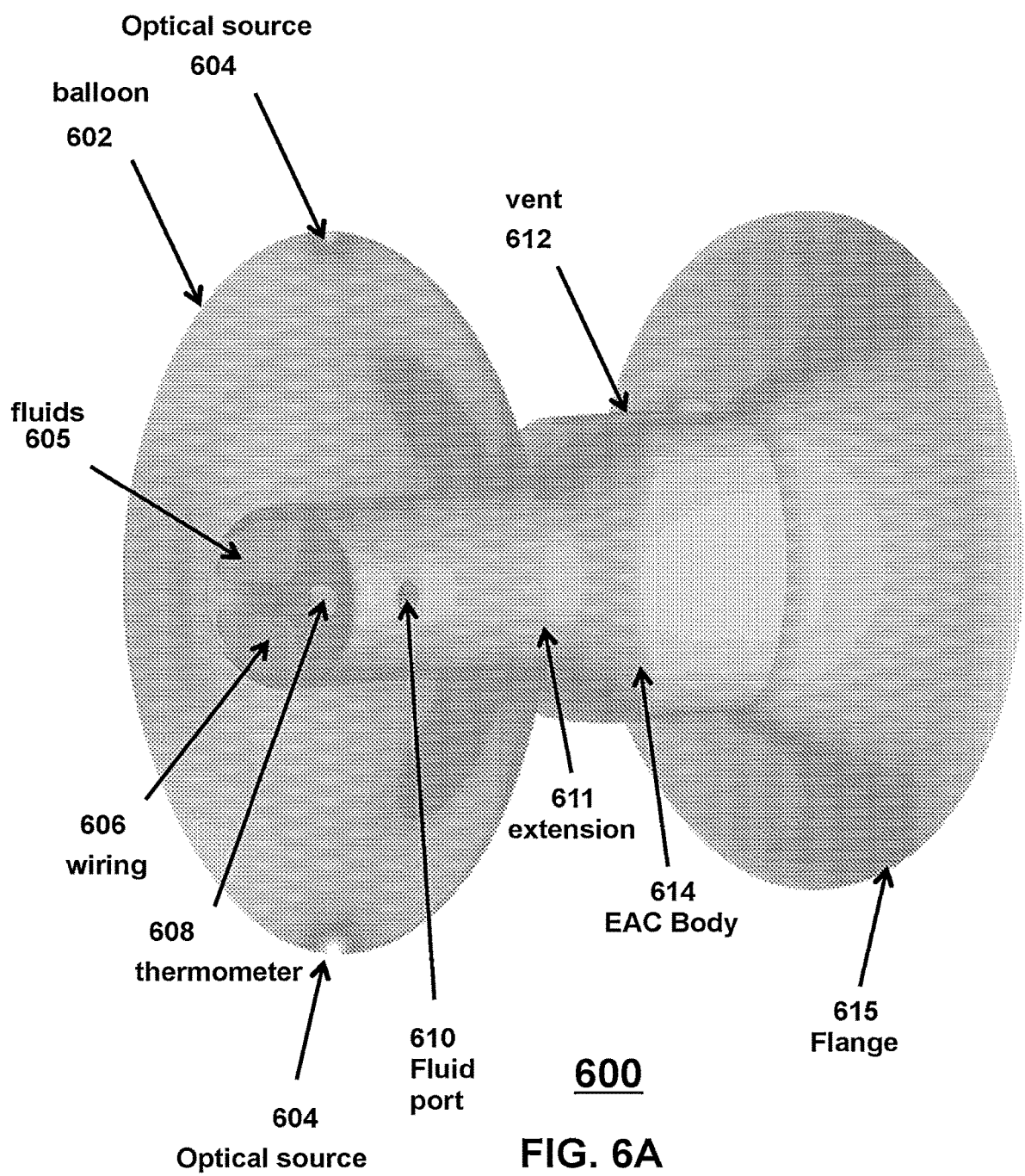
FIG. 6A illustrates a portion of an earpiece of a wireless wearable media accessory having a balloon in accordance with an exemplary embodiment.

FIG. 6A depicts a perspective view of yet another embodiment of an earpiece 600 in accordance with the embodiments. The earpiece 600 can be an independent self-contained device or can operate cooperatively with a second earpiece or with a BTE module as described above, or with another external device such as a smart phone, a pair of smart glasses, or other electronic device. Many of the portions in this device are similar to portions previously described in other embodiments. Thus, briefly, the earpiece 600 can include a EAC body portion 614 coupled to a flange 615 at a proximal end and a balloon 602 via an extension 611 at a distal end. The balloon 602 can include one or more optical sources 604 used for biometric or physiological measurements or monitoring. The extension 611 can be a portion of a tri-lumen having various conduits including a conduit 605 for fluids, a conduit 606 for wiring, and a conduit for a thermometer probe 608. The extension can further include a fluid port 610 where fluids are transferred to or from the balloon 602 to a reservoir (in the EAC body portion 614 in some embodiments, or elsewhere in the earpiece 600 in other embodiment, and outside the earpiece 600 in yet other embodiments). Note, the EAC body portion 614 can also include a vent 612 for equalization purposes.

Figure 6B:
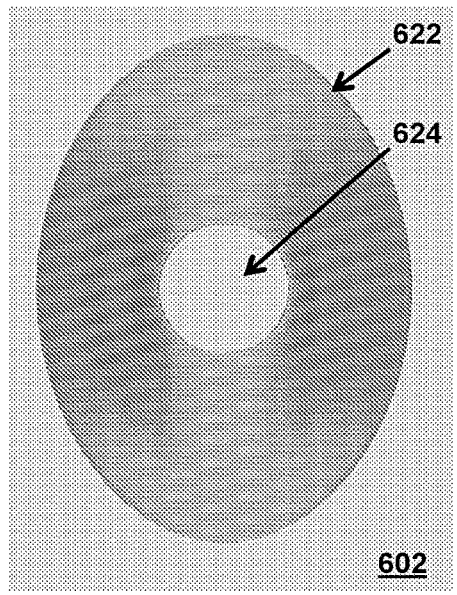
FIG. 6B illustrates a front plan view of the balloon in accordance with an embodiment without circuitry on the balloon.
Figure 6C:
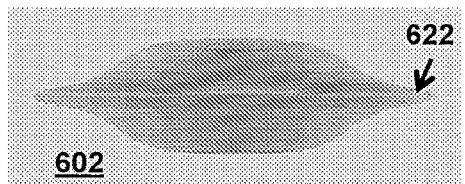
FIG. 6C illustrates a top plan view of the balloon in FIG. 6B accordance with an embodiment.
Figure 6D:
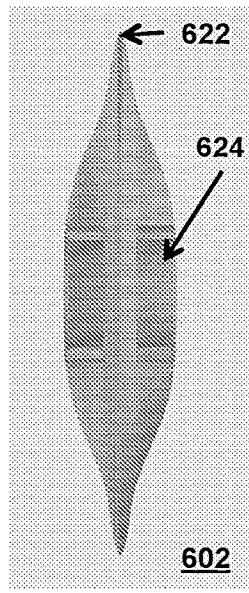
FIG. 6D illustrates a side view of the balloon in FIGS. 6B and 6C in accordance with an embodiment without circuitry on the balloon.

The balloon can have various designs based on the functionality and features desired. FIGS. 6B, 6C, and 6D respectively illustrate a front plan view, a horizontal side view, and a vertical side view of the balloon 602. The balloon 602 can include a central aperture or hole 624 where the tri-lumen or extension 611 resides and further includes a thin or narrow edge 622 as illustrated.

Figure 6E:
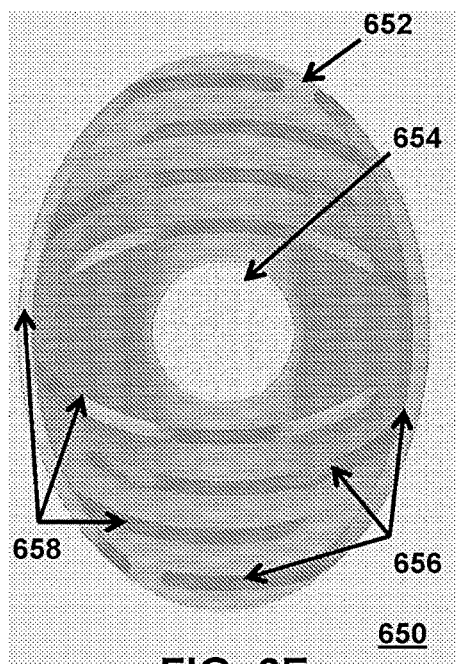
FIG. 6E illustrates a front plan view of a balloon in accordance with an embodiment with circuitry on the balloon.
Figure 6F:
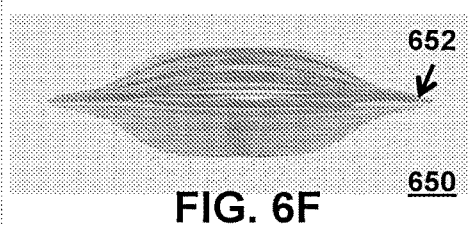
FIG. 6F illustrates a top plan view of the balloon in FIG. 6E accordance with an embodiment.
Figure 6G:
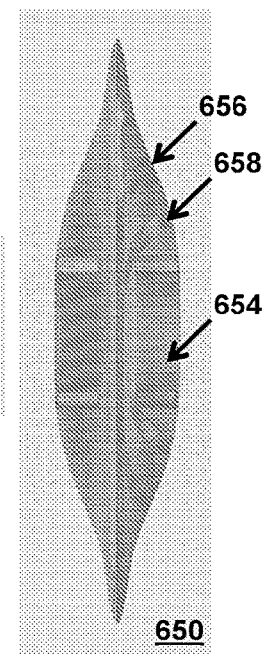
FIG. 6G illustrates a side view of the balloon in FIGS. 6E and 6F in accordance with an embodiment with circuitry on the balloon.

FIGS. 6E, 6F, and 6G respectively illustrate an alternative balloon 650 with a front plan view, a horizontal side view, and a vertical side view. The balloon 650 includes a central aperture or hole 654 where the tri-lumen or extension 611 resides and further includes a thin or narrow edge 652 as illustrated. The balloon 650 further includes respective conductive runners 656 and 658 that can be embedded within the balloon polyurethane layers or alternatively can be placed on either the outside surface or the inside surface of the balloon. The conductive runners can be made of elastomeric conductive runners or conductive ink or other conductive materials based on the desired functions. The conductive runners can be used for capacitive measurements or other biometric or physiological measurements or monitoring.

Figure 6H:
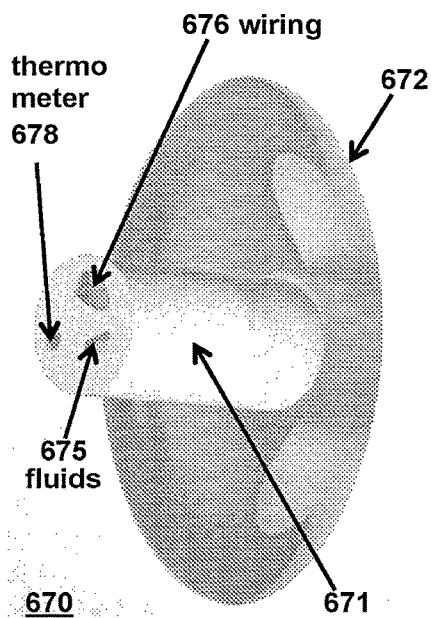
FIG. 6H illustrates a perspective view of a balloon having a tri-lumen in accordance with an embodiment.
Figure 6J:
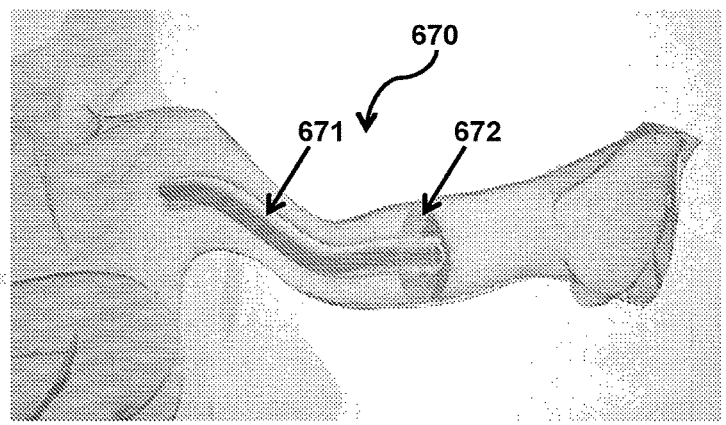
FIG. 6J illustrates the balloon and tri-lumen of FIGS. 6H and 6I in-situ within an ear canal in accordance with an embodiment.
Figure 6I:
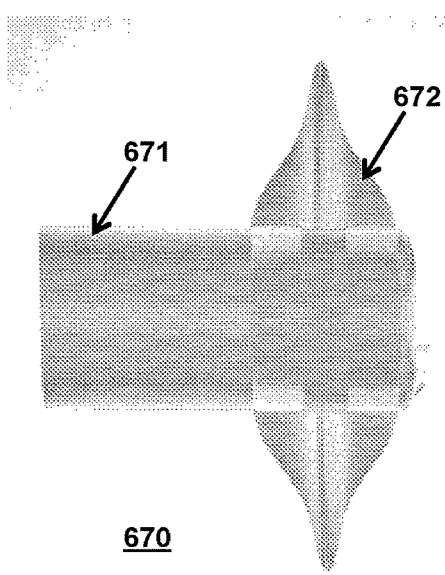
FIG. 6I illustrates a side view of the balloon and tri-lumen of FIG. 6H.

FIG. 6H is a perspective view of an earpiece 670 having a balloon 672, an extension portion 671 that forms a portion of a tri-lumen having a conduit 675 for fluids, a conduit 676 for wiring, and a third conduit for a thermometer probe 678. FIG. 6J further illustrates the earpiece 670 with the balloon 672 and extension portion 671 within the EAC anatomy. Note that the thermometer probe in such an embodiment can be place fairly close to the skull for accurate temperature measurements. FIG. 6I illustrates a side view of the earpiece 670.

FIGS. 6K-6N illustrate various embodiments of the earpiece and how such embodiments would appear as placed in a human ear. The visibility aspects can vary significantly from embodiment to embodiment. FIG. 6K illustrates an earpiece 680 that would be coupled to an external device such as a smart phone. Such a device would likely draw power from the external device and thus a wire is illustrated that protrudes downward from the earpiece. FIG. 6L illustrates an earpiece 685 that would include a BTE module that is placed behind the ear. Thus, a small and thin wire goes from the earpiece to the BTE module residing behind the ear. FIG. 6M illustrates an In-Concha earpiece 690 that can operate independently or can operate cooperatively with left and right earpieces. An optional wire can couple the left and right earpieces as shown in the top portion of FIG. 6M. The wire can be eliminated if the devices are coupled using Bluetooth or other wireless protocol. FIG. 6N illustrates an In-ear earpiece 695 that can operate independently or can operate cooperatively with left and right earpieces (695). This embodiment would provide the greatest level of "invisibility" among the embodiments and the when using left and right earpieces, the devices can be coupled using Bluetooth or other wireless protocol. The earpieces 695 would be independently powered either using battery chemistry in the balloons as previously discussed or using an arrangement of button cells or other battery source.

Figure 6O:
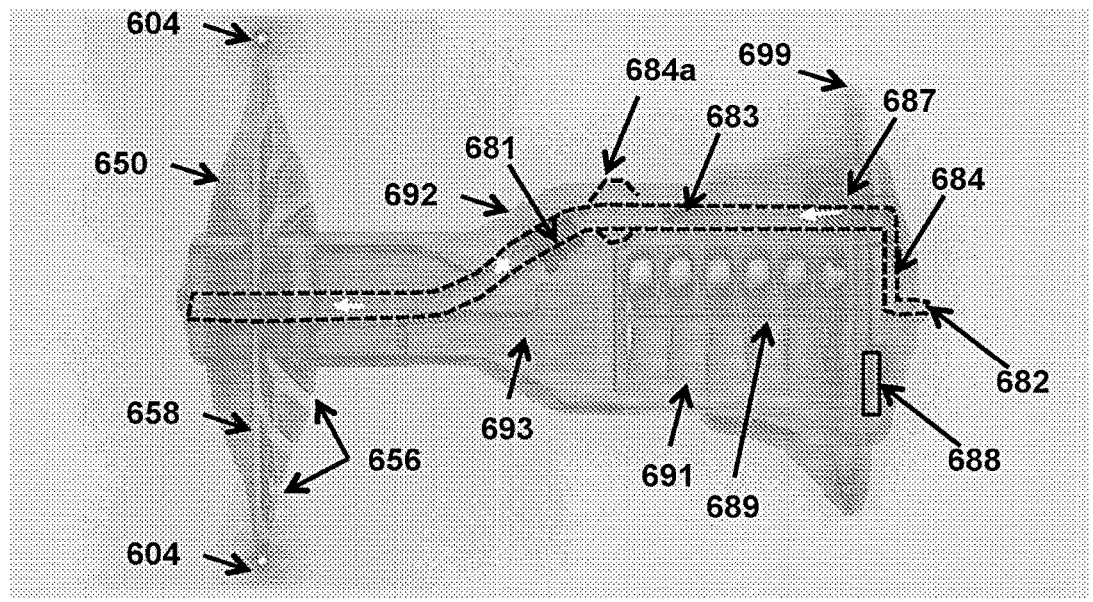
FIG. 6O illustrates another wireless wearable media device worn in the ear canal in accordance with an embodiment.

FIG. 6O illustrates an earpiece 696 that is independently powered by a series of button cells 691. The earpiece 696 can include the balloon 650 that includes the conductive runners 656 and 658 as well as the optical sources 604. The optical sources 604 can be LEDs for example. The various components in the earpiece 696 would be appropriately miniaturized to fit within a small overall package. The earpiece 696 can further include an ear canal receiver (speaker) 693, an ear canal microphone 681, a mini-valve or mini-pump 683, an ambient sound microphone 687, and processor 688 which can be coupled to the various electronic components for control or monitoring of signals. Each of these devices would reside within respective (and/or shared) conduits and have appropriate porting. One conduit 684 and port 682 is particularly highlighted and can serve as an inflation channel for the balloon 650 as will be further described below. Other conduits can be for acoustics, physiological monitoring, venting, and electronic or optic connectivity for example. The earpiece 696 can further include an antenna 689 that can be used for one or more of RF transmissions, Bluetooth transmissions, near-field conductive transmissions, and/or contactless charging. The processor 688 can couple to various sensors in the earpiece 696 including, but not limited to biometric sensors or other sensors. The types of sensors can include sensors for pulse, temperature, blood pressure, blood oxygenation, heart rate, respiratory rate, perspiration, humidity and acceleration. The sensors can be separate devices or in some embodiments can be included within the functionality of the processor 688. For example, the earpiece can include a separate accelerometer, fall detector, or motion detector in some embodiments and in other embodiments some of those functionalities can be incorporated within the processor 688. Also note that the balloon can include a biometric sensor layer that is capacitive, resistive or optical in some embodiments.

The earpiece 696 includes an EAC body 692 can be made of a low durometer liquid injection molded silicone, but can be made of other materials such as thermoplastic elastomers, thermoplastic polyurethanes or other elastomeric biocompatible materials. In one embodiment, the material used can have a durometer range of 15-20 Shore A. The EAC body 692 can hold or enclose the ear canal microphone 681 and an ear canal receiver (speaker) 693 that is inserted and retained within a proximal end of the EAC body 692. The EAC body 692 (as well as some of the other external components such as the stop flange 699) should be made of flexible, soft, low durameter materials that will not swell (hydrophobic). The EAC body 692 and other housing components need to traverse a tortuous ear canal (see FIGS. 2X and 6J) during insertion of the earpiece and thus should be flexible and malleable. Further note that the ear canal receiver 693 should be designed to be relatively short to have some room to allow the overall design to bend and flex. In other words, the EAC body 692 and stop flange 699 should have many degrees of movements as it traverses a tortuous ear canal. The ear canal receiver 693 and some of the other electronic components within the earpiece 696 are typically made of hard materials that are not as flexible as the external housing components. Thus, the placement of the components within the overall earpiece should be considered to allow overall flexibility and malleability for the earpiece design. The flexibility in the design also enables the accommodation to many different individual ear geometries and also enables consistent performance during mandibular movement from chewing or speaking for example.

Figure 6Q:
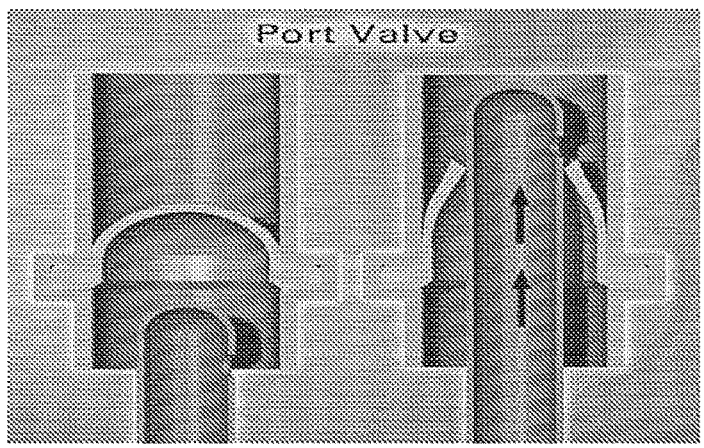
FIG. 6Q illustrates the function of a port valve and inflation mechanism in accordance with an embodiment.
Figure 6P:
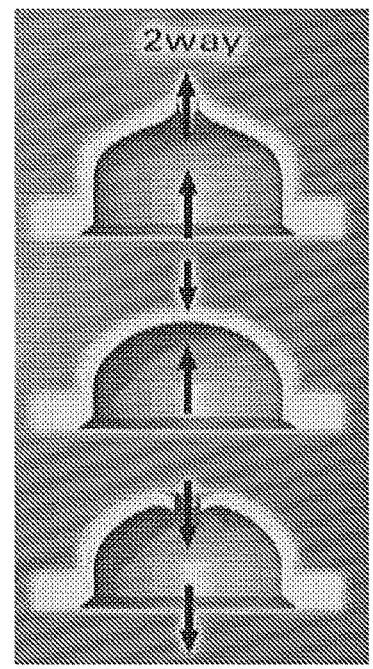
FIG. 6P illustrates a two way valve used in the wireless wearable media device of FIG. 6O in accordance with an embodiment.

FIGS. 6Q and 6P illustrate the mini-valve 683 in further detail. Note that the valve 683 shown in FIG. 6O is shown in one particular location along the conduit 684 for illustration purposes and is not limited to residing in the particular location shown. The valve 683 can be suitably placed anywhere along the path of the conduit 684. In one scenario as shown in FIG. 6Q, the valve can serve as a port valve and can be penetrated by a needle that is used for inflating the balloon with a fluid. The fluid can come from a separate canister or can that is under pressure and the fluid is injected into the balloon with forward pressure using the needle shown. Once the needle is removed, the fluid would then stay in the balloon for a period of time even though there is some back pressure against the valve 683. A significant amount of back pressure or force would be needed to have the valve 683 allow fluid to go from the balloon back in a reverse direction towards the outside. In one embodiment, the valve operates as a dome valve which typically is used as a 1 or 2 way check valve. The dome valve is generally designed to have near zero opening pressure (zero crack pressure). The valve will allow gas or liquid to pass through in the forward flow direction with a small amount of forward pressure. The valve will remain closed at static pressure, and will open at a high pressure in the reverse direction. As in the needle example, the dome valve can also be used as an access/trocar valve to allow devices to pass through the valve, while maintaining a pressure and liquid seal. In this application, it is typically mated with a backup seal.

Referring again to FIG. 6O, the earpiece 696 can include a number of conduits and ports including a fluid channel or conduit 684 having a fluid port 682. In one embodiment, the conduit 684 itself can be arranged and constructed when filled with fluid to exert a forward inflation pressure towards the balloon 650. Operationally, as the earpiece is placed in the ear of a user, the conduit 684 can accommodate the external pressure exerted on the balloon 650 as the balloon 650 deformed and a temporary transfer or flow of fluid can move back toward the valve 683 until an equilibrium state of fluid returns between the conduit 684 and the balloon 650. In this regard, the conduit 684 would be made of a material of a higher shore value than the material used to construct the balloon 650 and the conduit would need to be of sufficient length to provide such forward inflation pressure. In other words, a conduit 684 of sufficient length would be made of a material that is less compliant than the balloon 650. In one embodiment, adequate length for the conduit can be achieved by providing a serpentine, spiraling, or meandering configuration (not shown). Thus, in a natural state, the conduit 684 filled with fluid would exert the forward inflation pressure described above.

In a variant embodiment, the conduit 684 can include an optional bulbous member or internal bladder 684a that can be made of a less compliant (or higher shore value) than the material used for the balloon 650 and/or the conduit 684. In some embodiments, the material for the internal bladder 684a is less compliant than both the conduit 684 and balloon 650. In some embodiments, the internal bladder 684a and conduit 684 are made of the same material which is less complaint than the material used for the balloon 650. In any case, the optional internal bladder 684a primarily exerts a forward inflation pressure toward the balloon 650 when the balloon 650, conduit 684 and internal bladder are filled with fluid. Operationally, the internal bladder 684a can serve as a reservoir that temporarily retains fluid forced towards the valve 683 as the balloon 650 is compressed or deformed during insertion of the earpiece 696 into a users ear. The valve 683 does not allow fluid to flow in a reverse direction unless the pressure externally exerted on the balloon exceeds the specified designed reverse crack pressure of the valve 683. Thus, the contemplated pressure exerted by placement of the balloon 650 in the ear would be designed well within the margins of the known reverse crack pressure of the valve 683. Once placed in the ear, the less compliant bladder 684a will apply its natural forward inflation pressure to the fluid (previously forced into the bladder 684a and conduit 684 during insertion of the earpiece into the user's ear) and force fluid flow towards the balloon 650. Fluid will then travel or migrate towards the balloon until an equilibrium state is achieved between the balloon 650, conduit 684, and internal bladder 684a. As described above, the conduit 684, the optional internal bladder 684a, and balloon 650 exhibit a hysteresis effect that shapes the balloon 650 with a desired shape and pressurizing force when placed in an ear and when removed from the ear.

Figure 7:
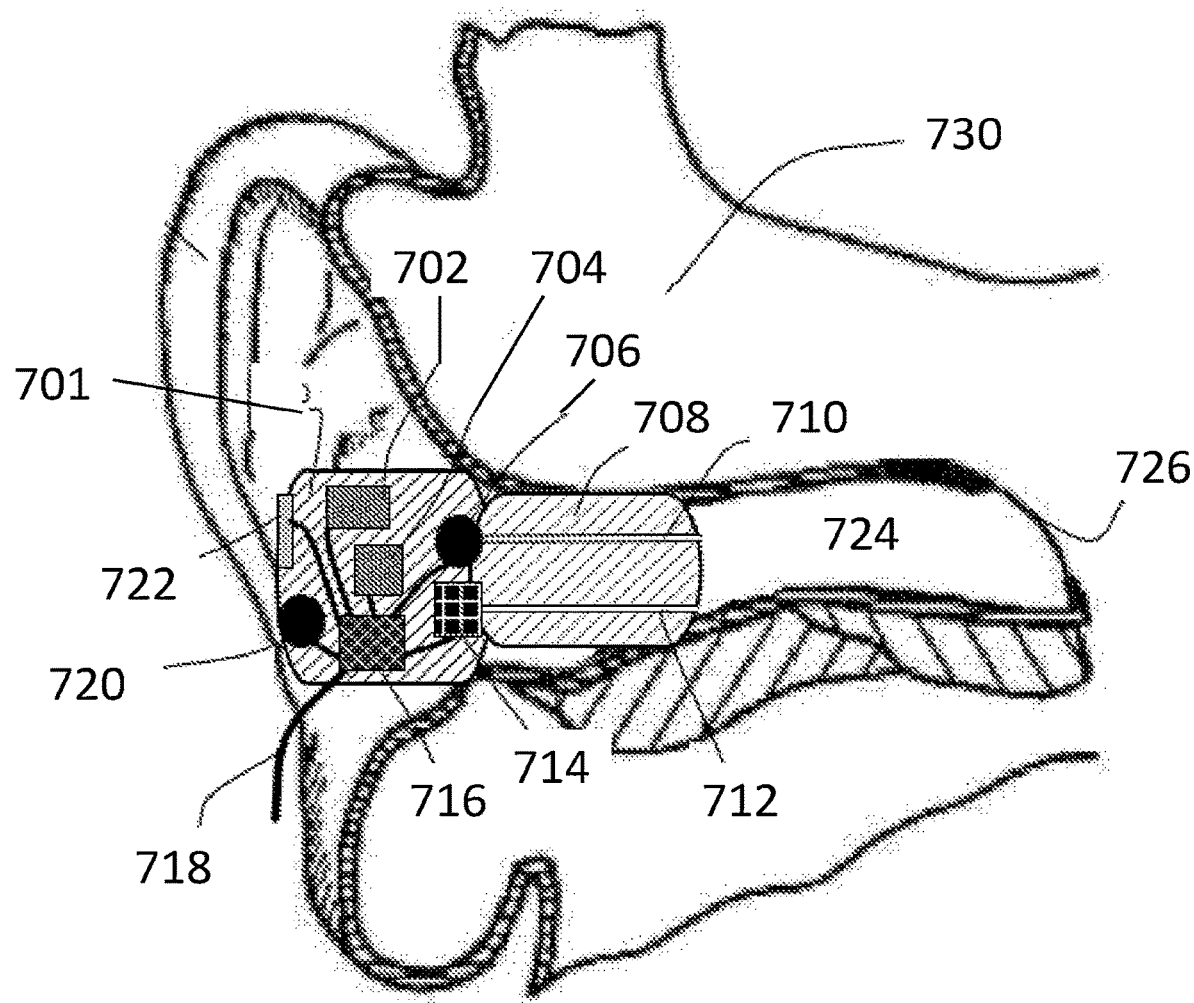
FIG. 7 illustrates a sound isolating earphone in accordance with another embodiment.

FIG. 7 illustrates an exemplary Sound isolating (SI) earphone 700 that is suitable for use with the wearable media system 100 in accordance with another embodiment. Sound isolating earphones and headsets are becoming increasingly popular for music listening and voice communication. SI earphones enable the user to hear and experience an incoming audio content signal (be it speech from a phone call or music audio from a music player) clearly in loud ambient noise environments, by attenuating the level of ambient sound in the user ear-canal. The disadvantage of such SI earphones/headsets is that the user is acoustically detached from their local sound environment, and communication with people in their immediate environment is therefore impaired: i.e. the earphone has a reduced situational awareness due to the acoustic masking properties of the earphone.

Besides acoustic masking, a non Sound Isolating (SI) earphone can reduce the ability of an earphone wearer to hear local sound events as the earphone wearer can be distracted by incoming voice message or reproduced music on the earphones. With reference now to the components of FIG. 7, the ambient sound microphone (ASM) located on an SI or non-SI earphone can be used to increase situation awareness of the earphone wearer by passing the ASM signal to the loudspeaker in the earphone. Such a "sound pass through" utility can be enhanced by processing at least one of the microphone's signals, or a combination of the microphone signals, with a "spatial filter", i.e. an electronic filter whereby sound originating from one direction (i.e. angle of incidence relative to the microphones) are passed through and sounds from other directions are attenuated. Such a spatial filtering system can increase perceived speech intelligibility by increasing the signal-to-noise ratio (SNR).

FIG. 7 is an illustration of an earpiece 120 that can be connected to the system 100 of FIG. 1A for performing the inventive aspects herein disclosed. As will be explained ahead, the earpiece 700 contains numerous electronic components, many audio related, each with separate data lines conveying audio data. Briefly referring back to FIG. 1B, the system 100 can include a separate earpiece 700 for both the left and right ear. In such arrangement, there may be anywhere from 8 to 12 data lines, each containing audio, and other control information (e.g., power, ground, signaling, etc.)

As illustrated, the earpiece 700 comprises an electronic housing unit 701 and a sealing unit 708. The earpiece depicts an electro-acoustical assembly for an in-the-ear acoustic assembly, as it would typically be placed in an ear canal 724 of a user. The earpiece can be an in the ear earpiece, behind the ear earpiece, receiver in the ear, partial-fit device, or any other suitable earpiece type. The earpiece can partially or fully occlude ear canal 724, and is suitable for use with users having healthy or abnormal auditory functioning.

The earpiece includes an Ambient Sound Microphone (ASM) 720 to capture ambient sound, an Ear Canal Receiver (ECR) 714 to deliver audio to an ear canal 724, and an Ear Canal Microphone (ECM) 706 to capture and assess a sound exposure level within the ear canal 724. The earpiece can partially or fully occlude the ear canal 724 to provide various degrees of acoustic isolation. In at least one exemplary embodiment, assembly is designed to be inserted into the user's ear canal 724, and to form an acoustic seal with the walls of the ear canal 724 at a location between the entrance to the ear canal 724 and the tympanic membrane (or ear drum). In general, such a seal is typically achieved by means of a soft and compliant housing of sealing unit 708.

Sealing unit 708 is an acoustic barrier having a first side corresponding to ear canal 724 and a second side corresponding to the ambient environment. In at least one exemplary embodiment, sealing unit 708 includes an ear canal microphone tube 710 and an ear canal receiver tube 714. Sealing unit 708 creates a closed cavity of approximately 5 cc between the first side of sealing unit 708 and the tympanic membrane in ear canal 724. As a result of this sealing, the ECR (speaker) 714 is able to generate a full range bass response when reproducing sounds for the user. This seal also serves to significantly reduce the sound pressure level at the user's eardrum resulting from the sound field at the entrance to the ear canal 724. This seal is also a basis for a sound isolating performance of the electro-acoustic assembly.

In at least one exemplary embodiment and in broader context, the second side of sealing unit 708 corresponds to the earpiece, electronic housing unit 700, and ambient sound microphone 720 that is exposed to the ambient environment. Ambient sound microphone 720 receives ambient sound from the ambient environment around the user.

Electronic housing unit 700 houses system components such as a microprocessor 716, memory 704, battery 702, ECM 706, ASM 720, ECR, 714, and user interface 722. Microprocessor 916 (or processor 716) can be a logic circuit, a digital signal processor, controller, or the like for performing calculations and operations for the earpiece. Microprocessor 716 is operatively coupled to memory 704, ECM 706, ASM 720, ECR 714, and user interface 720. A wire 718 provides an external connection to the earpiece. Battery 702 powers the circuits and transducers of the earpiece. Battery 702 can be a rechargeable or replaceable battery.

In at least one exemplary embodiment, electronic housing unit 700 is adjacent to sealing unit 708. Openings in electronic housing unit 700 receive ECM tube 710 and ECR tube 712 to respectively couple to ECM 706 and ECR 714. ECR tube 712 and ECM tube 710 acoustically couple signals to and from ear canal 724. For example, ECR outputs an acoustic signal through ECR tube 712 and into ear canal 724 where it is received by the tympanic membrane of the user of the earpiece. Conversely, ECM 714 receives an acoustic signal present in ear canal 724 though ECM tube 710. All transducers shown can receive or transmit audio signals to a processor 716 that undertakes audio signal processing and provides a transceiver for audio via the wired (wire 718) or a wireless communication path.

Figure 8:
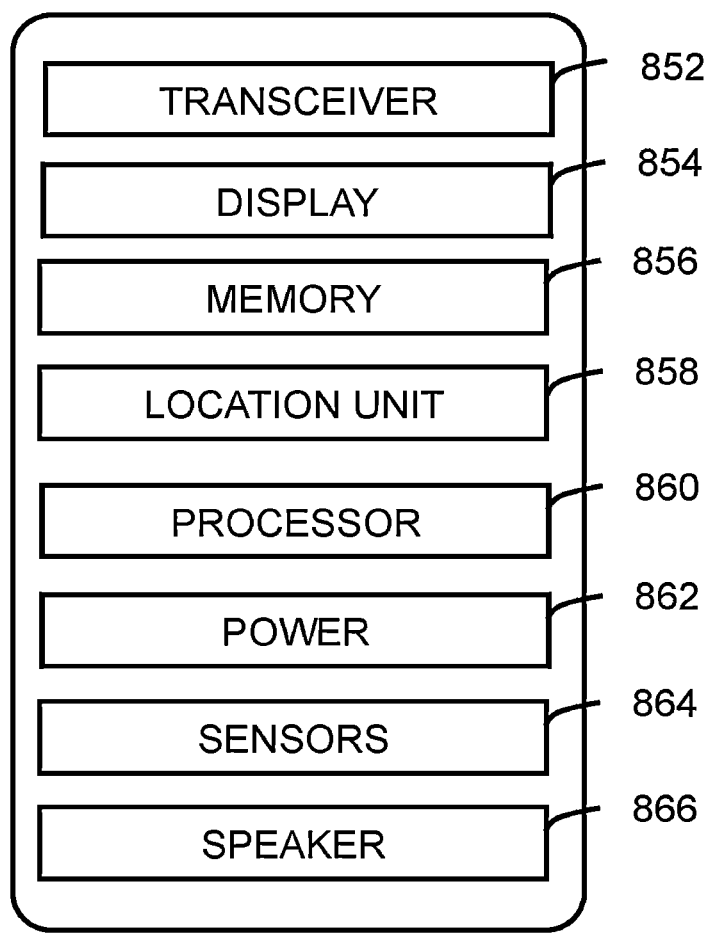
FIG. 8 is an exemplary processing device with components suitable for use in operating the wireless wearable media accessory in accordance with an exemplary embodiment.

FIG. 8 depicts various components of a multimedia device 850 suitable for use for use with, and/or practicing the aspects of the inventive elements disclosed herein, for instance method 200 and method 300, though is not limited to only those methods or components shown. As illustrated, the device 850 comprises a wired and/or wireless transceiver 852, a user interface (UI) display 854, a memory 856, a location unit 858, and a processor 860 for managing operations thereof. The media device 850 can be any intelligent processing platform with Digital signal processing capabilities, application processor, data storage, display, input modality like touch-screen or keypad, microphones, speaker 866, Bluetooth, and connection to the internet via WAN, Wi-Fi, Ethernet or USB. This embodies custom hardware devices, Smartphone, cell phone, mobile device, iPad and iPod like devices, a laptop, a notebook, a tablet, or any other type of portable and mobile communication device. Other devices or systems such as a desktop, automobile electronic dash board, computational monitor, or communications control equipment is also herein contemplated for implementing the methods herein described. A power supply 862 provides energy for electronic components.

In one embodiment where the media device 850 operates in a landline environment, the transceiver 852 can utilize common wire-line access technology to support POTS or VoIP services. In a wireless communications setting, the transceiver 852 can utilize common technologies to support singly or in combination any number of wireless access technologies including without limitation Bluetooth™, Wireless Fidelity (WiFi), Worldwide Interoperability for Microwave Access (WiMAX), Ultra Wide Band (UWB), software defined radio (SDR), and cellular access technologies such as CDMA-1X, W-CDMA/HSDPA, GSM/GPRS, EDGE, TDMA/EDGE, and EVDO. SDR can be utilized for accessing a public or private communication spectrum according to any number of communication protocols that can be dynamically downloaded over-the-air to the communication device. It should be noted also that next generation wireless access technologies can be applied to the present disclosure.

The power supply 862 can utilize common power management technologies such as power from USB, replaceable batteries, supply regulation technologies, and charging system technologies for supplying energy to the components of the communication device and to facilitate portable applications. In stationary applications, the power supply 862 can be modified so as to extract energy from a common wall outlet and thereby supply DC power to the components of the communication device 850.

The location unit 858 can utilize common technology such as a GPS (Global Positioning System) receiver that can intercept satellite signals and there from determine a location fix of the portable device 850.

The controller processor 860 can utilize computing technologies such as a microprocessor and/or digital signal processor (DSP) with associated storage memory such a Flash, ROM, RAM, SRAM, DRAM or other like technologies for controlling operations of the aforementioned components of the communication device.

What is claimed:

1. A method of controlling an audio device comprising:
   receiving a sensor signal generated by a sensor, wherein the sensor is on or in a tubular structure, wherein the tubular structure is part of the audio device;
   matching the sensor signal to a user gesture by a user, wherein the user gesture results from the user touching the sensor or touching a cover on the sensor or touching the tubular structure, wherein the user gesture is at least one of a finger movement along the tubular structure, pinching the tubular structure, double pressing the tubular structure, triple pressing the tubular structure, a press and then hold for a time period of the tubular structure, a dual touch of the tubular structure or pressing and rotating along the tubular structure; and
   controlling a function of the audio device by associating the user gesture with the function, wherein the function is at least one of playing audio content, pausing audio content, skipping forward in the audio content, rewinding the audio content, increasing a volume of audio content playing from the audio device, decreasing the volume of the audio content, activating a voice command mode, switching to ambient sound passthrough mode, scrolling through a message, mute, recording, or call control.

2. The method according to claim 1, wherein the audio device is an earphone.

3. The method according to claim 1, further comprising:
   receiving a second sensor signal; and
   analyzing the second sensor signal to detect voice activity.

4. The method according to claim 1, wherein the function is scrolling through a message.

5. The method according to claim 3, further comprising:
   receiving a microphone signal, wherein the microphone signal is generated by a microphone in the audio device; and
   analyzing the microphone signal to detect a voice control command.

6. The method according to claim 5, wherein the voice control command adjusts the function associated with the user gesture.

7. The method according to claim 5, wherein a logic circuit receives the voice control command prior to matching the user gesture, and wherein the logic circuit controls the function by at least one of analyzing the voice control command or the user gesture or a combination thereof.

8. The method according to claim 1, wherein the sensor is a bendable sensor.

9. The method according to claim 1, wherein the function is mute control, recording, or call control of the audio device.

10. The method according to claim 1, wherein the user gesture is pressing and rotating along the tubular structure.

11. The method according to claim 10, wherein rotating in one direction increases the volume while rotating in an opposite direction decreases the volume of audio played by the audio device.

12. The method according to claim 1, wherein the sensor is a touch or proximity sensor.

13. The method according to claim 1, wherein the sensor includes smart skin.

14. The method according to claim 1, wherein the sensor is a capacitive sensor.

15. A method of controlling an audio device comprising:
    receiving a sensor signal generated by a sensor, wherein the sensor is on or in a compressible tubular structure, wherein the compressible tubular structure is part of the earphone, wherein the sensor is a capacitive sensor, and wherein a change in a capacitance generates the sensor signal, wherein the earphone has a portion that fits within an ear canal, and wherein part of the compressible tubular structure is designed to be outside a concha of a user when the earphone is used;
    matching the sensor signal to a user gesture, wherein the user gesture results from the user touching the sensor or touching a cover on the sensor or touching the compressible tubular structure, wherein the user gesture is at least one of a finger movement along the compressible tubular structure, pinching the compressible tubular structure, double pressing the compressible tubular structure, triple pressing the compressible tubular structure, a press and then hold for a time period of the compressible tubular structure, a dual touch of the compressible tubular structure or pressing and rotating along the compressible tubular structure; and
    controlling a function of the audio device by associating the user gesture with the function, wherein the function is at least one of playing audio content, pausing audio content, skipping forward in the audio content, rewinding the audio content, increasing a volume of audio content playing from the audio device, decreasing the volume of the audio content, activating a voice command mode, switching to ambient sound passthrough mode, scrolling through a message, mute, recording, or call control.

16. A memory comprising instructions that when executed by a processor:
    receive a sensor signal generated by a sensor, wherein the sensor is on or in a tubular structure that is part of an earphone, the earphone having a portion that fits within an ear canal and a part of the tubular structure is outside a concha of a user when the earphone is being used by the user;
    match the sensor signal to a user gesture, wherein the user gesture results from the user touching the sensor or touching a cover on the sensor or touching the tubular structure, wherein the user gesture is at least one of a finger movement along the tubular structure, pinching the tubular structure, double pressing the tubular structure, triple pressing the tubular structure, a press and then hold for a time period of the tubular structure, a dual touch of the tubular structure or pressing and rotating along the tubular structure; and control a function that is associated with the user gesture, wherein the function is at least one of playing audio content, pausing audio content, skipping forward in the audio content, rewinding the audio content, increasing a volume of audio content playing from the earphone, decreasing the volume of the audio content, activating a voice command mode, switching to ambient sound passthrough mode, scrolling through a message, mute, recording, or call control.

17. The memory of claim 16 further comprising instructions that configure the processor to:

receive a microphone signal generated by a microphone in the earphone; and analyze the microphone signal to detect a voice control command.

18. The memory of claim 17 further comprising instructions that configure the processor to adjust the function associated with the user gesture using the voice control command.

19. The memory of claim 17, wherein the processor receives the voice control command prior to matching the sensor signal to the user gesture, and controls the function by at least one of analyzing the voice control command or the user gesture.

20. The memory of claim 16 wherein the user gesture is pressing and rotating along the tubular structure, and wherein rotating in one direction increases the volume of audio content playing from the earphone while rotating in an opposite direction decreases the volume.

* * * * *